(12) United States Patent
Nakase

(10) Patent No.: US 10,752,660 B2
(45) Date of Patent: Aug. 25, 2020

(54) FIBROIN-LIKE PROTEIN PRODUCTION METHOD

(71) Applicants: AJINOMOTO CO., INC., Tokyo (JP); SPIBER INC., Yamagata (JP)

(72) Inventor: Kentaro Nakase, Kanagawa (JP)

(73) Assignees: AJINOMOTO CO., INC., Tokyo (JP); SPIBER INC., Yamagata (JP)

(*) Notice: Subject to any disclaimer, the term of this patent is extended or adjusted under 35 U.S.C. 154(b) by 138 days.

(21) Appl. No.: 15/356,915

(22) Filed: Nov. 21, 2016

(65) Prior Publication Data
US 2017/0066805 A1 Mar. 9, 2017

Related U.S. Application Data

(63) Continuation of application No. PCT/JP2015/064656, filed on May 21, 2015.

(30) Foreign Application Priority Data

May 21, 2014 (JP) ................................ 2014-105623

(51) Int. Cl.
*C12N 15/09* (2006.01)
*C12N 15/70* (2006.01)
*C12N 1/00* (2006.01)
*C12P 21/02* (2006.01)
*C07K 14/435* (2006.01)

(52) U.S. Cl.
CPC ........ *C07K 14/43518* (2013.01); *C12N 15/70* (2013.01); *C12P 21/02* (2013.01); *C12N 1/00* (2013.01); *C12N 15/09* (2013.01)

(58) Field of Classification Search
None
See application file for complete search history.

(56) References Cited

U.S. PATENT DOCUMENTS

2006/0019348 A1* 1/2006 Asakura ........... C07K 14/43586
435/69.1
2014/0058066 A1 2/2014 Sekiyama et al.

FOREIGN PATENT DOCUMENTS

| EP | 0411501 A1 | 2/1991 |
|---|---|---|
| IE | 902785 A1 | 2/1991 |
| WO | WO97/08315 A1 | 3/1997 |
| WO | WO02/40697 A2 | 5/2002 |
| WO | WO2006/008163 A2 | 1/2006 |
| WO | WO2006/008163 A3 | 1/2006 |
| WO | WO2012/165476 A1 | 12/2012 |

OTHER PUBLICATIONS

Huang et al. Industrial production of recombinant therapeutics in *Escherichia coli* and its recent advancements. Published online Jan. 18, 2012. J. Ind. Microbiol. Biotechnol. vol. 39, pp. 383-399. (Year: 2012).*
Ruiz et al. From laboratory to pilot plant *E. coli* fed-batch cultures: optimizing the cellular environment for protein maximization. 2013. J. Ind. Microbial Biotechnol. vol. 40, pp. 335-343. (Year: 2013).*
Supplementary European Search Report for European Patent App. No. 15796845.4 (dated Jan. 9, 2018).
Tunner, J. R., et al., "Use of Glucose Starvation to Limit Growth and Induce Protein Production in *Escherichia coli*," Biotechnol. Bioeng. 1992;40(2):271-279.
Huber, R., et al., "Utilizing high-throughput experimentation to enhance specific productivity of an *E.coli* T7 expression system by phosphate limitation," BMC Biotechnol. 2011;11:22:pp. 1-11.
Curless, C., et al., "Effect of Preinduction Specific Growth Rate on Recombinant Alpha Consensus Interferon Synthesis in *Escherichia coli*," Biotechnol. Prog. 1990;6:149-152.
International Search Report for PCT Patent App. No. PCT/JP2015/064656 (dated Jun. 16, 2015).
Jensen, E. B., et al., "Production of Recombinant Human Growth Hormone in *Escherichia coli*: Expression of Different Precursors and Physiological Effects of Glucose, Acetate, and Salts," Biotechnol. Bioeng. 1990;36:1-11.
Riesenberg, D., et al., "High cell density fermentation of recombinant *Escherichia coli* expressing human interferon alpha 1," Appl. Microbiol. Biotechnol. 1990;34:77-82.
Seo, J.-H., et al., "Effects of Recombinant Plasmid Content on Growth Properties and Cloned Gene Product Formation in *Escherichia coli*," Biotechnol. Bioeng. 1985;27:1668-1674.
Siegel, R., et al., "Kinetic Study of Instability of Recombinant Plasmid pPLc23trpAl in *E. coli* Using Two-Stage Continuous Culture System," Biotechnol. Bioeng. 1985;27:28-33.
International Preliminary Report on Patentability for PCT Patent App. No. PCT/JP2015/064656 dated Dec. 1, 2016.

* cited by examiner

Primary Examiner — Channing S Mahatan
(74) Attorney, Agent, or Firm — Cermak Nakajima & McGowan LLP; Shelly Guest Cermak

(57) ABSTRACT

A method for producing a fibroin-like protein is described. A fibroin-like protein is produced by culturing *Escherichia coli* having a gene encoding the fibroin-like protein in a medium, inducing expression of the gene encoding the fibroin-like protein, and collecting the fibroin-like protein, wherein the cell proliferation after inducing the expression is reduced.

7 Claims, 17 Drawing Sheets

Specification includes a Sequence Listing.

(A)

(B)

(C)

(D)

(A)

(B)

(C)

(A)

(B)

(C)

(A)

(B)

(C)

(A)

(B)

(C)

(D)

(A)

(B)

(C)

(A)

(B)

(C)

(A)

(B)

(A)

(B)

(C)

(A)

(B)

(C)

SEQUENCE LISTING

<160> NUMBER OF SEQ ID NOS: 5

<210> SEQ ID NO 1
<211> LENGTH: 3465
<212> TYPE: DNA

<213> ORGANISM: Artificial Sequence
<220> FEATURE:
<223> OTHER INFORMATION: fibroin-like protein gene
<220> FEATURE:
<221> NAME/KEY: CDS
<222> LOCATION: (1)..(3465)

<400> SEQUENCE: 1

```
atg cat cac cat cat cat cat cac cac cac cat tcc tcg ggc tca tcc        48
Met His His His His His His His His His Ser Ser Gly Ser Ser
1               5                   10                  15 ttg gaa gtg tta ttt caa gga cca gca cga gcc ggt tcg gga caa caa        96
Leu Glu Val Leu Phe Gln Gly Pro Ala Arg Ala Gly Ser Gly Gln Gln
            20                  25                  30 ggg cct gga cag cag ggc cca ggt caa caa ggg cca gga cag cag ggt       144
Gly Pro Gly Gln Gln Gly Pro Gly Gln Gln Gly Pro Gly Gln Gln Gly
        35                  40                  45 cct tat ggg ccc ggc gca agc gca gca gct gcg gcc gct ggt ggc tat       192
Pro Tyr Gly Pro Gly Ala Ser Ala Ala Ala Ala Ala Ala Gly Gly Tyr
    50                  55                  60 ggt cct ggc tcc ggt caa cag ggc cct tcg caa caa ggt ccc ggg cag       240
Gly Pro Gly Ser Gly Gln Gln Gly Pro Ser Gln Gln Gly Pro Gly Gln
65                  70                  75                  80 caa ggt cct ggt ggc cag ggt ccc tac ggg ccg ggg gcg agt gcg gca       288
Gln Gly Pro Gly Gly Gln Gly Pro Tyr Gly Pro Gly Ala Ser Ala Ala
                85                  90                  95 gca gcc gct gca ggc ggt tat ggt cca gga agc gga cag caa ggt ccg       336
Ala Ala Ala Ala Gly Gly Tyr Gly Pro Gly Ser Gly Gln Gln Gly Pro
            100                 105                 110 gga ggt caa ggt ccg tat ggc cca ggc tct agc gcg gct gcc gct gcc       384
Gly Gly Gln Gly Pro Tyr Gly Pro Gly Ser Ser Ala Ala Ala Ala Ala
        115                 120                 125 gcg ggt ggc aac gga cca ggg agc gga caa cag ggc gcg gga caa cag       432
Ala Gly Gly Asn Gly Pro Gly Ser Gly Gln Gln Gly Ala Gly Gln Gln
    130                 135                 140 ggt cca gga cag caa ggc cca ggg gcg tcg gcg gct gca gcg gcg gcc       480
Gly Pro Gly Gln Gln Gly Pro Gly Ala Ser Ala Ala Ala Ala Ala Ala
145                 150                 155                 160 gga ggc tat gga ccc ggc tca gga caa cag gga ccg ggt caa caa gga       528
Gly Gly Tyr Gly Pro Gly Ser Gly Gln Gln Gly Pro Gly Gln Gln Gly
                165                 170                 175 ccc ggt ggc caa ggc ccc tat ggc ccg ggc gcc agc gcg gcc gca gcc       576
Pro Gly Gly Gln Gly Pro Tyr Gly Pro Gly Ala Ser Ala Ala Ala Ala
            180                 185                 190 gcc gcg ggc ggg tac ggc ccc ggt agc ggc cag gga cca ggt cag cag       624
Ala Ala Gly Gly Tyr Gly Pro Gly Ser Gly Gln Gly Pro Gly Gln Gln
        195                 200                 205 ggg cca gga ggt cag ggc cca tac ggt ccg ggc gca tcc gcg gcg gcg       672
Gly Pro Gly Gly Gln Gly Pro Tyr Gly Pro Gly Ala Ser Ala Ala Ala
    210                 215                 220 gca gcg gca ggt ggc tac ggt ccc gga agc ggc caa cag ggg cca ggg       720
Ala Ala Ala Gly Gly Tyr Gly Pro Gly Ser Gly Gln Gln Gly Pro Gly
225                 230                 235                 240 caa caa gga cca gga caa caa ggt cct ggg ggc caa gga ccg tat gga       768
Gln Gln Gly Pro Gly Gln Gln Gly Pro Gly Gly Gln Gly Pro Tyr Gly
                245                 250                 255 cca gga gca tca gct gca gcc gcg gca gct ggc ggt tac ggt cca ggc       816
Pro Gly Ala Ser Ala Ala Ala Ala Ala Ala Gly Gly Tyr Gly Pro Gly
            260                 265                 270 tac ggc cag cag ggt ccg ggt cag cag gga ccg gga ggc cag ggg cct       864
Tyr Gly Gln Gln Gly Pro Gly Gln Gln Gly Pro Gly Gly Gln Gly Pro
```

-continued

|  | 275 |  |  |  | 280 |  |  |  | 285 |  |  |  |  |
|---|---|---|---|---|---|---|---|---|---|---|---|---|---|
| tat | ggc | cct | ggc | gct | tcc | gca | gcc | agt | gcc | gct | tct | gga | gga tac ggg | 912 |
| Tyr | Gly | Pro | Gly | Ala | Ser | Ala | Ala | Ser | Ala | Ala | Ser | Gly | Gly Tyr Gly |  |
|  | 290 |  |  |  | 295 |  |  |  | 300 |  |  |  |  |  |

| ccg | gga | agc | ggt | cag | caa | ggc | cct | ggc | caa | caa | gga | cct | gga ggc caa | 960 |
| Pro | Gly | Ser | Gly | Gln | Gln | Gly | Pro | Gly | Gln | Gln | Gly | Pro | Gly Gly Gln |  |
| 305 |  |  |  |  | 310 |  |  |  | 315 |  |  |  | 320 |  |

| ggg | ccc | tac | ggc | cca | gga | gcc | tcg | gca | gcc | gca | gct | gcc | gca ggt ggg | 1008 |
| Gly | Pro | Tyr | Gly | Pro | Gly | Ala | Ser | Ala | Ala | Ala | Ala | Ala | Ala Gly Gly |  |
|  |  |  | 325 |  |  |  | 330 |  |  |  | 335 |  |  |  |

| tat | ggg | cca | ggt | agc | ggg | caa | caa | ggg | ccg | ggt | cag | caa | gga ccg ggg | 1056 |
| Tyr | Gly | Pro | Gly | Ser | Gly | Gln | Gln | Gly | Pro | Gly | Gln | Gln | Gly Pro Gly |  |
|  |  | 340 |  |  |  |  | 345 |  |  |  |  | 350 |  |  |

| caa | cag | gga | cct | ggg | cag | caa | gga | ccc | ggg | ggt | caa | ggc | ccg tac gga | 1104 |
| Gln | Gln | Gly | Pro | Gly | Gln | Gln | Gly | Pro | Gly | Gly | Gln | Gly | Pro Tyr Gly |  |
|  |  |  | 355 |  |  |  |  | 360 |  |  |  |  | 365 |  |  |

| cct | ggt | gcg | tct | gca | gct | gct | gct | gcg | gct | ggt | gga | tat | ggt ccg gga | 1152 |
| Pro | Gly | Ala | Ser | Ala | Ala | Ala | Ala | Ala | Ala | Gly | Gly | Tyr | Gly Pro Gly |  |
|  | 370 |  |  |  |  | 375 |  |  |  |  | 380 |  |  |  |  |

| tcg | ggg | cag | cag | ggt | ccc | ggt | cag | cag | ggc | cct | ggt | cag | caa ggg cca | 1200 |
| Ser | Gly | Gln | Gln | Gly | Pro | Gly | Gln | Gln | Gly | Pro | Gly | Gln | Gln Gly Pro |  |
| 385 |  |  |  |  | 390 |  |  |  | 395 |  |  |  | 400 |  |

| ggc | caa | cag | gga | ccc | gga | caa | caa | ggc | ccg | ggt | caa | cag | ggt cct gga | 1248 |
| Gly | Gln | Gln | Gly | Pro | Gly | Gln | Gln | Gly | Pro | Gly | Gln | Gln | Gly Pro Gly |  |
|  |  |  |  | 405 |  |  |  | 410 |  |  |  |  | 415 |  |  |

| cag | cag | ggg | ccg | ggc | caa | caa | ggc | cct | ggg | caa | cag | ggt | ccg ggg gga | 1296 |
| Gln | Gln | Gly | Pro | Gly | Gln | Gln | Gly | Pro | Gly | Gln | Gln | Gly | Pro Gly Gly |  |
|  |  |  | 420 |  |  |  |  | 425 |  |  |  |  | 430 |  |  |

| cag | ggg | gcc | tat | ggg | cct | ggc | gca | tct | gcc | gcc | gct | ggc | gca gcc ggt | 1344 |
| Gln | Gly | Ala | Tyr | Gly | Pro | Gly | Ala | Ser | Ala | Ala | Ala | Gly | Ala Ala Gly |  |
|  |  |  | 435 |  |  |  |  | 440 |  |  |  |  | 445 |  |  |

| ggg | tac | ggg | cct | ggg | tca | ggt | caa | cag | ggg | cct | ggt | caa | caa ggc ccc | 1392 |
| Gly | Tyr | Gly | Pro | Gly | Ser | Gly | Gln | Gln | Gly | Pro | Gly | Gln | Gln Gly Pro |  |
|  | 450 |  |  |  |  | 455 |  |  |  |  | 460 |  |  |  |  |

| ggg | caa | cag | ggc | ccc | ggc | cag | caa | ggt | cca | ggg | cag | cag | ggc ccg gga | 1440 |
| Gly | Gln | Gln | Gly | Pro | Gly | Gln | Gln | Gly | Pro | Gly | Gln | Gln | Gly Pro Gly |  |
| 465 |  |  |  |  | 470 |  |  |  | 475 |  |  |  | 480 |  |

| cag | caa | ggg | cct | gga | caa | cag | ggg | ccc | gga | cag | cag | gga | cct tac ggg | 1488 |
| Gln | Gln | Gly | Pro | Gly | Gln | Gln | Gly | Pro | Gly | Gln | Gln | Gly | Pro Tyr Gly |  |
|  |  |  |  | 485 |  |  |  | 490 |  |  |  |  | 495 |  |  |

| ccc | ggt | gcg | agc | gca | gcg | gcc | gcc | gcc | gca | ggg | gga | tat | ggc ccc gga | 1536 |
| Pro | Gly | Ala | Ser | Ala | Ala | Ala | Ala | Ala | Ala | Gly | Gly | Tyr | Gly Pro Gly |  |
|  |  |  | 500 |  |  |  | 505 |  |  |  |  | 510 |  |  |  |

| tcg | ggc | cag | cag | gga | cca | ggc | cag | caa | gga | cct | ggc | caa | cag ggc ccg | 1584 |
| Ser | Gly | Gln | Gln | Gly | Pro | Gly | Gln | Gln | Gly | Pro | Gly | Gln | Gln Gly Pro |  |
|  |  |  | 515 |  |  |  |  | 520 |  |  |  |  | 525 |  |  |

| ggg | ggt | cag | ggg | ccg | tat | ggt | ccc | ggc | gct | gca | agt | gct | gca gtg tcc | 1632 |
| Gly | Gly | Gln | Gly | Pro | Tyr | Gly | Pro | Gly | Ala | Ala | Ser | Ala | Ala Val Ser |  |
|  | 530 |  |  |  |  | 535 |  |  |  |  | 540 |  |  |  |  |

| gtt | tct | aga | gca | cga | gcc | ggt | tcg | gga | caa | caa | ggg | cct | ggc cag cag | 1680 |
| Val | Ser | Arg | Ala | Arg | Ala | Gly | Ser | Gly | Gln | Gln | Gly | Pro | Gly Gln Gln |  |
| 545 |  |  |  |  | 550 |  |  |  | 555 |  |  |  | 560 |  |

| ggc | cca | ggt | caa | caa | ggg | cca | gga | cag | cag | ggt | cct | tat | ggg ccc ggc | 1728 |
| Gly | Pro | Gly | Gln | Gln | Gly | Pro | Gly | Gln | Gln | Gly | Pro | Tyr | Gly Pro Gly |  |
|  |  |  |  | 565 |  |  |  | 570 |  |  |  |  | 575 |  |  |

| gca | agc | gca | gca | gct | gcg | gcc | gct | ggt | ggc | tat | ggt | cct | ggc tcc ggt | 1776 |
| Ala | Ser | Ala | Ala | Ala | Ala | Ala | Ala | Gly | Gly | Tyr | Gly | Pro | Gly Ser Gly |  |
|  |  |  | 580 |  |  |  | 585 |  |  |  |  | 590 |  |  |  |

| caa | cag | ggc | cct | tcg | caa | caa | ggt | ccc | ggg | cag | caa | ggt | cct ggt ggc | 1824 |

```
              Gln Gln Gly Pro Ser Gln Gln Gly Pro Gly Gln Gln Gly Pro Gly Gly
                              595                 600                 605 cag ggt ccc tac ggg ccg ggg gcg agt gcg gca gca gcc gct gca ggc              1872
Gln Gly Pro Tyr Gly Pro Gly Ala Ser Ala Ala Ala Ala Ala Ala Gly
    610                 615                 620 ggt tat ggt cca gga agc gga cag caa ggt ccg gga ggt caa ggt ccg              1920
Gly Tyr Gly Pro Gly Ser Gly Gln Gln Gly Pro Gly Gly Gln Gly Pro
625                 630                 635                 640 tat ggc cca ggc tct agc gcg gct gcc gct gcc gcg ggt ggc aac gga              1968
Tyr Gly Pro Gly Ser Ser Ala Ala Ala Ala Ala Ala Gly Gly Asn Gly
                645                 650                 655 cca ggg agc gga caa cag ggc gcg gga caa cag ggt cca gga cag caa              2016
Pro Gly Ser Gly Gln Gln Gly Ala Gly Gln Gln Gly Pro Gly Gln Gln
                660                 665                 670 ggc cca ggg gcg tcg gcg gct gca gcg gcg gcc gga ggc tat gga ccc              2064
Gly Pro Gly Ala Ser Ala Ala Ala Ala Ala Ala Gly Gly Tyr Gly Pro
            675                 680                 685 ggc tca gga caa cag gga ccg ggt caa caa gga ccc ggt ggc caa ggc              2112
Gly Ser Gly Gln Gln Gly Pro Gly Gln Gln Gly Pro Gly Gly Gln Gly
        690                 695                 700 ccc tat ggc ccg ggc gcc agc gcg gcc gca gcc gcc gcg ggc ggg tac              2160
Pro Tyr Gly Pro Gly Ala Ser Ala Ala Ala Ala Ala Ala Gly Gly Tyr
705                 710                 715                 720 ggc ccc ggt agc ggc cag gga cca ggt cag cag ggg cca gga ggt cag              2208
Gly Pro Gly Ser Gly Gln Gly Pro Gly Gln Gln Gly Pro Gly Gly Gln
                725                 730                 735 ggc cca tac ggt ccg ggc gca tcc gcg gcg gcg gca gcg gca ggt ggc              2256
Gly Pro Tyr Gly Pro Gly Ala Ser Ala Ala Ala Ala Ala Ala Gly Gly
                740                 745                 750 tac ggt ccc gga agc ggc caa cag ggg cca ggg caa caa gga cca gga              2304
Tyr Gly Pro Gly Ser Gly Gln Gln Gly Pro Gly Gln Gln Gly Pro Gly
            755                 760                 765 caa caa ggt cct ggg ggc caa gga ccg tat gga cca gga gca tca gct              2352
Gln Gln Gly Pro Gly Gly Gln Gly Pro Tyr Gly Pro Gly Ala Ser Ala
        770                 775                 780 gca gcc gcg gca gct ggc ggt tac ggt cca ggc tac ggc cag cag ggt              2400
Ala Ala Ala Ala Ala Gly Gly Tyr Gly Pro Gly Tyr Gly Gln Gln Gly
785                 790                 795                 800 ccg ggt cag cag gga ccg gga ggc cag ggg cct tat ggc cct ggc gct              2448
Pro Gly Gln Gln Gly Pro Gly Gly Gln Gly Pro Tyr Gly Pro Gly Ala
                805                 810                 815 tcc gca gcc agt gcc gct tct gga gga tac ggg ccg gga agc ggt cag              2496
Ser Ala Ala Ser Ala Ala Ser Gly Gly Tyr Gly Pro Gly Ser Gly Gln
            820                 825                 830 caa ggc cct ggc caa caa gga cct gga ggc caa ggg ccc tac ggc cca              2544
Gln Gly Pro Gly Gln Gln Gly Pro Gly Gly Gln Gly Pro Tyr Gly Pro
        835                 840                 845 gga gcc tcg gca gcc gca gct gcc gca ggt ggg tat ggg cca ggt agc              2592
Gly Ala Ser Ala Ala Ala Ala Ala Ala Gly Gly Tyr Gly Pro Gly Ser
    850                 855                 860 ggg caa caa ggg ccg ggt cag caa gga ccg ggg caa cag gga cct ggg              2640
Gly Gln Gln Gly Pro Gly Gln Gln Gly Pro Gly Gln Gln Gly Pro Gly
865                 870                 875                 880 cag caa gga ccc ggg ggt caa ggc ccg tac gga cct ggt gcg tct gca              2688
Gln Gln Gly Pro Gly Gly Gln Gly Pro Tyr Gly Pro Gly Ala Ser Ala
                885                 890                 895 gct gct gct gcg gct ggt gga tat ggt ccg gga tcg ggg cag cag ggt              2736
Ala Ala Ala Ala Ala Gly Gly Tyr Gly Pro Gly Ser Gly Gln Gln Gly
            900                 905                 910
```

| | | |
|---|---|---|
| ccc ggt cag cag ggc cct ggt cag caa ggg cca ggc caa cag gga ccc<br>Pro Gly Gln Gln Gly Pro Gly Gln Gln Gly Pro Gly Gln Gln Gly Pro<br>   915       920       925 | | 2784 |
| gga caa caa ggc ccg gtt caa cag ggt cct gga cag cag ggg ccg ggc<br>Gly Gln Gln Gly Pro Gly Gln Gln Gly Pro Gly Gln Gln Gly Pro Gly<br>930       935       940 | | 2832 |
| caa caa ggc cct ggg caa cag ggt ccg ggg gga cag ggg gcc tat ggg<br>Gln Gln Gly Pro Gly Gln Gln Gly Pro Gly Gly Gln Gly Ala Tyr Gly<br>945      950       955       960 | | 2880 |
| cct ggc gca tct gcc gcc gct ggc gca gcc ggt ggg tac ggg cct ggg<br>Pro Gly Ala Ser Ala Ala Ala Gly Ala Ala Gly Gly Tyr Gly Pro Gly<br>      965       970       975 | | 2928 |
| tca ggt caa cag ggg cct ggt caa caa ggc ccc ggg caa cag ggc ccc<br>Ser Gly Gln Gln Gly Pro Gly Gln Gln Gly Pro Gly Gln Gln Gly Pro<br>   980       985       990 | | 2976 |
| ggc cag caa ggt cca ggg cag cag ggc ccg gga cag caa ggg cct gga<br>Gly Gln Gln Gly Pro Gly Gln Gln Gly Pro Gly Gln Gln Gly Pro Gly<br>      995      1000      1005 | | 3024 |
| caa cag ggg ccc gga cag cag gga cct tac ggg ccc ggt gcg agc<br>Gln Gln Gly Pro Gly Gln Gln Gly Pro Tyr Gly Pro Gly Ala Ser<br>1010       1015       1020 | | 3069 |
| gca gcg gcc gcc gcc gca ggg gga tat ggc ccc gga tcg ggc cag<br>Ala Ala Ala Ala Ala Ala Gly Gly Tyr Gly Pro Gly Ser Gly Gln<br>1025       1030       1035 | | 3114 |
| cag gga cca ggc cag caa gga cct ggc caa cag ggc ccg ggg ggt<br>Gln Gly Pro Gly Gln Gln Gly Pro Gly Gln Gln Gly Pro Gly Gly<br>1040       1045       1050 | | 3159 |
| cag ggg ccg tat ggt ccc ggc gct gca agt gct gca gtg tcc gtt<br>Gln Gly Pro Tyr Gly Pro Gly Ala Ala Ser Ala Ala Val Ser Val<br>1055       1060       1065 | | 3204 |
| gga ggt tac ggc cct cag tct tcg tct gtt ccg gtg gcg tcc gca<br>Gly Gly Tyr Gly Pro Gln Ser Ser Ser Val Pro Val Ala Ser Ala<br>1070       1075       1080 | | 3249 |
| gtt gcg agt aga ctg tct tca cct gct gct tca tcg cga gta tcg<br>Val Ala Ser Arg Leu Ser Ser Pro Ala Ala Ser Ser Arg Val Ser<br>1085       1090       1095 | | 3294 |
| agc gct gtt tcg tct ctt gtc tcg tcg ggt ccc acg aaa cat gcc<br>Ser Ala Val Ser Ser Leu Val Ser Ser Gly Pro Thr Lys His Ala<br>1100       1105       1110 | | 3339 |
| gcc ctt tca aat acg att tca tct gta gtg tcc caa gtt agt gca<br>Ala Leu Ser Asn Thr Ile Ser Ser Val Val Ser Gln Val Ser Ala<br>1115       1120       1125 | | 3384 |
| agt aac ccg ggg tta tcc gga tgc gac gtt ctc gtt cag gca ctc<br>Ser Asn Pro Gly Leu Ser Gly Cys Asp Val Leu Val Gln Ala Leu<br>1130       1135       1140 | | 3429 |
| cta gaa gta gta tcc gcg ttg gtg agc atc tta taa<br>Leu Glu Val Val Ser Ala Leu Val Ser Ile Leu<br>1145       1150 | | 3465 |

<210> SEQ ID NO 2
<211> LENGTH: 1154
<212> TYPE: PRT
<213> ORGANISM: Artificial Sequence
<220> FEATURE:
<223> OTHER INFORMATION: Synthetic Construct

<400> SEQUENCE: 2

Met His His His His His His His His His Ser Ser Gly Ser Ser
1      5        10        15

Leu Glu Val Leu Phe Gln Gly Pro Ala Arg Ala Gly Ser Gly Gln Gln
      20        25        30

```
Gly Pro Gly Gln Gln Gly Pro Gln Gln Gly Pro Gly Gln Gln Gly
         35                  40                  45
Pro Tyr Gly Pro Gly Ala Ser Ala Ala Ala Ala Ala Gly Gly Tyr
     50                  55                  60
Gly Pro Gly Ser Gly Gln Gln Gly Pro Ser Gln Gln Gly Pro Gly Gln
 65                  70                  75                  80
Gln Gly Pro Gly Gly Gln Gly Pro Tyr Gly Pro Gly Ala Ser Ala Ala
                 85                  90                  95
Ala Ala Ala Ala Gly Gly Tyr Gly Pro Gly Ser Gln Gln Gly Pro
             100                 105                 110
Gly Gly Gln Gly Pro Tyr Gly Pro Gly Ser Ala Ala Ala Ala
         115                 120                 125
Ala Gly Gly Asn Gly Pro Gly Ser Gly Gln Gln Gly Ala Gly Gln Gln
             130                 135                 140
Gly Pro Gly Gln Gln Gly Pro Gly Ala Ser Ala Ala Ala Ala Ala
145                 150                 155                 160
Gly Gly Tyr Gly Pro Gly Ser Gly Gln Gln Gly Pro Gly Gln Gln Gly
             165                 170                 175
Pro Gly Gly Gln Gly Pro Tyr Gly Pro Gly Ala Ser Ala Ala Ala
         180                 185                 190
Ala Ala Gly Gly Tyr Gly Pro Gly Ser Gly Gln Gly Pro Gly Gln Gln
         195                 200                 205
Gly Pro Gly Gly Gln Gly Pro Tyr Gly Pro Gly Ala Ser Ala Ala Ala
         210                 215                 220
Ala Ala Ala Gly Gly Tyr Gly Pro Gly Ser Gly Gln Gln Gly Pro Gly
225                 230                 235                 240
Gln Gln Gly Pro Gly Gln Gln Gly Pro Gly Gln Gly Pro Tyr Gly
             245                 250                 255
Pro Gly Ala Ser Ala Ala Ala Ala Ala Gly Gly Tyr Gly Pro Gly
         260                 265                 270
Tyr Gly Gln Gln Gly Pro Gly Gln Gln Gly Pro Gly Gln Gly Pro
     275                 280                 285
Tyr Gly Pro Gly Ala Ser Ala Ala Ser Ala Ala Ser Gly Gly Tyr Gly
     290                 295                 300
Pro Gly Ser Gly Gln Gln Gly Pro Gly Gln Gln Gly Pro Gly Gln
305                 310                 315                 320
Gly Pro Tyr Gly Pro Gly Ala Ser Ala Ala Ala Ala Ala Gly Gly
         325                 330                 335
Tyr Gly Pro Gly Ser Gly Gln Gln Gly Pro Gly Gln Gln Gly Pro Gly
             340                 345                 350
Gln Gln Gly Pro Gly Gln Gln Gly Pro Gly Gln Gln Gly Pro Tyr Gly
             355                 360                 365
Pro Gly Ala Ser Ala Ala Ala Ala Ala Gly Gly Tyr Gly Pro Gly
     370                 375                 380
Ser Gly Gln Gln Gly Pro Gly Gln Gln Gly Pro Gly Gln Gln Gly Pro
385                 390                 395                 400
Gly Gln Gln Gly Pro Gly Gln Gln Gly Pro Gly Gln Gln Gly Pro Gly
             405                 410                 415
Gln Gln Gly Pro Gly Gln Gln Gly Pro Gly Gln Gln Gly Pro Gly Gly
             420                 425                 430
Gln Gly Ala Tyr Gly Pro Gly Ala Ser Ala Ala Gly Ala Ala Gly
             435                 440                 445
```

```
Gly Tyr Gly Pro Gly Ser Gly Gln Gln Gly Pro Gln Gln Gly Pro
    450                 455                 460

Gly Gln Gln Gly Pro Gly Gln Gln Gly Pro Gln Gln Gly Pro Gly
465                 470                 475                 480

Gln Gln Gly Pro Gly Gln Gln Gly Pro Gln Gln Gly Pro Tyr Gly
                485                 490                 495

Pro Gly Ala Ser Ala Ala Ala Ala Ala Gly Gly Tyr Gly Pro Gly
            500                 505                 510

Ser Gly Gln Gln Gly Pro Gly Gln Gln Gly Pro Gly Gln Gln Gly Pro
        515                 520                 525

Gly Gly Gln Gly Pro Tyr Gly Pro Gly Ala Ala Ser Ala Ala Val Ser
    530                 535                 540

Val Ser Arg Ala Arg Ala Gly Ser Gly Gln Gln Gly Pro Gly Gln Gln
545                 550                 555                 560

Gly Pro Gly Gln Gln Gly Pro Gly Gln Gln Gly Pro Tyr Gly Pro Gly
                565                 570                 575

Ala Ser Ala Ala Ala Ala Ala Gly Gly Tyr Gly Pro Gly Ser Gly
            580                 585                 590

Gln Gln Gly Pro Ser Gln Gln Gly Pro Gly Gln Gln Gly Pro Gly Gly
        595                 600                 605

Gln Gly Pro Tyr Gly Pro Gly Ala Ser Ala Ala Ala Ala Ala Gly
    610                 615                 620

Gly Tyr Gly Pro Gly Ser Gly Gln Gln Gly Pro Gly Gln Gln Gly Pro
625                 630                 635                 640

Tyr Gly Pro Gly Ser Ser Ala Ala Ala Ala Ala Gly Gly Asn Gly
                645                 650                 655

Pro Gly Ser Gly Gln Gln Gly Ala Gly Gln Gln Gly Pro Gly Gln Gln
            660                 665                 670

Gly Pro Gly Ala Ser Ala Ala Ala Ala Ala Gly Gly Tyr Gly Pro
        675                 680                 685

Gly Ser Gly Gln Gln Gly Pro Gly Gln Gln Gly Pro Gly Gly Gln Gly
    690                 695                 700

Pro Tyr Gly Pro Gly Ala Ser Ala Ala Ala Ala Ala Gly Gly Tyr
705                 710                 715                 720

Gly Pro Gly Ser Gly Gln Gly Pro Gly Gln Gln Gly Pro Gly Gly Gln
                725                 730                 735

Gly Pro Tyr Gly Pro Gly Ala Ser Ala Ala Ala Ala Ala Gly Gly
            740                 745                 750

Tyr Gly Pro Gly Ser Gly Gln Gln Gly Pro Gly Gln Gln Gly Pro Gly
        755                 760                 765

Gln Gln Gly Pro Gly Gly Gln Gly Pro Tyr Gly Pro Gly Ala Ser Ala
    770                 775                 780

Ala Ala Ala Ala Gly Gly Tyr Gly Pro Gly Tyr Gly Gln Gln Gly
785                 790                 795                 800

Pro Gly Gln Gln Gly Pro Gly Gly Gln Gly Pro Tyr Gly Pro Gly Ala
                805                 810                 815

Ser Ala Ala Ser Ala Ala Ser Gly Gly Tyr Gly Pro Gly Ser Gly Gln
            820                 825                 830

Gln Gly Pro Gly Gln Gln Gly Pro Gly Gly Gln Gly Pro Tyr Gly Pro
        835                 840                 845

Gly Ala Ser Ala Ala Ala Ala Ala Gly Gly Tyr Gly Pro Gly Ser
    850                 855                 860

Gly Gln Gln Gly Pro Gly Gln Gln Gly Pro Gly Gln Gln Gly Pro Gly
```

```
            865                 870                 875                 880
        Gln Gln Gly Pro Gly Gly Gln Gly Pro Tyr Gly Pro Gly Ala Ser Ala
                        885                 890                 895

Ala Ala Ala Ala Ala Gly Gly Tyr Gly Pro Gly Ser Gly Gln Gln Gly
                        900                 905                 910

Pro Gly Gln Gln Gly Pro Gly Gln Gln Gly Pro Gly Gln Gln Gly Pro
                        915                 920                 925

Gly Gln Gln Gly Pro Gly Gln Gln Gly Pro Gly Gln Gln Gly Pro Gly
                        930                 935                 940

Gln Gln Gly Pro Gly Gln Gln Gly Pro Gly Gln Gln Gly Ala Tyr Gly
        945                 950                 955                 960

Pro Gly Ala Ser Ala Ala Ala Gly Ala Ala Gly Gly Tyr Gly Pro Gly
                        965                 970                 975

Ser Gly Gln Gln Gly Pro Gly Gln Gln Gly Pro Gly Gln Gln Gly Pro
                        980                 985                 990

Gly Gln Gln Gly Pro Gly Gln Gln Gly Pro Gly Gln Gln Gly Pro Gly
                        995                 1000                1005

Gln Gln Gly Pro Gly Gln Gln Gly Pro Tyr Gly Pro Gly Ala Ser
            1010                1015                1020

Ala Ala Ala Ala Ala Gly Gly Tyr Gly Pro Gly Ser Gly Gln
            1025                1030                1035

Gln Gly Pro Gly Gln Gln Gly Pro Gly Gln Gln Gly Pro Gly Gly
            1040                1045                1050

Gln Gly Pro Tyr Gly Pro Gly Ala Ala Ser Ala Ala Val Ser Val
            1055                1060                1065

Gly Gly Tyr Gly Pro Gln Ser Ser Ser Val Pro Val Ala Ser Ala
            1070                1075                1080

Val Ala Ser Arg Leu Ser Ser Pro Ala Ala Ser Ser Arg Val Ser
            1085                1090                1095

Ser Ala Val Ser Ser Leu Val Ser Ser Gly Pro Thr Lys His Ala
            1100                1105                1110

Ala Leu Ser Asn Thr Ile Ser Ser Val Val Ser Gln Val Ser Ala
            1115                1120                1125

Ser Asn Pro Gly Leu Ser Gly Cys Asp Val Leu Val Gln Ala Leu
            1130                1135                1140

Leu Glu Val Val Ser Ala Leu Val Ser Ile Leu
            1145                1150

<210> SEQ ID NO 3
<211> LENGTH: 636
<212> TYPE: PRT
<213> ORGANISM: Araneus diadematus

<400> SEQUENCE: 3

Ala Arg Ala Gly Ser Gly Gln Gln Gly Pro Gly Gln Gln Gly Pro Gly
        1               5                   10                  15

Gln Gln Gly Pro Gly Gln Gln Gly Pro Tyr Gly Pro Gly Ala Ser Ala
                        20                  25                  30

Ala Ala Ala Ala Ala Gly Gly Tyr Gly Pro Gly Ser Gly Gln Gln Gly
                35                  40                  45

Pro Ser Gln Gln Gly Pro Gly Gln Gln Gly Pro Gly Gln Gln Gly Pro
                50                  55                  60

Tyr Gly Pro Gly Ala Ser Ala Ala Ala Ala Ala Gly Gly Tyr Gly
        65                  70                  75                  80
```

```
Pro Gly Ser Gly Gln Gly Pro Gly Gln Gly Pro Tyr Gly Pro
            85                  90                  95

Gly Ser Ser Ala Ala Ala Ala Ala Gly Gly Asn Gly Pro Gly Ser
            100                 105                 110

Gly Gln Gln Gly Ala Gly Gln Gly Pro Gly Gln Gln Gly Pro Gly
            115                 120                 125

Ala Ser Ala Ala Ala Ala Ala Gly Tyr Gly Pro Gly Ser Gly
            130                 135                 140

Gln Gln Gly Pro Gly Gln Gln Gly Pro Gly Gln Gly Pro Tyr Gly
145                 150                 155                 160

Pro Gly Ala Ser Ala Ala Ala Ala Ala Gly Gly Tyr Gly Pro Gly
                    165                 170                 175

Ser Gly Gln Gly Pro Gly Gln Gln Gly Pro Gly Gln Gly Pro Tyr
            180                 185                 190

Gly Pro Gly Ala Ser Ala Ala Ala Ala Ala Gly Gly Tyr Gly Pro
            195                 200                 205

Gly Ser Gly Gln Gln Gly Pro Gly Gln Gln Gly Pro Gly Gln Gln Gly
            210                 215                 220

Pro Gly Gln Gly Pro Tyr Gly Pro Gly Ala Ser Ala Ala Ala Ala
225                 230                 235                 240

Ala Ala Gly Gly Tyr Gly Pro Gly Tyr Gly Gln Gln Gly Pro Gly Gln
                245                 250                 255

Gln Gly Pro Gly Gly Gln Pro Tyr Gly Pro Gly Ala Ser Ala Ala
            260                 265                 270

Ser Ala Ala Ser Gly Gly Tyr Gly Pro Gly Ser Gly Gln Gln Gly Pro
            275                 280                 285

Gly Gln Gln Gly Pro Gly Gln Gly Pro Tyr Gly Pro Gly Ala Ser
            290                 295                 300

Ala Ala Ala Ala Ala Ala Gly Gly Tyr Gly Pro Gly Ser Gly Gln Gln
305                 310                 315                 320

Gly Pro Gly Gln Gln Gly Pro Gly Gln Gln Gly Pro Gly Gln Gln Gly
            325                 330                 335

Pro Gly Gln Gly Pro Tyr Gly Pro Gly Ala Ser Ala Ala Ala Ala
            340                 345                 350

Ala Ala Gly Gly Tyr Gly Pro Gly Ser Gly Gln Gln Gly Pro Gly Gln
            355                 360                 365

Gln Gly Pro Gly Gln Gln Gly Pro Gly Gln Gln Gly Pro Gly Gln Gln
            370                 375                 380

Gly Pro Gly Gln Gln Gly Pro Gly Gln Gln Gly Pro Gly Gln Gln Gly
385                 390                 395                 400

Pro Gly Gln Gln Gly Pro Gly Gly Gln Gly Ala Tyr Gly Pro Gly Ala
                    405                 410                 415

Ser Ala Ala Ala Gly Ala Ala Gly Gly Tyr Gly Pro Gly Ser Gly Gln
            420                 425                 430

Gln Gly Pro Gly Gln Gln Gly Pro Gly Gln Gln Gly Pro Gly Gln Gln
            435                 440                 445

Gly Pro Gly Gln Gln Gly Pro Gly Gln Gln Gly Pro Gly Gln Gln Gly
            450                 455                 460

Pro Gly Gln Gln Gly Pro Tyr Gly Pro Gly Ala Ser Ala Ala Ala Ala
465                 470                 475                 480

Ala Ala Gly Gly Tyr Gly Pro Gly Ser Gly Gln Gln Gly Pro Gly Gln
            485                 490                 495

Gln Gly Pro Gly Gln Gln Gly Pro Gly Gly Gln Gly Pro Tyr Gly Pro
```

```
            500             505             510
Gly Ala Ala Ser Ala Ala Val Ser Val Gly Gly Tyr Gly Pro Gln Ser
            515             520             525

Ser Ser Val Pro Val Ala Ser Ala Val Ala Ser Arg Leu Ser Ser Pro
        530             535             540

Ala Ala Ser Ser Arg Val Ser Ser Ala Val Ser Ser Leu Val Ser Ser
545             550             555             560

Gly Pro Thr Lys His Ala Ala Leu Ser Asn Thr Ile Ser Ser Val Val
            565             570             575

Ser Gln Val Ser Ala Ser Asn Pro Gly Leu Ser Gly Cys Asp Val Leu
        580             585             590

Val Gln Ala Leu Leu Glu Val Val Ser Ala Leu Val Ser Ile Leu Gly
        595             600             605

Ser Ser Ser Ile Gly Gln Ile Asn Tyr Gly Ala Ser Ala Gln Tyr Thr
        610             615             620

Gln Met Val Gly Gln Ser Val Ala Gln Ala Leu Ala
625             630             635

<210> SEQ ID NO 4
<211> LENGTH: 2190
<212> TYPE: DNA
<213> ORGANISM: Araneus diadematus

<400> SEQUENCE: 4
agatatacat aatgcaccac catcaccacc atcatcacca tcatagcagc ggcagcagcc      60
tggaagttct gtttcagggt ccggcgcgtg cgggtagcgg ccagcagggc ccgggtcagc     120
agggtccggg ccaacaaggt ccgggccagc agggcccgta tggtccgggt gcaagcgcag     180
cagcagcggc cgcaggcggt tacgcccggg tagcggcca gcagggcccg agccagcagg     240
gcccgggcca gcagggtccg gcggtcagg gtccgtacgg tccgggcgcg agcgcggccg     300
ccgcggccga aggcggttac gggccgggca gcgtcagca gggcccgggc ggtcagggcc     360
cgtatggccc gggtagcagc gcggccgcgg cggccgcagg cggtaatggt ccgggcagcg     420
gccagcaggg tgcgggccaa caaggcccgg gtcagcaggg cccgggtgcc agcgccgccg     480
cagcggccgc aggcggttac ggtccgggta gcggtcagca gggtcctggc caacaaggcc     540
cgggcggtca aggtccttac ggccggggcg ccagcgccgc ggctgcggcc gcaggcggtt     600
acggaccggg tagcggccag ggtcctggtc aacaaggtcc gggcggtcaa ggcccgtatg     660
gtccgggcgc cagcgcggcg gccgcggccg caggcggtta cgggccaggt agcggccagc     720
agggtcctgg ccagcagggt cctggacaac aaggaccggg cggtcaagga ccgtacggcc     780
cgggcgcgag cgccgcggca gcggccgcag gcggttatgg tccgggttac ggtcagcagg     840
gtcccggtca acagggaccg gcggtcaag gtccgtatgg cccgggtgcg agcgcggcca     900
gcgcagcgag cggcggttac ggtcctggtt ctggtcagca gggtcctgga cagcaaggtc     960
cgggcggtca gggaccttac ggtccgggtg cgagcgccgc agcggccgca gcgggcggtt    1020
acggccctgg ctctggtcag cagggtccag gtcaacaggg tcctggtcaa cagggtcccg    1080
gtcagcaagg cccgggcggt cagggtcctt atggtccggg cgcaagcgcg ccgccgccg    1140
cagcgggcgg ttacggtcct ggcagtggtc agcagggtcc gggacaacag ggtcctggac    1200
agcagggtcc tggcagcag ggtcctggtc agcaaggtcc tgtcagcag ggccctggcc    1260
agcagggtcc cggtcagcag ggccctggtc aacaaggacc gggcggtcag ggcgcgtatg    1320
gtccgggtgc cagcgccgca gcgggcgccg caggcggtta cgggcctggt agtggtcaac    1380
```

```
agggqcctgg ccaacagggc cctggtcagc aaggccctgg tcaacagggc cctggtcagc   1440
agggccccgg tcaacagggc cccggtcaac agggtccagg tcagcaaggt ccgtacggcc   1500
cgggcgcaag cgccgcggca gcggccgcag gcggttacgg gcccggctct ggtcaacagg   1560
ggcccggtca acagggccca ggtcaacagg ggccgggcgg tcaagggcct tatggcccgg   1620
gcgccgcgag cgccgccgtg agcgttggcg gttacggtcc gcagagcagc agcgtgccgg   1680
ttgccagcgc agtggccagc cgcctgagca gcccggccgc gagcagccgt gtgagcagcg   1740
cagttagcag cttagtgagc agcggtccga ccaaacatgc cgcgctgagc aacacgatta   1800
gcagcgtggt tagccaggtt tctgcaagca atccgggtct gagcggttgc gatgtgctgg   1860
ttcaggcgct gctggaagtg gttagcgcct tagtgagcat cctgggcagc agcagcattg   1920
gccagatcaa ttatggcgcg agcgcccagt acacccagat ggttggtcag agcgtggcac   1980
aggccctggc gtgaaattcg agctccgtcg acaagcttgc ggccgcactc gagcaccacc   2040
accaccacca ctgagatccg gctgctaaca aagcccgaaa ggaagctgag ttggctgctg   2100
ccaccgctga gcaataacta gcataacccc ttggggcctc taaacgggtc ttgaggggtt   2160
ttttgctgaa aggaggaact atatccggat                                     2190
```

<210> SEQ ID NO 5
<211> LENGTH: 660
<212> TYPE: PRT
<213> ORGANISM: Araneus diadematus

<400> SEQUENCE: 5

```
Met His His His His His His His His Ser Ser Gly Ser Ser
1               5                   10                  15

Leu Glu Val Leu Phe Gln Gly Pro Ala Arg Ala Gly Ser Gly Gln Gln
                20                  25                  30

Gly Pro Gly Gln Gln Gly Pro Gly Gln Gln Gly Pro Gly Gln Gln Gly
            35                  40                  45

Pro Tyr Gly Pro Gly Ala Ser Ala Ala Ala Ala Ala Gly Gly Tyr
        50                  55                  60

Gly Pro Gly Ser Gly Gln Gln Gly Pro Ser Gln Gln Gly Pro Gly Gln
65                  70                  75                  80

Gln Gly Pro Gly Gly Gln Gly Pro Tyr Gly Pro Gly Ala Ser Ala Ala
                85                  90                  95

Ala Ala Ala Ala Gly Gly Tyr Gly Pro Gly Ser Gly Gln Gln Gly Pro
            100                 105                 110

Gly Gly Gln Gly Pro Tyr Gly Pro Gly Ser Ser Ala Ala Ala Ala Ala
        115                 120                 125

Ala Gly Gly Asn Gly Pro Gly Ser Gly Gln Gln Gly Ala Gly Gln Gln
    130                 135                 140

Gly Pro Gly Gln Gln Gly Pro Gly Ala Ser Ala Ala Ala Ala Ala
145                 150                 155                 160

Gly Gly Tyr Gly Pro Gly Ser Gly Gln Gln Gly Pro Gly Gln Gln Gly
                165                 170                 175

Pro Gly Gly Gln Gly Pro Tyr Gly Pro Gly Ala Ser Ala Ala Ala Ala
            180                 185                 190

Ala Ala Gly Gly Tyr Gly Pro Gly Ser Gly Gln Gln Gly Pro Gly Gln Gln
        195                 200                 205

Gly Pro Gly Gly Gln Gly Pro Tyr Gly Pro Gly Ala Ser Ala Ala Ala
    210                 215                 220
```

```
Ala Ala Ala Gly Gly Tyr Gly Pro Gly Ser Gly Gln Gln Gly Pro Gly
225                 230                 235                 240

Gln Gln Gly Pro Gly Gln Gln Gly Pro Gly Gly Gln Gly Pro Tyr Gly
            245                 250                 255

Pro Gly Ala Ser Ala Ala Ala Ala Ala Gly Gly Tyr Gly Pro Gly
        260                 265                 270

Tyr Gly Gln Gln Gly Pro Gly Gln Gln Gly Pro Gly Gly Gln Gly Pro
    275                 280                 285

Tyr Gly Pro Gly Ala Ser Ala Ala Ser Ala Ala Ser Gly Gly Tyr Gly
    290                 295                 300

Pro Gly Ser Gly Gln Gln Gly Pro Gly Gln Gln Gly Pro Gly Gly Gln
305                 310                 315                 320

Gly Pro Tyr Gly Pro Gly Ala Ser Ala Ala Ala Ala Ala Gly Gly
        325                 330                 335

Tyr Gly Pro Gly Ser Gly Gln Gln Gly Pro Gly Gln Gln Gly Pro Gly
            340                 345                 350

Gln Gln Gly Pro Gly Gln Gln Gly Pro Gly Gly Gln Gly Pro Tyr Gly
            355                 360                 365

Pro Gly Ala Ser Ala Ala Ala Ala Ala Gly Gly Tyr Gly Pro Gly
        370                 375                 380

Ser Gly Gln Gln Gly Pro Gly Gln Gln Gly Pro Gly Gly Gln Gly Pro
385                 390                 395                 400

Gly Gln Gln Gly Pro Gly Gln Gln Gly Pro Gly Gln Gln Gly Pro Gly
            405                 410                 415

Gln Gln Gly Pro Gly Gln Gln Gly Pro Gly Gln Gln Gly Pro Gly Gly
            420                 425                 430

Gln Gly Ala Tyr Gly Pro Gly Ala Ser Ala Ala Gly Ala Ala Gly
        435                 440                 445

Gly Tyr Gly Pro Gly Ser Gly Gln Gln Gly Pro Gly Gln Gln Gly Pro
        450                 455                 460

Gly Gln Gln Gly Pro Gly Gln Gln Gly Pro Gly Gln Gln Gly Pro Gly
465                 470                 475                 480

Gln Gln Gly Pro Gly Gln Gln Gly Pro Gly Gln Gln Gly Pro Tyr Gly
            485                 490                 495

Pro Gly Ala Ser Ala Ala Ala Ala Ala Gly Gly Tyr Gly Pro Gly
        500                 505                 510

Ser Gly Gln Gln Gly Pro Gly Gln Gln Gly Pro Gly Gln Gln Gly Pro
515                 520                 525

Gly Gly Gln Gly Pro Tyr Gly Pro Gly Ala Ala Ser Ala Ala Val Ser
            530                 535                 540

Val Gly Gly Tyr Gly Pro Gln Ser Ser Val Pro Val Ala Ser Ala
545                 550                 555                 560

Val Ala Ser Arg Leu Ser Ser Pro Ala Ala Ser Ser Arg Val Ser Ser
            565                 570                 575

Ala Val Ser Ser Leu Val Ser Ser Gly Pro Thr Lys His Ala Ala Leu
        580                 585                 590

Ser Asn Thr Ile Ser Ser Val Val Ser Gln Val Ser Ala Ser Asn Pro
        595                 600                 605

Gly Leu Ser Gly Cys Asp Val Leu Val Gln Ala Leu Leu Glu Val Val
        610                 615                 620
```

-continued

```
Ser Ala Leu Val Ser Ile Leu Gly Ser Ser Ser Ile Gly Gln Ile Asn
625                 630                 635                 640

Tyr Gly Ala Ser Ala Gln Tyr Thr Gln Met Val Gly Gln Ser Val Ala
                645                 650                 655

Gln Ala Leu Ala
            660
```

US 10,752,660 B2

FIBROIN-LIKE PROTEIN PRODUCTION METHOD

This application is a Continuation of, and claims priority under 35 U.S.C. § 120 to, International Application No. PCT/JP2015/064656, filed May 21, 2015, and claims priority therethrough under 35 U.S.C. § 119 to Japanese Patent Application No. 2014-105623, filed May 21, 2014, the entireties of which are incorporated by reference herein. Also, the Sequence Listing filed electronically herewith is hereby incorporated by reference (File name: 2016-11-21T_US-557_Seq List; File size: 40 KB; Date recorded: Nov. 21, 2016).

BACKGROUND OF THE INVENTION

Field of the Invention

The present invention relates to a method for producing a fibroin-like protein using heterogeneous expression in *Escherichia coli*.

Brief Description of the Related Art

Fibroin is a fibrous protein that is found in spider's thread and silkworm's thread. Spider's thread is a material that is four times stronger than steel, and tougher than carbon fiber and aramid fiber, and is highly elastic and heat resistant to heat. Therefore, the ability to conduct large-scale production of the constituents that make up these threads, such as fibroin or a fibrous proteins that are similar in structure to that of fibroin (henceforth generically referred to as "fibroin-like protein").

As for the production of fibroin-like protein, heterogeneous expression thereof using *Escherichia coli* has been reported (WO2012/165476 and WO2006/008163).

It is also known that, in heterogeneous expression of proteins using *Escherichia coli*, the specific proliferation rate of bacterial cells correlates with the specific production rate of the heterogeneous protein. However, it has also been reported that, for example, the specific production rate of the TrpA1 protein in *Escherichia coli* is more greatly improved as the specific proliferation rate increases (R. Siegel and D. D. Y. Ryu, Biotechnol. Bioeng., 27:28-33 (1985)), whereas the specific production rate of β-lactamase in *Escherichia coli* is more greatly reduced as the specific proliferation rate increases (Seo, J.-H., Bailey, J. E., 1985b, Biotechnol. Bioeng., 27:1668-1674). Although the production amount of interferon α1 in *Escherichia coli* increases with reduced growth rate by glucose limitation, it is not influenced by phosphate limitation (Riesenberg D., Menzel K., Schulz V, Schumann K., Veith G., Zuber G., Knorre W. A., Appl. Microbiol. Biotechnol., 1990 October; 34(1):77-82). Furthermore, the yield of recombinant interferon α in *Escherichia coli* increases as the specific proliferation rate before inducing the expression increases (C. Curless, J. Pope, L. Tsai, Biotechnol. Prog., 1990, 6(2), pp. 149-152). Also, the expression amount of human growth hormone (hGH) in *Escherichia coli* is doubled by depletion of phosphate (Bech Jensen, E. and Carlsen, S., Biotechnol. Bioeng., 36:1-11, 1990). As described above, consistent relevance is not observed between the specific proliferation rate of cells or limitation of medium component, and the specific production rate of a heterogeneous protein.

SUMMARY OF THE INVENTION

Aspects to be Achieved by the Invention

An aspect of the present invention is to provide an efficient method for producing a fibroin-like protein.

It has been found that when a fibroin-like protein is heterogeneously expressed in *Escherichia coli*, production of the fibroin-like protein can be improved by reducing cell proliferation after induction of expression of the fibroin-like protein.

It is an aspect of the present invention to provide a method for producing a fibroin-like protein, the method comprising A) culturing an *Escherichia coli* bacterium having a gene encoding the fibroin-like protein in a medium; B) inducing expression of the gene encoding the fibroin-like protein; and C) collecting the fibroin-like protein, wherein cell proliferation after inducing the expression is reduced.

It is a further aspect of the present invention to provide the method as described above, wherein a parameter selected from the group consisting of a) the cell growth rate, b) cell growth rate slope, c) cumulative specific proliferation rate, and d) combinations thereof, are reduced after inducing the expression.

It is a further aspect of the present invention to provide the method as described above, wherein the cell proliferation after inducing the expression is reduced by limiting a growth factor in said culturing during a period after inducing the expression.

It is a further aspect of the present invention to provide the method as described above, wherein the growth factor is selected from the group consisting of a a) carbon source, b) nitrogen source, c) phosphate source, d) sulfur source, e) mineral, f) nutrient required because of auxotrophy, and g) combinations thereof.

It is a further aspect of the present invention to provide the method as described above, wherein the growth factor is selected from the group consisting of a a) carbon source, b) organic nitrogen source, c) phosphate source, and d) combinations thereof.

It is a further aspect of the present invention to provide the method as described above, wherein said limiting occurs by reducing the concentration of the growth factor in the medium at the start of the culture.

It is a further aspect of the present invention to provide the method as described above, wherein said limiting occurs by reducing the feeding amount of the growth factor during a period after inducing the expression.

It is a further aspect of the present invention to provide the method as described above, wherein the ratio of the growth factor with respect to all ingredients in a feed medium fed during a period after inducing the expression is lower than 30% (w/w).

It is a further aspect of the present invention to provide the method as described above, wherein the ratio of a carbon source with respect to all ingredients in the feed medium fed during a period after inducing the expression is 70% (w/w) or higher.

It is a further aspect of the present invention to provide the method as described above, wherein said culturing is performed so that the cumulative specific carbon source consumption rate is 0.35 g/g/hr or lower during the period after inducing the expression.

It is a further aspect of the present invention to provide the method as described above, wherein the cell proliferation after inducing the expression is reduced by allowing the cells to sufficiently proliferate during a period before inducing the expression.

DESCRIPTION OF THE PREFERRED EMBODIMENTS

Figure 1:
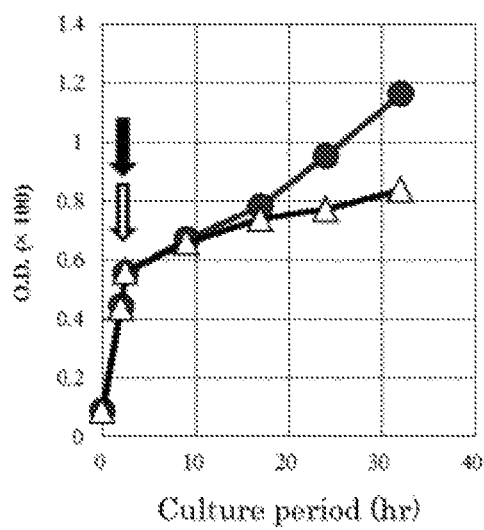
FIG. 1: Graph showing change of OD620 over time. The symbols ● indicate the results obtained with the control condition, and the symbols Δ indicate the results obtained with the organic nitrogen source-limited condition. The arrows indicate the time points at which an IPTG solution was added.
Figure 2A:
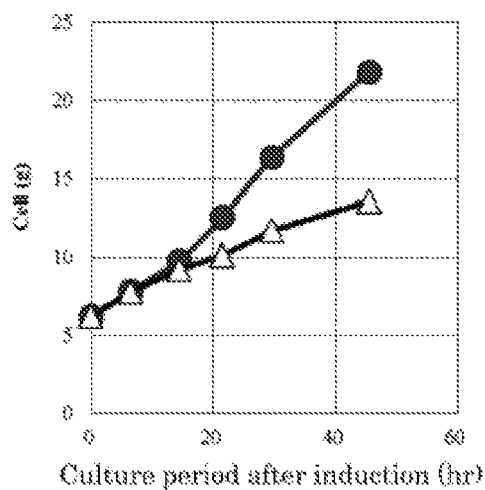
FIG. 2(A) to FIG. 2(D): Graphs showing the results concerning the cell proliferation after addition of an IPTG solution: (A) cell amount, (B) cell growth rate, (C) cell growth rate slope, and (D) cumulative specific proliferation rate. The symbols ● indicate the results obtained with the control condition, and the symbols Δ indicate the results obtained with the organic nitrogen source-limited condition.
Figure 2B:
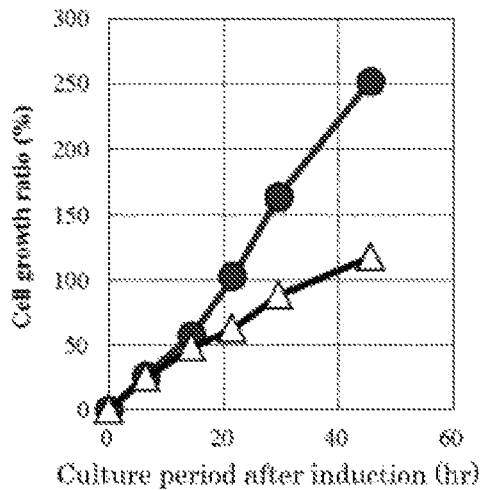
Figure 2C:
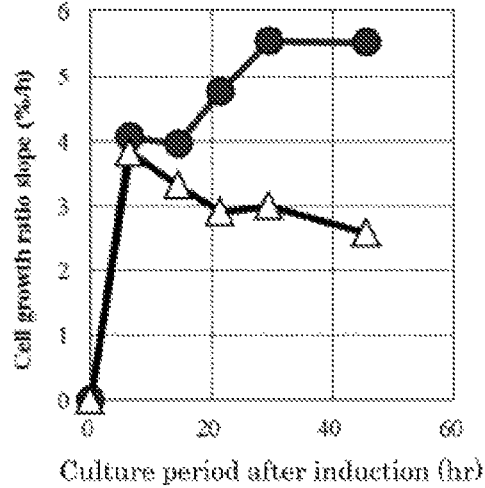
Figure 2D:
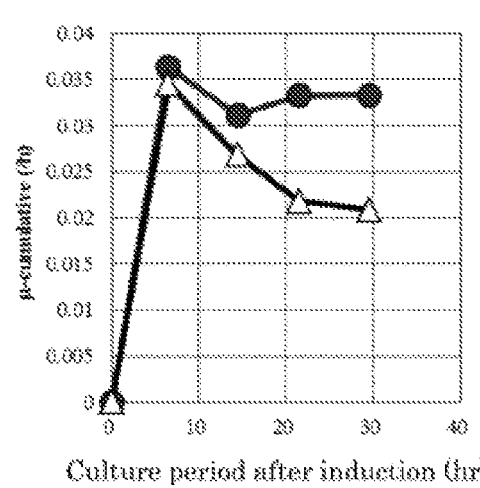

Hereafter, the present invention will be explained in detail.

<1> Fibroin-Like Protein

The term "fibroin-like protein" is a generic term referring to fibroin and a fibrous protein having a structure similar to that of fibroin.

The term "fibroin" refers to a fibrous protein that is a component of spider's thread or silkworm's thread. That is, examples of fibroin include spider fibroin, and silkworm fibroin. Species of spider, species of silkworm, and the type of thread are not particularly limited. Examples of spider species include *Araneus diadematus* and *Nephila clawpes*. Examples of spider fibroin include proteins of drag line, frame thread, and radius thread produced by major ampullate gland (major ampullate gland proteins), proteins of scaffolding thread produced by minor ampullate gland (minor ampullate gland proteins), and proteins of spiral line produced by flagelliform gland (flagelliform gland proteins). Specific examples of spider fibroin include, for example, the major ampullate gland proteins ADF3 and ADF4 of *Araneus diadematus* and the major ampullate gland proteins MaSp1 and MaSp2 of *Nephila clawpes*. Examples of silkworm species include *Bombyx mori* and *Samia cynthia*. The amino acid sequences of these fibroins and the nucleotide sequences of the genes encoding these fibroins, also referred to as "fibroin gene" can be obtained from public databases such as NCBI (ncbi.nlm.nih.gov/). The amino acid sequence of ADF3 of *Araneus diadematus* (partial; NCBI AAC47010.1 GI: 1263287) is shown as SEQ ID NO: 3. That is, the fibroin-like protein may be, for example, a protein having any of the amino acid sequences of fibroins disclosed in the aforementioned database (for example, SEQ ID NO: 3). A gene encoding a fibroin-like protein, also referred to as "fibroin-like protein gene" may be, for example, a gene having any of the nucleotide sequences of the fibroin genes disclosed in the aforementioned database. The expression "having an (amino acid or nucleotide) sequence" can include when a larger sequence includes the amino acid or nucleotide sequence, and when the amino acid or nucleotide sequence is not a part a larger sequence, but exists alone.

The term "fibrous protein having a structure similar to that of fibroin" can mean a fibrous protein having a sequence similar to a repetitive sequence of fibroin. The "sequence similar to a repetitive sequence of fibroin" may be a sequence actually found in fibroin, or may be a sequence similar to such a sequence. Examples of the fibrous protein having a structure similar to that of fibroin include polypeptides derived from the large spigot drag line proteins described in WO2012/165476 and recombinant spider silk proteins described in WO2006/008163.

Namely, examples of the "sequence similar to a repetitive sequence of fibroin" can include a sequence represented by the following formula I (WO2012/165476, henceforth also referred to as "repetitive sequence I"):

REP1–REP2 (I)

In the formula I, REP1 is an amino acid sequence that is continuous and includes alanine and/or glycine. When REP1 includes both alanine and glycine, the order of alanine and glycine is not particularly limited. For example, in REP1, alanine residues may be continuous and adjacent to each other, glycine residues may be continuous and adjacent to each other, or alanine and glycine residues may alternate. The length of REP1 may be, for example, 2 residues or longer, 3 residues or longer, 4 residues or longer, or 5 residues or longer, or may be 20 residues or shorter, 16 residues or shorter, 13 residues or shorter, 12 residues or shorter, or 8 residues or shorter, or may be within a range defined by any combination of these ranges. The length of REP1 may be, for example, 2 to 20 residues, 3 to 16 residues, 4 to 13 residues, 4 to 12 residues, or 5 to 8 residues. REP1 corresponds to, for example, the crystalline region of the spider fibroin that forms the crystalline β sheet within the fiber.

In the formula I, REP2 is an amino acid sequence that can include one or more of glycine, serine, glutamine, and alanine. In REP2, the total number of glycine, serine, glutamine, and alanine residues may be, for example, 40% or more, 60% or more, or 70% or more of the total number of amino acid residues of REP2. The length of REP2 may be, for example, 2 residues or longer, 10 residues or longer, or 20 residues or longer, or may be 200 residues or shorter, 150 residues or shorter, 100 residues or shorter, or 75 residues or shorter, or may be within a range defined by any combination of these ranges. The length of REP2 may be, for example, 2 to 200 residues, 10 to 150 residues, 20 to 100 residues, or 20 to 75 residues. REP2 corresponds to, for example, an amorphous region of the fibroin of spider showing flexibility, most part of which lacks regular structure.

The number of times the repetitive sequence I repeats is not particularly limited; and can be, for example, 2 or more, 5 or more, or 10 or more, or it can also be 100 or less, 50 or less, or 30 or less, and it may be within a range defined by any combination of these ranges. The configurations of REP1 and REP2 of the respective repetitive sequences may be or may not be the same.

The fibrous protein having a structure similar to that of fibroin can have, for example, an amino acid sequence having a homology of 90% or higher to an amino acid sequence around the C-terminus of the spider fibroin at the C-terminus, in addition to the sequence similar to the repetitive sequence of fibroin. Examples of the amino acid sequence around the C-terminus of the fibroin of spider include, for example, the amino acid sequence of the C-terminus 50 residues of the spider fibroin, the amino acid sequence of the C-terminus 50 residues of the same of which the C-terminus 20 residues are removed, and the amino acid sequence of the C-terminus 50 residues of the same of which the C-terminus 29 residues are removed. Specific examples of the amino acid sequence around the C-terminus of the spider fibroin include, for example, the sequence of the positions 587 to 636 (C-terminus 50 residues), the sequence of the positions 587 to 616, and the sequence of the positions 587 to 607 of ADF3 of *Araneus diadematus* (partial; NCBI AAC47010.1 GI: 1263287) shown as SEQ ID NO: 3.

Specific examples of the fibrous protein having a sequence similar to the repetitive sequence of fibroin, and having an amino acid sequence showing a homology of 90% or higher to an amino acid sequence around the C-terminus of the spider fibroin include, for example, a protein encoded by a gene having the nucleotide sequence of SEQ ID NO: 10 described in WO2012/165476A1. The nucleotide sequence of the gene is shown as SEQ ID NO: 1, and the amino acid sequence of the protein encoded by the gene is shown as SEQ ID NO: 2.

The fibroin-like protein may be a variant of any of the fibroin-like proteins exemplified above, that is, fibroin and the fibrous proteins having a structure similar to that of fibroin exemplified above, so long as the original function thereof is maintained. Similarly, the fibroin-like protein gene may be a variant of any of the fibroin-like protein genes exemplified above (that is, genes encoding fibroin and the fibrous proteins having a structure similar to that of fibroin exemplified above), so long as the original function thereof is maintained. Such variants that maintain the original function are also referred to as "conservative variants". Examples of the conservative variants include, for example, homologues and artificially-modified proteins or genes of the fibroin-like proteins exemplified above and genes encoding them.

The expression that "the original function is maintained" can mean that a variant of a gene or protein has a function, that is, activity and property, corresponding to the function, that is activity and property, of the original gene or protein. That is, in the case of the fibroin-like protein, the expression that "the original function is maintained" can mean that a variant of the protein is the fibrous protein. In the case of the fibroin-like protein gene, the expression that "the original function is maintained" means that a variant of the gene encodes a protein that maintains the original function (namely, the fibrous protein). The term "fibrous protein" refers to a protein that has a fibrous form under predetermined conditions. That is, the fibrous protein may be a protein expressed in a fibrous form, or a protein that is not in a fibrous form when it is expressed, but can be processed into a fibrous form. The fibrous protein may be, for example, a protein that is expressed as an inclusion body, and can be then processed into a fibrous form by an appropriate technique.

Examples of homologue of the fibroin-like protein include, for example, a protein obtained from a public database by BLAST search or FASTA search using any of the aforementioned amino acid sequences of fibroin-like proteins as a query sequence. A homologue of the aforementioned fibroin-like protein genes can be obtained by, for example, PCR using a chromosome of various microorganisms as the template, and oligonucleotides prepared on the basis of any of the aforementioned nucleotide sequences of fibroin-like protein genes as the primers.

Conservative variants of the fibroin-like protein and fibroin-like protein gene will be explained below.

The fibroin-like protein may be a protein having any of the aforementioned amino acid sequences of fibroin-like proteins including substitution, deletion, insertion, or addition of one or several amino acid residues at one or several positions, so long as the original function of the protein is maintained. Although the number meant by the term "one or several" can differ depending on the positions of amino acid residues in the three-dimensional structure of the protein, or the types of amino acid residues, it is specifically, for example, 1 to 50, 1 to 40, 1 to 30, 1 to 20, 1 to 10, 1 to 5, or 1 to 3.

The aforementioned substitution, deletion, insertion, or addition of one or several amino acid residues are each a conservative mutation that maintains the original function of the protein. Typical examples of the conservative mutation are conservative substitutions. The conservative substitution is a mutation wherein substitution takes place mutually among Phe, Trp, and Tyr, if the substitution site is an aromatic amino acid; among Leu, Ile, and Val, if it is a hydrophobic amino acid; between Gln and Asn, if it is a polar amino acid; among Lys, Arg, and His, if it is a basic amino acid; between Asp and Glu, if it is an acidic amino acid; and between Ser and Thr, if it is an amino acid having a hydroxyl group. Examples of substitutions considered as conservative substitutions include, specifically, substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp, or Arg for Gln, substitution of Gly, Asn, Gln, Lys, or Asp for Glu, substitution of Pro for Gly, substitution of Asn, Lys, Gln, Arg, or Tyr for His, substitution of Leu, Met, Val, or Phe for Ile, substitution of Ile, Met, Val, or Phe for Leu, substitution of Asn, Glu, Gln, His, or Arg for Lys, substitution of Ile, Leu, Val, or Phe for Met, substitution of Trp, Tyr, Met, Ile, or Leu for Phe, substitution of Thr or Ala for Ser, substitution of Ser or Ala for Thr, substitution of Phe or Tyr for Trp, substitution of His, Phe, or Trp for Tyr, and substitution of Met, Ile, or Leu for Val. Further, such substitution, deletion, insertion, addition, or the like of amino acid residues as mentioned above includes a naturally occurring mutation due to an individual difference, or a difference of species of the organism from which the gene is derived (mutant or variant).

The fibroin-like protein may be a protein having an amino acid sequence showing a homology of 80% or higher, 90% or higher, 95% or higher, 97% or higher, or 99% or higher, to any of the aforementioned amino acid sequences of fibroin-like proteins, so long as the original function is maintained. In this description, "homology" can also mean "identity".

The fibroin-like protein may be a protein encoded by a DNA that is able to hybridize under stringent conditions with a probe that can be prepared from any of the aforementioned nucleotide sequences of fibroin-like protein genes, such as a sequence complementary to the whole sequence or a partial sequence of any of the aforementioned nucleotide sequences, so long as the original function is maintained. Such a probe can be prepared by PCR using oligonucleotides prepared on the basis of any of the aforementioned nucleotide sequences as the primers, and a DNA fragment containing any of the aforementioned nucleotide sequences as the template. The "stringent conditions" refer to conditions under which a so-called specific hybrid is formed, and a non-specific hybrid is not formed. Examples of the stringent conditions include those under which highly homologous DNAs hybridize to each other, for example, DNAs not less than 50%, 65%, or 80% homologous, not less than 90% homologous, not less than 95% homologous, not less than 97% homologous, not less than 99% homologous, hybridize to each other, and DNAs less homologous than the above do not hybridize to each other, or conditions of washing of typical Southern hybridization, for example, conditions of washing once, or 2 or 3 times, at a salt concentration and temperature of 1×SSC, 0.1% SDS at 60° C., 0.1×SSC, 0.1% SDS at 60° C., or 0.1×SSC, 0.1% SDS at 68° C. Furthermore, for example, when a DNA fragment having a length of about 300 bp is used as the probe, the washing conditions of the hybridization can be, for example, 50° C., 2×SSC, and 0.1% SDS.

The fibroin-like protein may be a fusion protein with another peptide. The "another peptide" is not particularly limited so long as a fibroin-like protein having desired property can be obtained. The "another peptide" can be appropriately selected as required depending on various conditions such as purpose of use thereof. Examples of the "another peptide" include a peptide tag, and recognition sequence for a protease. The "another peptide" may be bound to, for example, the N-terminus or C-terminus, or the both of the fibroin-like protein. As the "another peptide", one kind of peptide may be used, or two or more kinds of peptides may be used in combination.

Specific examples of the peptide tag include an His tag, FLAG tag, GST tag, Myc tag, MBP (maltose binding protein), CBP (cellulose binding protein), TRX (thioredoxin), GFP (green fluorescent protein), HRP (horseradish peroxidase), ALP (alkaline phosphatase), and Fc region of antibody. The peptide tag can be used, for example, for detection and purification of the expressed fibroin-like protein.

Specific examples of the recognition sequence for a protease include the recognition sequence for the HRV3C protease, the recognition sequence for the factor Xa protease, and the recognition sequence for the proTEV protease. The recognition sequence for a protease can be used, for example, for cleavage of the expressed fibroin-like protein. Specifically, for example, when the fibroin-like protein is expressed as a fusion protein with a peptide tag, if a recognition sequence for a protease is introduced into a linking part between the fibroin-like protein and the peptide tag, the peptide tag can be removed from the expressed fibroin-like protein by using the protease to obtain the fibroin-like protein not having the peptide tag.

Specific examples of such a fusion protein include ADF3 of *Araneus diadematus* to which a His tag and the HRV3C protease recognition sequence have been added at the N-terminus (SEQ ID NO: 5). Examples of the nucleotide sequence encoding the fusion protein of SEQ ID NO: 5 include the nucleotide sequence of the positions 12 to 1994 of SEQ ID NO: 4.

The fibroin-like protein gene may have any of the nucleotide sequences of fibroin-like protein genes exemplified above and conservative variants thereof, in which arbitrary codons are replaced with equivalent codons. For example, the fibroin-like protein gene may be modified so that it has codons optimized for codon usage in the chosen host.

<2> Bacterium of the Present Invention

The bacterium is *Escherichia coli* having a gene encoding a fibroin-like protein.

The bacterium has a fibroin-like protein gene, and therefore has an ability to produce a fibroin-like protein (fibroin-like protein-producing ability). The expression that "the bacterium has a fibroin-like protein-producing ability" means that, for example, when the bacterium is cultured in a medium, it produces and accumulates a fibroin-like protein in the medium and/or cells thereof to such an extent that the fibroin-like protein can be collected from the medium and/or cells.

The chosen species/strains of *Escherichia coli* is not particularly limited, and examples thereof include bacteria classified as *Escherichia coli* according to the taxonomy known to those skilled in the field of microbiology. Specific examples of strains of *Escherichia coli* include, for example, *Escherichia coli* K-12 strains such as W3110 (ATCC 27325) and MG1655 (ATCC 47076); *Escherichia coli* K5 (ATCC 23506); *Escherichia coli* B strains such as BL21(DE3) and BLR(DE3), which is an recA⁻ strain of the former; and derivative strains of these.

These strains are available from, for example, the American Type Culture Collection (Address: P.O. Box 1549, Manassas, Va. 20108, United States of America). That is, registration numbers are given to the respective strains, and the strains can be ordered by using these registration numbers (refer to atcc.org/). The registration numbers of the strains are listed in the catalogue of the American Type Culture Collection. The BL21(DE3) strain is available from, for example, Life Technologies (product number C6000-03). The BLR(DE3) strain is available from, for example, Merck Millipore (product number 69053).

The bacterium may be an auxotrophic strain. Such an auxotrophic strain may have one kind of auxotrophy, or may have two or more kinds of auxotrophies. Examples of the auxotrophy include amino acid auxotrophy such as isoleucine auxotrophy, and nucleic acid auxotrophy. For example, the *Escherichia coli* BLR(DE3) strain shows isoleucine auxotrophy (Schmidt M., Romer L., Strehle M., Scheibel T., Biotechnol. Lett., 2007, 29 (11):1741-1744).

An *Escherichia coli* strain having a fibroin-like protein gene can be obtained by introducing the gene into any of the *Escherichia coli* strains as mentioned above. *Escherichia coli* strains that will be transformed with a fibroin-like protein gene and *Escherichia coli* strains that have been transformed with a fibroin-like protein gene are henceforth also generically referred to as "host".

A fibroin-like protein gene can be obtained by cloning from an organism having the fibroin-like protein gene. For the cloning, a nucleic acid such as genomic DNA or cDNA containing the gene can be used. A fibroin-like protein gene can also be obtained by chemical synthesis (Gene, 60(1), 115-127 (1987)).

By appropriately modifying the obtained fibroin-like protein gene, a variant thereof can also be obtained. The gene can be modified by a known technique. For example, an objective mutation can be introduced into a target site of DNA by the site-specific mutation method. That is, for example, a coding region of a gene can be modified by site-specific mutagenesis so that at a specific site in the encoded protein, one or more amino acids is/are substituted, deleted, inserted, or added. Examples of site-specific mutagenesis include using PCR (Higuchi, R., 61, in PCR Technology, Erlich, H. A. Eds., Stockton Press (1989); Carter P., Meth., in Enzymol., 154, 382 (1987)), and using a phage (Kramer, W. and Frits, H. J., Meth. in Enzymol., 154, 350 (1987); Kunkel, T. A. et al., Meth. in Enzymol., 154, 367 (1987)).

The method for introducing a fibroin-like protein gene into a host is not particularly limited. In the host, a fibroin-like protein gene may be harbored in such a manner that it can be expressed under control of a promoter that functions in the host. In the host, a fibroin-like protein gene may be present on a vector autonomously replicable out of the chromosome such as plasmid, cosmid, or phagemid, or may be introduced into the chromosome. The host may have only one copy of a fibroin-like protein gene, or may have two or more copies of a fibroin-like protein gene. The host may have only one kind of fibroin-like protein gene, or may have two or more kinds of fibroin-like protein genes.

The promoter for expressing a fibroin-like protein gene is not particularly limited so long as the promoter is a promoter that functions and is inducible in the host. The "promoter that functions and is inducible in a host" refers to a promoter that shows a promoter activity inducible in the host. The promoter may be a promoter derived from, or native to, the host, or a heterogeneous promoter. Examples of promoter that functions and is inducible in *Escherichia coli* include, for example, directly inducible promoters such as lac promoter, trc promoter, tac promoter, trp promoter, araBAD promoter, tetA promoter, rhaP$_{BAD}$ promoter, proU promoter, cspA promoter, $\lambda P_L$ promoter, $\lambda P_R$ promoter, phoA promoter, and pstS promoter, and indirectly inducible promoters such as T3 promoter, T5 promoter, T7 promoter, and SP6 promoter. Gene expression from the lac promoter, trc promoter, or tac promoter can be induced with isopropyl-β-D-thiogalactopyranoside (IPTG) or lactose. Gene expression from the trp promoter can be induced with 3-β-indole acrylate (IAA). Gene expression from the araBAD promoter can be induced with L-arabinose. Gene expression from the tetA promoter can be induced with anhydrotetracycline. Gene expression from the rhaP$_{BAD}$ promoter can be induced with L-rhamnose. Gene expression from the proU promoter can be induced with NaCl. Gene expression from the trp promoter can also be induced by making tryptophan in the medium depleted. Gene expression from the cspA promoter can be induced with low temperature conditions. Gene expression from the λP$_L$ promoter or λP$_R$ promoter can be induced with high temperature conditions. Gene expression from the phoA promoter or pstS promoter can be induced by making phosphate in the medium depleted. Transcription of a gene from the T3 promoter, T5 promoter, T7 promoter, or SP6 promoter is attained with phage T3 RNA polymerase, T5 RNA polymerase, T7 RNA polymerase, or SP6 RNA polymerase, respectively. Therefore, gene expression from the T3 promoter, T5 promoter, T7 promoter, or SP6 promoter can be indirectly induced by inducing expression of a corresponding RNA polymerase under control of such a directly inducible promoter as mentioned above. The aforementioned promoters may be used as they are, or they may be used after being appropriately modified. For example, a highly-active type of such promoters as mentioned above may also be obtained by using various reporter genes, and used. For example, by making the −35 and −10 regions in a promoter region closer to a consensus sequence, the activity of the promoter can be enhanced (WO00/18935). Examples of the highly-active type promoter include various tac-like promoters (Katashkina J I et al., Russian Federation Patent Application No. 2006134574), and the pnlp8 promoter (WO2010/027045). Methods for evaluating the strength of promoters and examples of strong promoters are described in the paper of Goldstein et al. (Prokaryotic Promoters in Biotechnology, Biotechnol. Annu. Rev., 1, 105-128 (1995)), and so forth.

A fibroin-like protein gene can be introduced into a host by, for example, using a vector containing the gene. A vector containing a fibroin-like protein gene is also referred to a recombinant DNA of a fibroin-like protein gene. The recombinant DNA of a fibroin-like protein gene can be constructed by, for example, ligating a DNA fragment containing the fibroin-like protein gene with a vector that functions in a host. By transforming the host with the recombinant DNA of a fibroin-like protein gene, a transformant harboring the recombinant DNA is obtained, namely, the gene can be introduced into the host. As the vector, a vector autonomously replicable in the host cell can be used. The vector can be a multi-copy vector. Furthermore, the vector can have a marker such as an antibiotic resistance gene for selection of the transformant. The vector may also contain an inducible promoter for expression of an inserted gene that functions in *Escherichia coli*. The vector may be, for example, a vector derived from a bacterial plasmid, vector derived from a yeast plasmid, vector derived from a bacteriophage, cosmid, phagemid, or the like. Specific examples of vector autonomously replicable in *Escherichia coli* include, for example, pUC19, pUC18, pHSG299, pHSG399, pHSG398, pBR322, pSTV29 (all of these are available from Takara Bio), pACYC184, pMW219 (NIPPON GENE), pTrc99A (Pharmacia), pPROK series vectors (Clontech), pKK233-2 (Clontech), pET series vectors (Novagen), pQE series vectors (QIAGEN), pCold TF DNA (TaKaRa), pACYC, and broad host spectrum vector RSF1010. When such a recombinant DNA is constructed, for example, a coding region of a fibroin-like protein ligated downstream from any one of such promoters as mentioned above may be incorporated into a vector, or a coding region of a fibroin-like protein may be incorporated into a vector downstream from a promoter originally present in the vector.

A fibroin-like protein gene can also be introduced into, for example, a chromosome of a host. A gene can be introduced into a chromosome, for example, by using homologous recombination (Miller, J. H., Experiments in Molecular Genetics, 1972, Cold Spring Harbor Laboratory). Examples of gene transfer method utilizing homologous recombination include, for example, a method of using a linear DNA such as Red-driven integration (Datsenko, K. A., and Wanner, B. L., Proc. Natl. Acad. Sci. USA, 97:6640-6645 (2000)), a method of using a plasmid containing a temperature sensitive replication origin, a method of using a plasmid capable of conjugative transfer, a method of using a suicide vector not having a replication origin that functions in a host, and a transduction method using a phage. Only one copy of the gene may be introduced, or two or more copies of the gene may be introduced. For example, by performing homologous recombination using a sequence which is present in multiple copies on a chromosome as a target, multiple copies of a gene can be introduced into the chromosome. Examples of such a sequence which is present in multiple copies on a chromosome include repetitive DNAs, and inverted repeats located at the both ends of a transposon. Homologous recombination may also be performed by using an appropriate sequence on a chromosome such as a gene unnecessary for carrying out the present invention as a target. Furthermore, a gene can also be randomly introduced into a chromosome by using a transposon or Mini-Mu (Japanese Patent Laid-open (Kokai) No. 2-109985, U.S. Pat. No. 5,882,888, EP 805867 B1). When the gene is introduced into a chromosome, for example, a coding region of a fibroin-like protein ligated downstream from any of such promoters as mentioned above may be incorporated into a chromosome, or a coding region of a fibroin-like protein may be incorporated into a chromosome downstream from a promoter originally present on the chromosome.

Introduction of a gene into a chromosome can be confirmed by, for example, Southern hybridization using a probe having a sequence complementary to the entire gene or a part thereof, or PCR using primers prepared on the basis of the nucleotide sequence of the gene.

The method for the transformation is not particularly limited, and conventionally known methods can be used. Examples of transformation methods include, for example, a method of treating recipient cells with calcium chloride so as to increase permeability thereof for DNA, which has been reported for the *Escherichia coli* K-12 strain (Mandel, M. and Higa, A., J. Mol. Biol., 1970, 53, 159-162), a method of preparing competent cells from cells which are in the growth phase, followed by introducing DNA, which has been reported for *Bacillus subtilis* (Duncan, C. H., Wilson, G. A. and Young, F. E., 1977, Gene, 1:153-167), and so forth. Alternatively, another transformation method includes making DNA-recipient cells into protoplasts or spheroplasts, which can easily take up recombinant DNA, and then introducing a recombinant DNA into the DNA-recipient cells, which is known to be applicable to *Bacillus subtilis*, actinomycetes, and yeasts (Chang, S. and Choen, S. N., 1979, Mol. Gen. Genet., 168:111-115; Bibb, M. J., Ward, J. M. and Hopwood, O. A., 1978, Nature, 274:398-400; Hinnen, A., Hicks, J. B. and Fink, G. R., 1978, Proc. Natl. Acad. Sci. USA, 75:1929-1933). Furthermore, the electric pulse transformation method has been reported for transforming coryneform bacteria (Japanese Patent Laid-open (Kokai) No. 2-207791).

<3> Method of the Present Invention

The method of the present invention is a method for producing a fibroin-like protein by culturing *Escherichia coli* having a gene encoding the fibroin-like protein in a medium, inducing expression of the gene encoding the fibroin-like protein, and collecting the fibroin-like protein, wherein cell proliferation after inducing the expression is reduced.

That is, first, culture of the bacterium is started. Expression of the fibroin-like protein gene is induced at an appropriate time after the start of the culture. After the induction of the expression, the culture is further continued so that the bacterium produces and accumulates a fibroin-like protein in the medium and/or cells of the bacterium. The term "time of inducing the expression" refers to the time of performing the induction of the expression, namely, the time of inducing the expression of a fibroin-like protein gene. The period from the start of the culture to the induction of the expression is also referred to as "period before inducing the expression", and the period from the induction of the expression to the end of the culture is also referred to as "period after inducing the expression".

By the induction of the expression, the expression amount of the fibroin-like protein gene increases compared with that observed under a normal condition. By the induction of the expression, the expression amount of the fibroin-like protein gene may increase at least 2 times or more, 3 times or more, or 4 times or more, compared with that observed under a normal condition. The term "normal condition" refers to conditions under which the fibroin-like protein gene is expressed under control of a non-inducible promoter, or conditions under which the induction of the amount of expression appropriate for chosen expression system does not occur. Examples of the "conditions under which the fibroin-like protein gene is expressed under control of a non-inducible promoter" include when the fibroin-like protein gene is expressed under control of a native non-inducible promoter of the gene. Examples of the "conditions under which the induction of the amount of expression appropriate for the chosen expression system do not occur" include, when the expression is induced by the presence of a certain substance, and that the substance is not added; when the expression is induced by depletion of a certain substance, and that substance is not depleted; and when the expression is induced at a certain temperature, and that temperature of the culture system is outside the temperature range in which the expression is induced.

Culture conditions are not particularly limited, so long as the bacterium=can proliferate during the period before inducing the expression, cell proliferation during a period after inducing the expression is reduced, and a fibroin-like protein is produced and accumulated during the period after inducing the expression. During the period after inducing the expression, the bacterium may proliferate, or may not proliferate. The culture conditions for the period before inducing the expression and the period after inducing the expression may be the same, or may not be the same. The culture conditions can be appropriately selected by those skilled in the art according to various conditions such as type of the method for reducing cell proliferation.

The length of "the period before inducing the expression", i.e., the timing for inducing the expression, can be appropriately chosen according to various conditions such as culture conditions. For example, the induction of the expression may be performed at a time point on or after 0 hour, 1 hour, 2 hours, or 3 hours after the start of the culture, or at a time point on or before 240 hours, 200 hours, 160 hours, 120 hours, or 80 hours after the start of the culture, or at a time point within a period defined by any combination of these earliest and latest time points. The induction of the expression may also be performed, for example, when OD620 of the culture medium becomes 40 to 500, 40 to 400, 40 to 300, or 40 to 200. The length of "the period after inducing the expression" can be appropriately chosen according to various conditions such as culture conditions. Culture period after inducing the expression may be, for example, 1 hour or longer, 4 hours or longer, or 8 hours or longer, or may be 240 hours or shorter, 200 hours or shorter, 160 hours or shorter, 120 hours or shorter, or 80 hours or shorter, or may be within a range defined by any combination of these ranges.

The induction of the expression can be performed according to the requirements of the chosen expression system. Namely, the expression of a fibroin-like protein can be induced by adding, to the medium, for example, isopropyl-β-D-thiogalactopyranoside (IPTG) or lactose when the lac promoter, trc promoter, or tac promoter is used; 3-β-indole acrylate (IAA) when the trp promoter is used; L-arabinose when the araBAD promoter is used; anhydrotetracycline when the tetA promoter is used; L-rhamnose when the rhaP$_{BAD}$ promoter is used; or NaCl when the proU promoter is used. The expression of a fibroin-like protein can also be induced by, for example, depleting tryptophan in the medium when the trp promoter is used. The expression of a fibroin-like protein can also be induced by, for example, lowering the temperature of the medium, for example, lowering the temperature to about 15° C., when the cspA promoter is used. The expression of a fibroin-like protein can also be induced by, for example, elevating the temperature of the medium, for example, elevating the temperature to 42° C., when the λP$_L$ promoter or λP$_R$ promoter is used. The expression of a fibroin-like protein can also be induced by, for example, depleting phosphate in the medium when the phoA promoter or pstS promoter is used. When the T3 promoter, T5 promoter, T7 promoter, or SP6 promoter is used, the expression of a fibroin-like protein can also be induced by, for example, appropriately inducing expression of a corresponding RNA polymerase. Furthermore, for example, also when such promoters as mentioned above are modified as required and used, conditions for the induction of the expression can be appropriately chosen. Depending on the configuration of the expression system, two or more kinds of expression induction conditions may be used in combination.

As the medium, for example, media typically used for culture of bacteria such as *Escherichia coli* can be used as is, or after appropriate modification. As the medium, for example, a liquid medium containing a carbon source, nitrogen source, phosphate source, sulfur source, and ingredients such as other various organic and inorganic ingredients as required can be used. Types and concentrations of the medium components may be appropriately chosen by those skilled in the art.

Specific examples of the carbon source include, for example, saccharides such as glucose, fructose, sucrose, lactose, galactose, xylose, arabinose, blackstrap molasses, hydrolysate of starch, and hydrolysate of biomass, organic acids such as acetic acid, fumaric acid, citric acid, succinic acid, and malic acid, alcohols such as glycerol, crude glycerol, and ethanol, and aliphatic acids. As the carbon source, one kind of carbon source may be used, or two or more kinds of carbon sources may be used in combination. Among these, carbon sources other than organic acids can be used, including saccharides and glucose. The ratio of glucose in the total carbon source may be, for example, 50% (w/w) or higher, 70% (w/w) or higher, 90% (w/w) or higher, 95% (w/w) or higher, or 100% (w/w).

Specific examples of the nitrogen source include, for example, ammonium salts such as ammonium sulfate, ammonium chloride, and ammonium phosphate, organic nitrogen sources such as peptone, yeast extract, meat extract, and soybean protein decomposition product, ammonia, and urea. As the nitrogen source, one kind of nitrogen source may be used, or two or more kinds of nitrogen sources may be used in combination.

Specific examples of the phosphate source include, for example, phosphate salts such as potassium dihydrogenphosphate and dipotassium hydrogenphosphate, and phosphoric acid polymers such as pyrophosphoric acid. As the phosphate source, one kind of phosphate source may be used, or two or more kinds of phosphate sources may be used in combination.

Specific examples of the sulfur source include, for example, inorganic sulfur compounds such as sulfates, thiosulfates, and sulfites, and sulfur-containing amino acids such as cysteine, cystine, and glutathione. As the sulfur source, one kind of sulfur source may be used, or two or more kinds of sulfur sources may be used in combination.

Specific examples of the other various organic and inorganic components include, for example, inorganic salts such as sodium chloride, and potassium chloride; trace metals such as iron, manganese, magnesium, and calcium; vitamins such as vitamin B1, vitamin B2, vitamin B6, nicotinic acid, nicotinamide, and vitamin B12; amino acids; nucleic acids; and organic components containing these such as peptone, casamino acid, yeast extract, and soybean protein decomposition product. As the other various organic and inorganic components, one kind of component may be used, or two or more kinds of components may be used in combination.

When an auxotrophic strain that requires a nutrient such as one or more amino acids for growth, the required nutrient can be added to the medium. When a gene is introduced by using a vector carrying an antibiotic resistance gene, the corresponding antibiotic can be added to the medium.

The culture can be aerobically performed by, for example, aeration or shaking. The oxygen concentration may be adjusted to, for example, 5 to 50%, or 20 to 40%, of the saturated dissolved oxygen concentration. The culture temperature may be, for example, 20 to 45° C., 25 to 40° C., or 30 to 37° C. The pH of the medium may be 5 to 9 during the culture. To adjust the pH, inorganic or organic acidic or alkaline substances such as calcium carbonate, ammonia gas, and aqueous ammonia can be used. The culture can be performed as batch culture, fed-batch culture, continuous culture, or a combination of these. The medium used at the time of the start of the culture is also referred to as "starting medium". The medium supplied to a culture system, or a fermentation tank used in fed-batch culture or continuous culture is also referred to as "feed medium". To supply a feed medium to a culture system used in fed-batch culture or continuous culture is also referred to as to "feed". The culture may also be performed as separate pre-culture and main culture. The pre-culture may be performed by using, for example, a plate medium or liquid medium.

Each of the medium components may be contained in the starting medium, feed medium, or both. The components in the starting medium may be or may not be the same as those in the feed medium. The concentrations of the components in the starting medium may be or may not be the same as the concentrations of those in the feed medium. Furthermore, two or more kinds of feed media containing components of different types and/or different concentrations may be used. For example, when feeding is intermittently performed two or more times, types and/or concentrations of components contained in the respective feed media may be or may not be the same.

The method of the present invention is characterized in that cell proliferation after inducing the expression of a fibroin-like protein is reduced. The expression that "cell proliferation is reduced" means that the value of a parameter that indicates the degree of cell proliferation is smaller than that observed under control conditions, and may also mean that the cells do not proliferate at all. The term "parameter that indicates the degree of cell proliferation" refers to the cell growth rate, cell growth rate slope, cumulative specific proliferation rate (μ cumulative), or a combination of these. The expression that "cell proliferation is reduced" may mean that, for example, the value of a parameter that indicates the degree of cell proliferation is 95% or less, 90% or less, 80% or less, 70% or less, or 50% or less of the value of the parameter observed under the control conditions. The expression that "cell proliferation is reduced" may also mean that, for example, the cumulative specific proliferation rate is 0.070 (/h) or lower, 0.050 (/h) or lower, 0.030 (/h) or lower, 0.025 (/h) or lower, 0.020 (/h) or lower, or 0.015 (/h) or lower, at the time point at which accumulation of the fibroin-like protein stops. The expression that "cell proliferation is reduced" may also mean that, for example, the cell growth rate slope is 4.0 (%/h) or smaller, 3.5 (%/h) or smaller, 3.0 (%/h) or smaller, or 2.5 (%/h) or smaller, at the time point at which accumulation of the fibroin-like protein stops. The expression that "cell proliferation is reduced" may also mean that, for example, the cell growth rate is 80% or lower, 70% or lower, 60% or lower, or 50% or lower, at the time point at which accumulation of the fibroin-like protein stops. The term "time point at which accumulation of the fibroin-like protein stops" will be explained later. Cell proliferation may be reduced over the entire period of the period after inducing the expression, or during only a partial period of the period after inducing the expression. The length of the "partial period" is not particularly limited so long as production of the fibroin-like protein is improved compared with that observed under the control conditions. The term "partial period" may refer to, for example, a period of 50% or more, 70% or more, 90% or more, or 95% or more of the entire period of the period after inducing the expression.

The cumulative specific proliferation rate (μ cumulative) is calculated in accordance with the following equation.

$$\text{Cumulative specific proliferation rate}(/h) = (Xt - X0)/\int Xt\,dt = \ln(Xt/X0)/t$$

t: Time after start of induction (h)
Xt: Cell amount observed at t hours after start of induction
∫Xtdt: Integrated cell amount from start of induction to t hours after start of induction (g·h)

The cell growth rate is calculated in accordance with the following equation.

$$\text{Cell growth rate } (\%) = (Xt - X0)/X0 \times 100$$

Xt: Cell amount observed at t hours after start of induction (g)
X0: Cell amount observed at the time of start of induction (g)

The cell growth rate slope is calculated in accordance with the following equation.

$$\text{Cell growth rate slope (\%/h)} = (Xt - X0)/X0 \times 100/t$$

t: Time after start of induction (h)
Xt: Cell amount observed at t hours after start of induction (g)
X0: Cell amount observed at the time of start of induction (g)

The term "control conditions" refers to conditions under which cell proliferation after inducing the expression is not reduced. Examples of the "control conditions" include, conditions that cell proliferation after inducing the expression is reduced by growth factor limitation, conditions that the culture is aerobically performed in the presence of a sufficient amount of a growth factor, such as the control conditions described in Examples 1, 2, and 4. Examples of the "control conditions" also include, conditions that cell proliferation after inducing the expression is reduced by allowing the cells to sufficiently proliferate in the period before inducing the expression, conditions that the induction of the expression is performed before the cells sufficiently proliferate, such as the control conditions described in Example 3.

The expression that "production of the fibroin-like protein is improved compared with that observed under control conditions" means that the value of a parameter that indicates the amount of the fibroin-like protein produced is larger than that observed under the control conditions. The term "parameter that indicates the amount of the fibroin-like protein produced" refers to the accumulation amount of the fibroin-like protein relative to medium volume, the accumulation amount of the fibroin-like protein relative to cell weight, the cumulative productivity of the fibroin-like protein, or a combination of these. The expression that "production of the fibroin-like protein is improved compared with that observed under control conditions" may mean that, for example, the value of a parameter that indicates the productivity of the fibroin-like protein is 1.1 times or more, 1.2 times or more, 1.3 times or more, 1.4 times or more, or 1.5 times or more of that observed under the control conditions. The value of a parameter that indicates the amount of fibroin-like protein produced may be larger than that observed under the control conditions in terms of, for example, the value observed at a predetermined time point during the period after inducing the expression, or the maximum value observed during the period after inducing the expression. The "predetermined time point" can be appropriately chosen depending on various conditions such as culture conditions. The term "predetermined time point" may refer to, for example, the time point at which accumulation of the fibroin-like protein stops. The term "time point at which accumulation of the fibroin-like protein stops" may refer to, for example, a time point at which increase ratio of the accumulation amount of the fibroin-like protein relative to cell weight becomes 10% or lower per 4 to 12 hours. The term "time point at which accumulation of the fibroin-like protein stops" may also refer to, for example, 4 hours, 9 hours, 14 hours, 21.5 hours, 30 hours, 50 hours, 70 hours, or 100 hours after the induction of the expression, although it changes depending on the culture conditions.

The cumulative amount of fibroin-like protein produced from the time of inducing the expression to a predetermined time point is calculated in accordance with the following equation.

$$\text{Cumulative amount produced} = F/V/(T_1 - T_0)$$

F: Accumulation amount of fibroin-like protein (g)
V: Volume of medium (L)
$T_1$: Sampling time (predetermined time point)
$T_0$: Time of inducing expression The method for reducing cell proliferation after inducing the expression is not particularly limited.

The cell proliferation after inducing the expression can be reduced by, for example, performing the culture under limitation of a growth factor (growth factor limitation) during the period after inducing the expression. The term "growth factor" means an ingredient required for growth of cells. In general, examples of the growth factor include carbon source, nitrogen source, phosphate source, sulfur source, and minerals. As the nitrogen source, for example, an organic nitrogen source may be limited. When the bacterium is an auxotrophic strain, examples of the growth factor also include a nutrient required because of the auxotrophy. Examples of such a nutrient include amino acids such as isoleucine, and nucleic acids. The growth factor limitation can be performed, for example, under a condition that essential ingredients other than the ingredient to be limited are present or supplied in sufficient amounts. That is, for example, the phosphate source can be limited under a condition that the carbon source, nitrogen source, sulfur source, and minerals are supplied in sufficient amounts. In the method of the present invention, one kind of growth factor may be limited, or two or more kinds of growth factors may be limited.

The term "growth factor limitation" means that supply of a growth factor to a culture system is limited. By the growth factor limitation, the concentration of the growth factor in the culture system may be maintained to be low. That is, the term "growth factor limitation" may mean that, for example, the concentration of a growth factor in a medium is limited to be a certain concentration or lower. The value of the "certain concentration" is not particularly limited so long as production of the fibroin-like protein is improved compared with that observed under the control conditions. The value of "certain concentration" can be appropriately chosen according to various conditions such as type of the growth factor to be limited. Specifically, when the phosphate source is limited, the concentration of the phosphate source in the medium may be limited to be, for example, lower than 0.5 g/L, lower than 0.3 g/L, lower than 0.2 g/L, lower than 0.1 g/L, or 0 (zero), in terms of $KH_2PO_4$ amount. The concentration of the growth factor may be limited to be a certain concentration or lower over the entire period of the period after inducing the expression, or during only a partial period of the period after inducing the expression. The length of the "partial period" is not particularly limited so long as production of the fibroin-like protein is improved compared with that observed under the control conditions. The term "partial period" may refer to, for example, a period of 50% or more, 70% or more, 90% or more, or 95% or more of the entire period of the period after inducing the expression. The concentration of the growth factor may be or may not be constant over the entire period of the period after inducing the expression.

The growth factor limitation can be attained by, for example, reducing the concentration of the growth factor in the starting medium, reducing the feeding amount of the growth factor, or combination of them.

That is, for example, by reducing the concentration of the growth factor in the starting medium, the growth factor limitation can be attained for the period after inducing the expression. The term "starting medium" may be the "medium at the time of the start of the culture". Specifically, the term "medium at the time of the start of the culture" may refer to the culture medium immediately after inoculation. The concentration of the growth factor in the starting medium is not particularly limited so long as the growth factor limitation can be performed during the period after inducing the expression. The concentration of the growth factor in the starting medium may be, or may not be lower than a certain concentration. That is, even if the concentration of the growth factor in the starting medium is higher than the certain concentration, it is sufficient that the growth factor in the starting medium is consumed during the culture and thereby the concentration of the growth factor becomes the certain concentration or lower. The concentration of the growth factor in the starting medium can be chosen to be, for example, such a concentration that the growth factor is depleted during the culture. By performing the culture with a starting medium containing the growth factor at such a concentration that the growth factor is depleted during the culture, the cell proliferation after depletion of the growth factor can be reduced compared with that observed in the case where the growth factor is not depleted. The timing of the depletion is not particularly limited so long as cell proliferation after inducing the expression can be reduced. The growth factor may be depleted before or after inducing the expression. After the depletion, the culture can be continued as it is. The growth factor may also be appropriately fed before and/or after the depletion. For example, by feeding the growth factor, the timing of the depletion can be delayed, or cell proliferation can be restarted after the depletion. The concentration of the growth factor in the starting medium can be appropriately chosen according to various conditions, such as type of the growth factor and culture conditions. Specifically, when the organic nitrogen source is limited, the concentration of the organic nitrogen source in the starting medium may be, for example, 50 g/L or lower, 30 g/L or lower, 20 g/L or lower, 10 g/L or lower, 5 g/L or lower, 2 g/L or lower, or 1 g/L or lower. Also, specifically, when the phosphate source is limited, the concentration of the phosphate source in the starting medium in terms of $KH_2PO_4$ amount may be, for example, 50 g/L or lower, 30 g/L or lower, 20 g/L or lower, 10 g/L or lower, 5 g/L or lower, 3.5 g/L or lower, 3.0 g/L or lower, 2.5 g/L or lower, 2.0 g/L or lower, 1.5 g/L or lower, 1.0 g/L or lower, or 0.5 g/L or lower. Although such a reduction of the concentration of the growth factor in the starting medium may be performed for any growth factor, it can be performed for the phosphate source such as inorganic phosphate.

When the growth factor limitation is performed by reducing the concentration of the growth factor in the starting medium, culture procedures during the period before inducing the expression and the period after inducing the expression are not particularly limited so long as the growth factor limitation can be attained during the period after inducing the expression. That is, for example, whether the growth factor is fed or not, or the procedures of the feeding of the growth factor during the period before inducing the expression and the period after inducing the expression can be appropriately chosen so that the growth factor limitation can be attained in the period after inducing the expression. Specifically, for example, when a feed medium is fed during the period after inducing the expression, the concentration of the growth factor in the feed medium, or the feeding rate of the feed medium may be set to such a concentration of the growth factor in the feed medium, or feeding rate of the feed medium for performing the growth factor limitation by reducing the feeding amount of the growth factor during the period after inducing the expression as described later.

Also, for example, the growth factor limitation can be attained during the period after inducing the expression by reducing the feeding amount of the growth factor. Specifically, for example, when the feed medium is fed during the period after inducing the expression, by reducing the feeding amount of the growth factor during the period after inducing the expression, the growth factor limitation can be attained during the period after inducing the expression. The feeding amount of the growth factor is not particularly limited so long as the growth factor limitation can be performed in the period after inducing the expression. The expression that "reducing the feeding amount of the growth factor" may also mean that the growth factor is not fed. The feeding amount of the growth factor may be reduced over the entire period of the period after inducing the expression, or during only a partial period of the period after inducing the expression. The length of the "partial period" is not particularly limited so long as production of the fibroin-like protein is improved compared with that observed under the control conditions. The term "partial period" may refer to, for example, a period of 50% or more, 70% or more, 90% or more, or 95% or more of the entire period of the period after inducing the expression. The feeding amount of the growth factor can be reduced by reducing the concentration of the growth factor in the feed medium, reducing the feeding volume of the feed medium, or a combination of them. For example, by increasing the ratio of ingredient(s) other than the growth factor with respect to all the ingredients in the feed medium, the feeding amount of the growth factor can be reduced. For example, when the organic nitrogen source or phosphate source is limited, examples of the ingredient(s) other than the growth factor include the carbon source. The ratio of the ingredient(s) other than the growth factor with respect to all the ingredients in the feed medium may be, for example, 70% (w/w) or higher, 80% (w/w) or higher, 90% (w/w) or higher, 95% (w/w) or higher, or 100% (w/w). The ratio of the growth factor with respect to all the ingredients in the feed medium may be, for example, lower than 30% (w/w), lower than 20% (w/w), lower than 10% (w/w), lower than 5% (w/w), or 0 (zero). Specifically, when the phosphate source is limited, the ratio of the phosphate source with respect to all the ingredients in the feed medium may be, for example, lower than 2.5% (w/w), lower than 1.5% (w/w), lower than 1.0% (w/w), lower than 0.5% (w/w), or 0 (zero), in terms of the $KH_2PO_4$ amount.

The concentration of the growth factor in the feed medium and the feeding rate of the feed medium may be chosen so that, for example, the cumulative specific carbon source consumption rate (v cumulative) after inducing the expression is 0.35 g/g/hr or lower, 0.30 g/g/hr or lower, or 0.25 g/g/hr or lower. The cumulative specific carbon source consumption rate is calculated from the feeding rate of the carbon source (determined from the concentration of the carbon source in the feed medium, and the feeding rate of the feed medium), and the cell density in the medium. The carbon source may be, for example, glucose. The cumulative specific carbon source consumption rate from the induction of the expression to a predetermined time point is calculated in accordance with the following equation.

Cumulative specific carbon source consumption rate $(g/(g \cdot h)) = St / \int Xt dt$ t: Time after start of induction (h)
St: Consumption amount of carbon source from start of induction to t hours after start of induction (g)
∫Xtdt: Integrated cell amount from start of induction to t hours after start of induction (g·h)

The feed medium may be fed so that the concentration of the growth factor in the medium is maintained to be a certain concentration or lower. The concentration of the growth factor in the medium can be maintained to be a certain concentration or lower by, for example, feeding the feed medium so that the supply rate (feeding rate) of the growth factor to the culture system is lower than the consumption rate of the growth factor by the bacterium in the culture system.

Both the concentration of the growth factor in the feed medium and the feeding rate of the feed medium may be or may not be constant over the period after inducing the expression.

Feeding of the feed medium may be performed continuously or intermittently. Feeding of the feed medium may be started at the time of the start of the culture, or may be started during the culture. Feeding of the feed medium may be started before inducing the expression, at the time of inducing the expression, or after inducing the expression. Feeding of the feed medium may be started, for example, after the concentration of the growth factor in the medium becomes a certain concentration or lower, specifically, after the growth factor is depleted. When feeding is intermittently performed two or more times, the concentration of the carbon source in the fermentation medium can also be automatically maintained at a low level by controlling the feeding so that the second and following feedings are started when the carbon source in the fermentation medium is depleted in the non-feeding periods immediately before the respective feeding periods (U.S. Pat. No. 5,912,113). Depletion of the carbon source can be detected on the basis of, for example, elevation of pH, or elevation of dissolved oxygen concentration (U.S. Pat. No. 5,912,113).

The feeding of the feed medium may be performed, for example, so that the growth factor is not depleted, or so that depletion of the growth factor is does not continue. However, the growth factor may be depleted so long as production of the fibroin-like protein is improved compared with that observed under the control conditions. The period during which the growth factor is depleted may be, for example, the entire period of the period after inducing the expression, or a period of 90% or less, 70% or less, 50% or less, 30% or less, 20% or less, 10% or less, or 5% or less of the entire period of the period after inducing the expression. The concentration of the growth factor in the medium of 0 (zero) does not necessarily mean that the growth factor is depleted. That is, it is assumed that, for example, a case where although the feeding of the growth factor to the culture system is continued, the concentration of the growth factor in the medium is maintained to be 0 (zero) because of prompt consumption of the fed growth factor should not fall within the case of depletion of the growth factor.

When the growth factor limitation is performed by reducing the feeding amount of the growth factor during the period after inducing the expression, the culture procedures during the period before inducing the expression is not particularly limited so long as the growth factor limitation can be attained during the period after inducing the expression. That is, for example, the concentration of the growth factor in the starting medium, whether the growth factor is fed or not, or feeding procedure of the growth factor during the period before inducing the expression, can be appropriately chosen so that the growth factor limitation can be attained during the period after inducing the expression. Specifically, for example, the concentration of the growth factor in the starting medium may be set to such a concentration of the growth factor in the starting medium for performing the growth factor limitation by reducing the concentration of the growth factor in the starting medium as exemplified above.

Cell proliferation after inducing the expression can also be reduced by, for example, allowing the cells to sufficiently proliferate during the period before inducing the expression. The phrase that "allowing the cells to sufficiently proliferate during the period before inducing the expression" may mean that, for example, OD620 at the time of inducing the expression is 80 or higher, 100 or higher, 120 or higher, 150 or higher, or 200 or higher. Such sufficient proliferation of the cells during the period before inducing the expression can be attained by performing the culture with supplying sufficient amounts of the carbon source and other ingredients required for proliferation of the cells during the period before inducing the expression. The carbon source and other ingredients required for proliferation of the cells may be contained in the starting medium in sufficient amounts, fed in sufficient amounts, or supplied by a combination of these means. When the carbon source is fed, the concentration of the carbon source in the feed medium and the feeding rate of the feed medium may be chosen so that, for example, the feeding rate of the carbon source (determined from the concentration of the carbon source in the feed medium and the feeding rate of the feed medium) is 1 to 100 g/hr for 1 L of the culture medium at the time of the start of the culture.

Any one of such methods for reducing cell proliferation after inducing the expression may be independently used, or two or more of them may be used in an appropriate combination.

By culturing the bacterium as described above, a fibroin-like protein is accumulated in the medium and/or cells of the bacterium. The fibroin-like protein can be accumulated as, for example, inclusion bodies in the cells.

The fibroin-like protein can be collected and quantified by, for example, known methods for collecting and quantifying a heterogeneously expressed protein (see, for example, "Lecture of New Chemical Experiments, Protein VI, Synthesis and Expression", Ed. By Japanese Biochemical Society, Tokyo Kagaku Dojin, 1992, pp. 183-184).

Hereafter, procedures for collecting and quantifying a fibroin-like protein will be exemplified for a case where the fibroin-like protein is accumulated as inclusion bodies in the cells. First, the cells are collected from the culture medium by centrifugation, and then suspended in a buffer. The cell suspension is subjected to such a treatment as ultrasonication or French press to disrupt the cells. Before disrupting the cells, lysozyme may be added to the cell suspension at a final concentration of 0 to 200 mg/l, and the suspension may be incubated on ice for 30 minutes to 20 hours. Then, an insoluble fraction is obtained from the disrupted cell suspension as precipitates by low speed centrifugation (6000 to 15000 rpm, 5 to 10 minutes, 4° C.). The insoluble fraction is appropriately washed with a buffer as required. The number of times of washing is not be particularly limited, and may be, for example, once, twice, or 3 times or more. By suspending the insoluble fraction in a buffer, a suspension of the fibroin-like protein is obtained. As the buffer for suspending the cells or fibroin-like protein, a buffer in which the fibroin-like protein shows a low solubility can be preferably used. Examples of such a buffer include, for example, a buffer containing 20 mM Tris-HCl, 30 mM NaCl, and 10 mM EDTA, and a buffer containing 20 mM Tris-HCl and 30 mM NaCl. pH of the buffer may be, for example, usually 4 to 12, or 6 to 9. A solution of the fibroin-like protein can also be obtained by dissolving the insoluble fraction in an SDS solution or urea solution. The collected fibroin-like protein may contain such components as bacterial cells, medium components, and bacterial metabolic by-products, in addition to the fibroin-like protein. The fibroin-like protein may be purified to a desired degree. The amount of the fibroin-like protein can be determined, for example, as follows: a sample containing the fibroin-like protein such as suspension or solution is subjected to SDS-PAGE, and stained, and then, the amount of the fibroin-like protein can be determined on the basis of intensity of a band at the position corresponding to the molecular weight of the objective fibroin-like protein. The staining can be performed by CBB staining, fluorescence staining, silver staining, or the like. For the quantification, proteins of known concentrations can be used as the standards. Examples of such proteins include, for example, albumin and a fibroin-like protein, the concentration of which can be separately determined.

The fibroin-like protein obtained as described above can be subjected to fibrillation or the like as required, and then used. Fibrillation of a fibroin-like protein can be performed by, for example, a known method. Specifically, fibrillation of a fibroin-like protein can be performed with reference to, for example, the descriptions concerning fibrillation of polypeptides originating in large spigot drag line proteins described in WO2012/165476.

EXAMPLES

Hereafter, the present invention will be more specifically explained with reference to the following non-limiting examples.

Reference Example 1: Construction of Fibroin-Like Protein-Producing Strain

The strain and gene used for the production of fibroin-like protein in the examples (Examples 1 to 5) are as follows.
Host: *Escherichia coli* BLR(DE3)
Vector: pET22b(+)
Fibroin-like protein gene: Gene having the nucleotide sequence described in WO2012/165476A1 as SEQ ID NO: 10

A fibroin-like protein-producing bacterium can be obtained by transforming *Escherichia coli* BLR(DE3) with the pET22b(+) vector (WO2012/165476A1) carrying the aforementioned gene. The nucleotide sequence of the aforementioned gene and the amino acid sequence of the fibroin-like protein encoded by the gene are shown as SEQ ID NOS: 1 and 2, respectively.

Reference Example 2: Preparation of Seed Culture Broth

To 300 ml of the seed culture medium shown in Table 1, which was contained in ajar fermenter, the host bacterium was inoculated at an OD620 of 0.005. OD620 was measured with a spectrophotometer UV-mini1240 (Shimadzu). Culture was performed while maintaining the temperature of the culture medium at 37° C., aerating with 300 mL per 1 minute of air disinfected with a filter, stirring at 1500 rpm, and maintaining the pH of the culture medium to be at a constant of 6.7 by appropriately blowing ammonia gas into the medium. During the culture, the culture medium was periodically sampled, and the glucose concentration in the culture medium was measured by using BF-5 (Oji Scientific Instruments). After 12 hours, that is, at the time point when glucose in the medium for seed culture was completely consumed, the culture was terminated to obtain a seed culture broth.

TABLE 1

| Medium for seed culture (per 1 L at the time of start of culture) | |
| --- | --- |
| Glucose | 40 g |
| KH$_2$PO$_4$ | 2 g |
| MgSO$_4$•7H$_2$O | 1 g |
| Soybean filtrate | 1 g (as nitrogen amount) |
| FeSO$_4$•7H$_2$O | 10 mg |
| MnSO$_4$•5H$_2$O | 10 mg |
| Isoleucine | 1 g |
| GD-113 (anti-foaming agent) | 0.1 mL |

The soybean filtrate is a hydrolysate of soybean proteins. Stock solutions were prepared for glucose and MgSO$_4$.7H$_2$O as solution A, and the other ingredients as solution B. Then, the stock solution of A, as it was, and the stock solution of B adjusted to pH 6.0 by using KOH were separately sterilized in an autoclave at 120° C. for 20 minutes. Then, the stock solutions of A and B were mixed, and ampicillin was added to the mixture at a final concentration of 100 m g/L to obtain the medium for seed culture.

Example 1: Production of Fibroin-Like Protein Under Organic Nitrogen Amount-Reduced Condition (1) Production of fibroin-like protein under control condition According to the following procedures, culture was performed under a condition that a sufficient amount of an organic nitrogen was fed after inducing the expression of the fibroin-like protein, in order to enhance cell proliferation after inducing the expression of the fibroin-like protein. In Example 1, this condition is also referred to as "control condition".

To 255 ml of the production medium shown in Table 2, which was contained in ajar fermenter, 45 ml of the seed culture broth obtained in Reference Example 2 was inoculated. Culture was performed with keeping temperature of the culture medium at 37° C., performing aeration with 300 mL per 1 minute of air disinfected with a filter, stirring at 700 rpm, and maintaining pH of the culture medium to be at a constant pH of 6.9 by appropriately blowing ammonia gas into the medium. During the culture, the culture medium was periodically sampled, and the glucose concentration in the culture medium was measured by using BF-5 (Oji Scientific Instruments). During the culture, dissolved oxygen concentration in the culture medium was also measured by using a dissolved oxygen concentration sensor, OxyProbe (registered trademark) Dissolved Oxygen Sensors (Broadley-James), and was maintained to be 20% of the saturated dissolved oxygen concentration. For maintaining the dissolved oxygen concentration to be 20% of the saturated concentration, the stirring rate was increased up to 2000 rpm as required, and when the dissolved oxygen concentration was still too low even with such increase of stirring rate, aeration was also performed with 30 mL per 1 minute of oxygen disinfected with a filter.

TABLE 2

| Production medium (per 1 L at the time of start of culture) | |
| --- | --- |
| Glucose | 30 g |
| KH$_2$PO$_4$ | 4 g |

TABLE 2-continued

| Production medium (per 1 L at the time of start of culture) | |
| --- | --- |
| MgSO$_4$•7H$_2$O | 2.4 g |
| Bacto yeast extract (BD) | 13.8 g |
| Bacto tryptone (BD) | 20.8 g |
| FeSO$_4$•7H$_2$O | 40 mg |
| CaCl$_2$•2H$_2$O | 40 mg |
| GD-113 (anti-foaming agent) | 0.1 mL |

Stock solutions were prepared for glucose and MgSO$_4$.7H$_2$O as solution A, and the other ingredients as solution B. Then, the stock solutions of A and B were separately sterilized in an autoclave at 120° C. for 20 minutes, and mixed to obtain the production medium.

Glucose contained in the production medium was completely consumed at about 2.5 hours after the start of the culture. Immediately thereafter, 0.3 ml of the 1 M IPTG aqueous solution shown in Table 3 was added. Then, the culture temperature was set at 30° C., addition of the feed medium shown in Table 4 was started at a flow rate of 3.6 ml per 1 hour, and the culture was continued. During the culture, the culture was aerated with 300 mL per 1 minute of air disinfected with a filter, and stirred at a rate of 700 rpm. During the culture, the dissolved oxygen concentration in the culture medium was measured by using a dissolved oxygen concentration sensor, OxyProbe (registered trademark) Dissolved Oxygen Sensors (Broadley-James), and was maintained to be 20% of the saturated dissolved oxygen concentration. For maintaining the dissolved oxygen concentration to be 20% of the saturated concentration, the stirring rate was increased up to 2000 rpm as required. The culture was continued with controlling pH of the culture medium to be at a constant pH of 6.9 by appropriately blowing ammonia gas into the culture medium.

TABLE 3

| IPTG aqueous solution (per 1 L) | |
| --- | --- |
| IPTG (Nakalai Tesque) | 238.3 g |

The solution was sterilized in an autoclave at 120° C. for 20 minutes, and used.

TABLE 4

| Feed medium (per 1 L) | |
| --- | --- |
| Glucose | 455 g |
| Bacto yeast extract (BD) | 76 g |
| Bacto tryptone (BD) | 115 g |

Stock solutions were prepared for glucose as solution A, and the other ingredients as solution B. Then, the stock solutions of A and B were separately sterilized in an autoclave at 120° C. for 20 minutes.

(2) Production of fibroin-like protein under organic nitrogen source-limited condition According to the following procedures, culture was performed under a condition that only glucose was fed after inducing the expression of the fibroin-like protein, in order to reduce cell proliferation after inducing the expression. In Example 1, this condition is also referred to as "organic nitrogen source-limited condition".

To 255 ml of the production medium shown in Table 2, which was contained in ajar fermenter, 45 ml of the seed culture broth obtained in Reference Example 2 was inoculated. Culture was performed while maintaining the temperature of the culture medium at 37° C., aerating with 300 mL per 1 minute of air disinfected with a filter, stirring at 700 rpm, and maintaining the pH of the culture medium at a constant pH of 6.9 by appropriately blowing ammonia gas into the medium. During the culture, the culture medium was periodically sampled, and the glucose concentration in the culture medium was measured by using BF-5 (Oji Scientific Instruments). During the culture, dissolved oxygen concentration in the culture medium was also measured by using a dissolved oxygen concentration sensor, OxyProbe (registered trademark) Dissolved Oxygen Sensors (Broadley-James), and was maintained to be 20% of the saturated dissolved oxygen concentration. For maintaining the dissolved oxygen concentration to be 20% of the saturated concentration, the stirring rate was increased up to 2000 rpm as required, and when the dissolved oxygen concentration was still too low even with such increase of stirring rate, the culture was aerated with 30 mL per 1 minute of oxygen disinfected with a filter.

Glucose contained in the production medium was completely consumed at about 2.5 hours after the start of the culture. Immediately thereafter, 0.3 ml of the 1 M IPTG aqueous solution shown in Table 3 was added. Then, culture temperature was set at 30° C., addition of the feed medium shown in Table 5 was started at a flow rate of 3.6 ml per 1 hour, and the culture was continued. During the culture, the culture was aerated with 300 mL per 1 minute of air disinfected with a filter, and stirring rate was 700 rpm. During the culture, the dissolved oxygen concentration in the culture medium was measured by using a dissolved oxygen concentration sensor, OxyProbe (registered trademark) Dissolved Oxygen Sensors (Broadley-James), and was maintained to be 20% of the saturated dissolved oxygen concentration. For maintaining the dissolved oxygen concentration to be 20% of the saturated concentration, the stirring rate was increased up to 2000 rpm as required. The culture was continued with controlling pH of the culture medium at a constant pH of 6.9 by appropriately blowing ammonia gas into the culture medium.

TABLE 5

| Feed medium (per 1 L) | |
| --- | --- |
| Glucose | 455 g |

The medium was sterilized in an autoclave at 120° C. for 20 minutes, and used.

(3) Analysis

In the culture described in the sections (1) and (2) above, the culture medium was sampled in appropriate volumes during the culture and after the end of the culture, and subjected to the analysis described below.

OD620 of the culture medium was measured by the method described in Reference Example 2. The measurement results are shown in FIG. 1. The data concerning cell proliferation after addition of the IPTG solution, such as the cell amount, cell growth rate, cell growth rate slope, and cumulative specific proliferation rate, are shown in FIGS. 2A to 2D, respectively.

Figure 3A:
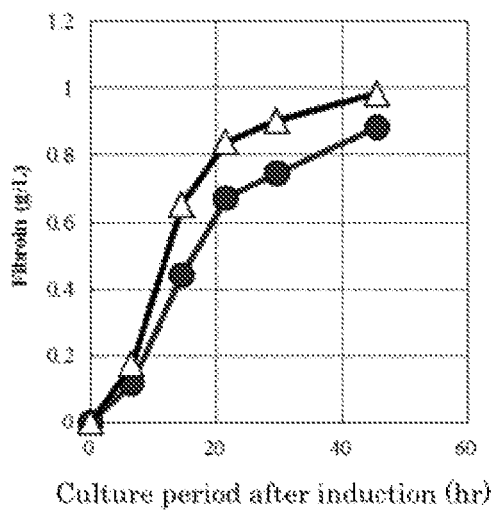
FIG. 3(A) to FIG. 3(C): Graphs showing the results concerning production of fibroin-like protein after addition of an IPTG solution: (A) accumulation amount of fibroin-like protein relative to volume of culture medium; (B) accumulation amount of fibroin-like protein relative to cell weight; and (C) cumulative productivity of fibroin-like protein. The symbols ● indicate the results obtained with the control condition, and the symbols Δ indicate the results obtained with the organic nitrogen source-limited condition.
Figure 3B:
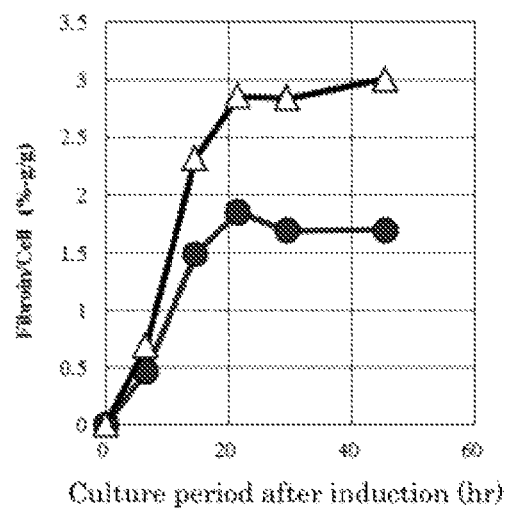
Figure 3C:
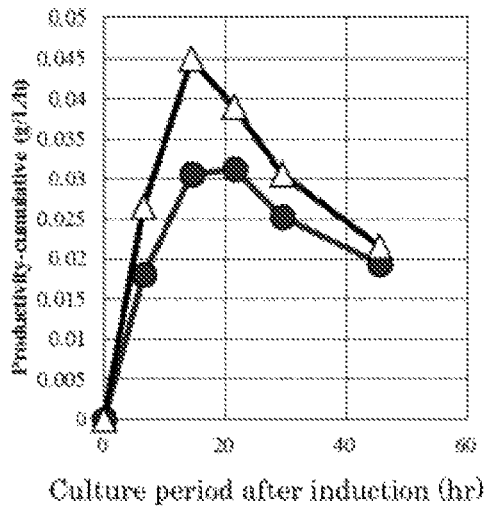

The produced fibroin-like protein was appropriately quantified. The data concerning the production amount of fibroin-like protein, such as the accumulation amount of fibroin-like protein relative to volume of the culture medium, accumulation amount of fibroin-like protein relative to cell weight, and cumulative productivity of fibroin-like protein, are shown in FIGS. 3A to 3C, respectively.

The cumulative specific proliferation rate observed at 14 (21.5) hours after the addition of IPTG was 0.031 (0.033)/h under the control condition, but it decreased to 0.027 (0.022)/h under the organic nitrogen source-limited condition. The cell growth rate observed at 14 (21.5) hours after the addition of IPTG was 57.5 (102.6)% under the control condition, but it decreased to 48.2 (62.6)% under the organic nitrogen source-limited condition. The cell growth rate slope observed at 14 (21.5) hours after the addition of IPTG was 3.96 (4.77)%/h under the control condition, but it decreased to 3.32 (2.91)%/h under the organic nitrogen source-limited condition. In the indications of the aforementioned data, the data indicated outside the parentheses and the data indicated in the parentheses correspond to those obtained at 14 hours after the addition of IPTG and those obtained at 21.5 hours after the addition of IPTG, respectively (the same shall apply hereinafter).

The accumulation amount of the fibroin-like protein relative to volume of the culture medium observed at 14 (21.5) hours after the addition of IPTG was 0.44 (0.67) g/L under the control condition, but it was improved to 0.65 (0.84) g/L under the organic nitrogen source-limited condition. The accumulation amount of the fibroin-like protein relative to cell weight observed at 14 (21.5) hours after the addition of IPTG was 1.49 (1.86)% under the control condition, but it was improved to 2.32 (2.86)% under the organic nitrogen source-limited condition. The cumulative productivity of the fibroin-like protein observed at 14 (21.5) hours after the addition of IPTG was 0.030 (0.031) g/L/hr under the control condition, but it was improved to 0.045 (0.039) g/L/hr under the organic nitrogen source-limited condition.

On the basis of the results described above, it was revealed that by performing the culture under the organic nitrogen source-limited condition during the period after inducing the expression, the cell proliferation during that period was reduced, and production of the fibroin-like protein was improved.

Example 2: Production of Fibroin-Like Protein Under Phosphate Source Amount-Reduced Condition (1) Production of Fibroin-Like Protein Under Control Condition According to the following method, culture was performed under a condition that the phosphate source was added to the feed medium in a sufficient amount (12 g/L in terms of $KH_2PO_4$ amount), so that the cell proliferation should continue after inducing the expression of the fibroin-like protein. In Example 2, this condition is also referred to as "control condition".

By using the seed culture medium shown in Table 6, culture was performed under the conditions described in Reference Example 2 until glucose was completely consumed to obtain a seed culture broth. Then, to 227 ml of the production medium shown in Table 7, which was contained in a jar fermenter, 45 ml of the above seed culture broth was inoculated. Culture was performed while maintaining the temperature of the culture medium at 37° C., aerating with 300 mL per 1 minute of air disinfected with a filter, stirring at 700 rpm, and maintaining the pH of the culture medium at a constant pH of 6.9 by appropriately blowing ammonia gas into the medium. During the culture, the culture medium was periodically sampled, and the glucose concentration in the culture medium was measured by using BF-5 (Oji Scientific Instruments). During the culture, the dissolved oxygen concentration in the culture medium was also measured by using a dissolved oxygen concentration sensor, OxyProbe (registered trademark) Dissolved Oxygen Sensors (Broadley-James), and was maintained to be 20% of the saturated dissolved oxygen concentration. For maintaining the dissolved oxygen concentration to be 20% of the saturated concentration, the stirring rate was increased up to 2000 rpm as required, and when the dissolved oxygen concentration was still too low even with of the increased stirring rate, the culture was aerated with 30 mL per 1 minute of oxygen disinfected with a filter.

TABLE 6

| Medium for seed culture (per 1 L at the time of start of culture) | |
| --- | --- |
| Glucose | 40 g |
| $KH_2PO_4$ | 2 g |
| $MgSO_4 \cdot 7H_2O$ | 1 g |
| CSL | 1 g (as nitrogen amount) |
| $FeSO_4 \cdot 7H_2O$ | 10 mg |
| $MnSO_4 \cdot 5H_2O$ | 10 mg |
| Isoleucine | 1 g |
| GD-113 (anti-foaming agent) | 0.1 mL |

Stock solutions were prepared for glucose and $MgSO_4 \cdot 7H_2O$ as solution A, CSL (corn steep liquor) as solution B, and the other ingredients as solution C. Then, the stock solutions of A and C, as is, were separately sterilized in an autoclave at 120° C. for 20 minutes. The pH of the stock solution of the solution B was lowered to 2 by using sulfuric acid, and the solution was subjected to a heat treatment at 80° C. for 60 minutes, and then sterilized in an autoclave at 120° C. for 20 minutes. Then, the stock solutions of A, B, and C were mixed, and ampicillin was added to the mixture at a final concentration of 100 m g/L to obtain the medium for seed culture.

TABLE 7

| Production medium (per 1 L at the time of start of culture) | |
| --- | --- |
| Glucose | 2 g |
| $KH_2PO_4$ | 2 g |
| $MgSO_4 \cdot 7H_2O$ | 2.4 g |
| CSL | 1 g (as nitrogen amount) |
| $FeSO_4 \cdot 7H_2O$ | 40 mg |
| $MnSO_4 \cdot 5H_2O$ | 40 mg |
| $CaCl_2 \cdot 2H_2O$ | 40 mg |
| Isoleucine | 3 g |
| GD-113 (anti-foaming agent) | 0.1 mL |

Stock solutions were prepared for glucose and $MgSO_4 \cdot 7H_2O$ as solution A, CSL (corn steep liquor) as solution B, and the other ingredients as solution C. Then, the stock solutions of A and C, as is, were separately sterilized in an autoclave at 120° C. for 20 minutes. The pH of the stock solution of B was lowered to 2 by using sulfuric acid, and the solution was subjected to a heat treatment at 80° C. for 60 minutes, and then sterilized in an autoclave at 120° C. for 20 minutes. Then, the stock solutions of A, B, and C were mixed to obtain the production medium.

Glucose in the production medium was completely consumed at about 1.0 hour after the start of the culture. Immediately thereafter, addition of the feed medium shown in Table 5 was started at a flow rate of 4 ml per 1 hour, and the culture was continued. During the culture, the culture was aerated with 300 mL per 1 minute of air disinfected with a filter, and stirred at a rate of 700 rpm. During the culture, the dissolved oxygen concentration in the culture medium was measured by using a dissolved oxygen concentration sensor, OxyProbe (registered trademark) Dissolved Oxygen Sensors (Broadley-James), and was maintained to be 20% of the saturated dissolved oxygen concentration. To maintain the dissolved oxygen concentration to be 20% of the saturated concentration, the stirring rate was increased up to 2000 rpm as required, and when the dissolved oxygen concentration was still too low even with of the increased stirring rate, the culture was aerated with 30 to 90 mL per 1 minute of oxygen disinfected with a filter. When it became difficult to maintain the intended dissolved oxygen concentration, the flow rate of the feed medium was decreased. The culture was continued with controlling pH of the culture medium at a constant pH of 6.9 by appropriately blowing ammonia gas into the culture medium.

After about 8 hours from the start of the culture, i.e. at the time point when the feeding volume of the feed medium shown in Table 5 reached 28 mL, 0.3 ml of the 1 M (238.3 g/L) IPTG aqueous solution shown in Table 3 was added. Then, culture temperature was set at 30° C., addition of the feed medium shown in Table 8 was started at a flow rate of 4.0 ml per 1 hour, and the culture was continued. During the culture, the culture was aerated with 300 mL per 1 minute of air disinfected with a filter, and stirred at a rate of 700 rpm. During the culture, the dissolved oxygen concentration in the culture medium was measured by using a dissolved oxygen concentration sensor, OxyProbe (registered trademark) Dissolved Oxygen Sensors (Broadley-James), and was maintained to be 20% of the saturated dissolved oxygen concentration. To maintain the dissolved oxygen concentration to be 20% of the saturated concentration, the stirring rate was increased up to 2000 rpm as required. The culture was continued with controlling pH of the culture medium at a constant pH of 6.9 by appropriately blowing ammonia gas into the culture medium.

TABLE 8

| Feed medium (per 1 L) | |
| --- | --- |
| Glucose | 455 g |
| $KH_2PO_4$ | 12 g |

Stock solutions were prepared for glucose as solution A, and $KH_2PO_4$ as solution B. Then, the stock solutions of A and B were separately sterilized in an autoclave at 120° C. for 20 minutes.

(2) Production of Fibroin-Like Protein Under Phosphate-Limited Condition

According to the following procedures, culture was performed under a condition of no addition of a phosphate source to the feed medium, in order to reduce cell proliferation after inducing the expression of the fibroin-like protein. In Example 2, this condition is also referred to as "phosphate-limited condition".

By using the medium for seed culture shown in Table 6, culture was performed under the condition described in Reference Example 2 until glucose was completely consumed to obtain a seed culture broth. Then, to 227 ml of the production medium shown in Table 7, which was contained in a jar fermenter, 45 ml of the above seed culture broth was inoculated. Culture was performed while maintaining the temperature of the culture medium at 37° C., aerating with 300 mL per 1 minute of air disinfected with a filter, stirring at 700 rpm, and maintaining the pH of the culture medium at a constant pH of 6.9 by appropriately blowing ammonia gas into the medium. During the culture, the culture medium was periodically sampled, and the glucose concentration in the culture medium was measured by using BF-5 (Oji Scientific Instruments). During the culture, dissolved oxygen concentration in the culture medium was also measured by using a dissolved oxygen concentration sensor, OxyProbe (registered trademark) Dissolved Oxygen Sensors (Broadley-James), and was maintained to be 20% of the saturated dissolved oxygen concentration. For maintaining the dissolved oxygen concentration to be 20% of the saturated concentration, the stirring rate was increased up to 2000 rpm as required, and when the dissolved oxygen concentration was still too low even with such increase of stirring rate, aeration was also performed with 30 mL per 1 minute of oxygen disinfected with a filter.

Glucose contained in the production medium was completely consumed at about 1.0 hour after the start of the culture. Immediately thereafter, addition of the feed medium shown in Table 5 was started at a flow rate of 4 ml per 1 hour, and the culture was continued. During the culture, the culture was aerated with 300 mL per 1 minute of air disinfected with a filter, and stirred at a rate of 700 rpm. During the culture, the dissolved oxygen concentration in the culture medium was measured by using a dissolved oxygen concentration sensor, OxyProbe (registered trademark) Dissolved Oxygen Sensors (Broadley-James), and was maintained to be 20% of the saturated dissolved oxygen concentration. To maintain the dissolved oxygen concentration to be 20% of the saturated concentration, the stirring rate was increased up to 2000 rpm as required, and when the dissolved oxygen concentration was still too low even with such increase of stirring rate, the culture was aerated with 30 to 90 mL per 1 minute of oxygen disinfected with a filter. When it became difficult to maintain the intended dissolved oxygen concentration, the flow rate of the feed medium was decreased. The culture was continued with controlling pH of the culture medium at a constant pH of 6.9 by appropriately blowing ammonia gas into the culture medium.

After about 8 hours from the start of the culture, i.e. at the time point when the feeding volume of the feed medium shown in Table 5 reached 28 mL, 0.3 ml of the 1 M (238.3 g/L) IPTG aqueous solution shown in Table 3 was added. Then, the culture temperature was set at 30° C., addition of the feed medium shown in Table 5 was started at a flow rate of 4.0 ml per 1 hour, and the culture was continued. During the culture, the culture was aerated with 300 mL per 1 minute of air disinfected with a filter, and stirred at a rate of 700 rpm. During the culture, the dissolved oxygen concentration in the culture medium was measured by using a dissolved oxygen concentration sensor, OxyProbe (registered trademark) Dissolved Oxygen Sensors (Broadley-James), and was maintained to be 20% of the saturated dissolved oxygen concentration. To maintain the dissolved oxygen concentration to be 20% of the saturated concentration, the stirring rate was increased up to 2000 rpm as required. The culture was continued with controlling the pH of the culture medium at a constant pH of 6.9 by appropriately blowing ammonia gas into the culture medium.

(3) Analysis

In the culture described in the sections (1) and (2) above, the culture medium was sampled in appropriate volumes during the culture and after the end of the culture, and subjected to the analysis described below.

Figure 4A:
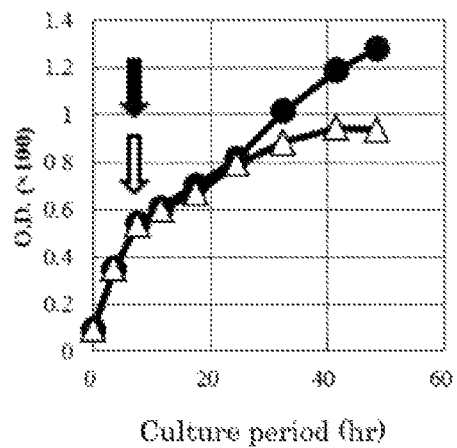
FIG. 4(A) to FIG. 4(C): Graphs showing the results of culture: (A) OD620, (B) phosphate concentration in culture medium in terms of $KH_2PO_4$ concentration, and (C) total phosphate consumption amount in terms of $KH_2PO_4$ amount. The symbols ● indicate the results obtained with the control condition, and the symbols Δ indicate the results obtained with the phosphate-limited condition. The arrows indicate the time points at which an IPTG solution was added.
Figure 4B:
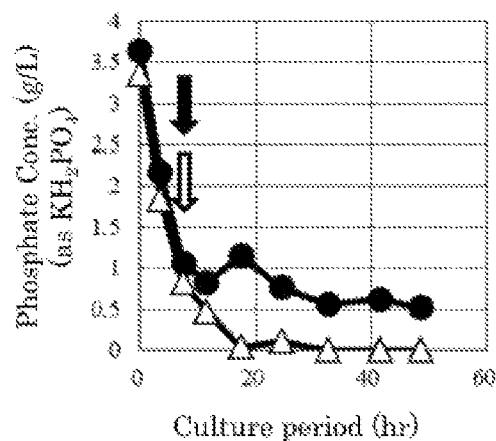
Figure 4C:
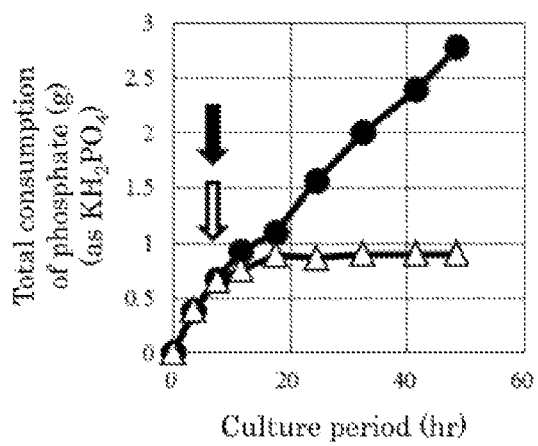
Figures 5A, 5B:
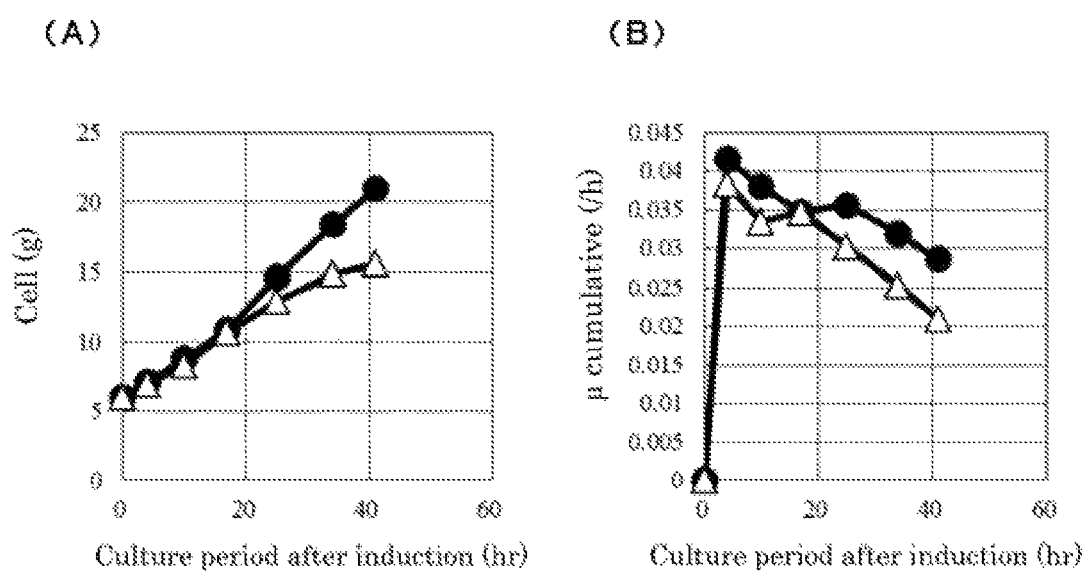
FIG. 5(A) and FIG. 5(B): Graphs showing the results concerning the cell proliferation after addition of an IPTG solution: (A) cell amount, and (B) cumulative specific proliferation rate. The symbols ● indicate the results obtained with the control condition, and the symbols Δ indicate the results obtained with the phosphate-limited condition.

OD620 of the culture medium was measured by the method described in Reference Example 2. The phosphate concentration in the medium was also measured by a conventional method using Phospha C-Test Wako (Wako Pure Chemical Industries). The measurement results of OD620, phosphate concentration (in terms of $KH_2PO_4$ concentration), and total phosphate consumption amount (in terms of $KH_2PO_4$ amount) are shown in FIGS. 4A to 4C, respectively. The data concerning cell proliferation after addition of the IPTG solution (cell amount, and cumulative specific proliferation rate) are shown in FIGS. 5A and 5B, respectively.

Figure 6A:
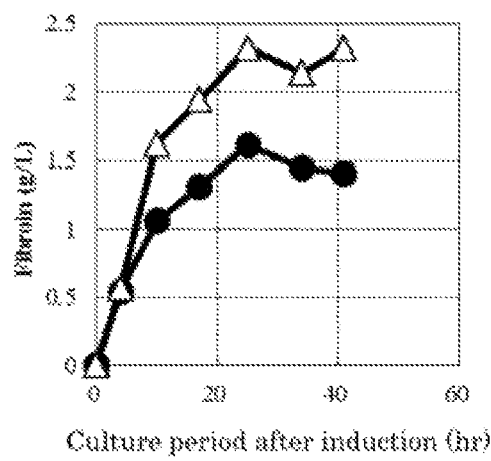
FIG. 6(A) to FIG. 6(C): Graphs showing the results concerning production of fibroin-like protein after addition of an IPTG solution: (A) accumulation amount of fibroin-like protein relative to volume of culture medium; (B) accumulation amount of fibroin-like protein relative to cell weight; and (C) cumulative productivity of fibroin-like protein. The symbols ● indicate the results obtained with the control condition, and the symbols Δ indicate the results obtained with the phosphate-limited condition.
Figure 6B:
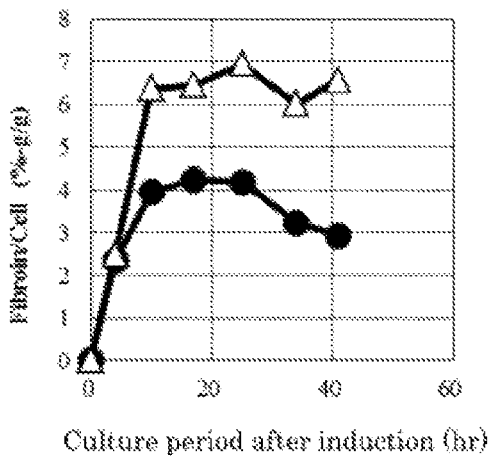
Figure 6C:
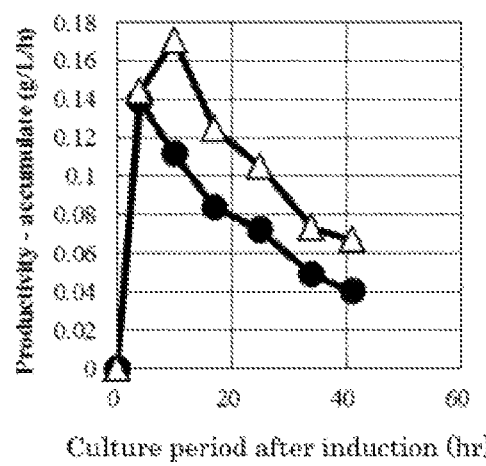

The produced fibroin-like protein was appropriately quantified. The data concerning the production amount of fibroin-like protein, that is, the accumulation amount of fibroin-like protein relative to volume of the culture medium, the accumulation amount of fibroin-like protein relative to cell weight, and the cumulative specific production rate of fibroin-like protein, are shown in FIG. 6A to 6C, respectively.

The total phosphate consumption amount observed at 25 hours after the addition of IPTG (i.e. 32.5 hours after the start of the culture) was 2.05 g under the control condition, but it decreased to 0.90 g under the phosphate-limited condition.

The cumulative specific proliferation rate observed at 25 hours after the addition of IPTG was 0.035/h under the control condition, but it decreased to 0.030/h under the phosphate-limited condition.

The accumulation amount of the fibroin-like protein relative to volume of the culture medium observed at 25 hours after the addition of IPTG was 1.61 g/L under the control condition, but it was improved to 2.32 g/L under the phosphate-limited condition. The accumulation amount of the fibroin-like protein relative to cell weight observed at 25 hours after the addition of IPTG was 4.20% under the control condition, but it was improved to 6.94% under the phosphate-limited condition. The cumulative productivity of the fibroin-like protein observed at 25 hours after the addition of IPTG was 0.072 g/L/h under the control condition, but it was improved to 0.105 g/L/h under the phosphate-limited condition.

On the basis of the results described above, it was revealed that, by performing the culture under the phosphate-limited condition during the period after inducing the expression, the cell proliferation during that period was reduced, and production of the fibroin-like protein was improved.

Example 3: Production of Fibroin-Like Protein Under Condition of Enhancing Cell Proliferation Before Inducing Expression (1) Production of Fibroin-Like Protein Under Control Condition Culture was performed under the following condition. In Example 3, this condition is also referred to as "control condition".

By using the medium for seed culture shown in Table 9, culture was performed under the condition described in Reference Example 2 until glucose was completely consumed to obtain a seed culture broth. Then, to 255 ml of the production medium shown in Table 10, which was contained in a jar fermenter, 45 ml of the above seed culture broth was inoculated. Culture was performed while maintaining the temperature of the culture medium at 37° C., aerating with 300 mL per 1 minute of air disinfected with a filter, stirring at 700 rpm, and maintaining the pH of the culture medium at a constant pH of 6.9 by appropriately blowing ammonia gas into the medium. During the culture, the culture medium was periodically sampled, and the glucose concentration in the culture medium was measured by using BF-5 (Oji Scientific Instruments). During the culture, the dissolved oxygen concentration in the culture medium was also measured by using a dissolved oxygen concentration sensor, OxyProbe (registered trademark) Dissolved Oxygen Sensors (Broadley-James), and was maintained to be 20% of the saturated dissolved oxygen concentration. To maintain the dissolved oxygen concentration to be 20% of the saturated concentration, the stirring rate was increased up to 2000 rpm as required, and when the dissolved oxygen concentration was still too low even with of the increased stirring rate, aeration was also performed with 30 mL per 1 minute of oxygen disinfected with a filter.

TABLE 9

| Medium for seed culture (per 1 L at the time of start of culture) | |
|---|---|
| Glucose | 40 g |
| $KH_2PO_4$ | 2 g |
| $MgSO_4 \cdot 7H_2O$ | 1 g |
| CSL | 1 g (as nitrogen amount) |
| $FeSO_4 \cdot 7H_2O$ | 10 mg |
| $MnSO_4 \cdot 5H_2O$ | 10 mg |
| Isoleucine | 1 g |
| GD-113 (anti-foaming agent) | 0.1 mL |

Stock solutions were prepared for glucose and $MgSO_4 \cdot 7H_2O$ as solution A, CSL (corn steep liquor) as solution B, and the other ingredients as solution C. Then, the stock solutions of A and C, as is, were separately sterilized in an autoclave at 120° C. for 20 minutes. The pH of the stock solution of B was lowered to 2 by using sulfuric acid, and the solution was subjected to a heat treatment at 80° C. for 60 minutes, and then sterilized in an autoclave at 120° C. for 20 minutes. Then, the stock solutions of A, B, and C were mixed, and ampicillin was added to the mixture at a final concentration of 100 m g/L to obtain the medium for seed culture.

TABLE 10

| Production medium (per 1 L at the time of start of culture) | |
|---|---|
| Glucose | 45 g |
| $KH_2PO_4$ | 9 g |
| $MgSO_4 \cdot 7H_2O$ | 2.4 g |
| CSL | 1 g (as nitrogen amount) |
| $FeSO_4 \cdot 7H_2O$ | 40 mg |
| $MnSO_4 \cdot 5H_2O$ | 40 mg |
| $CaCl_2 \cdot 2H_2O$ | 40 mg |
| Isoleucine | 3 g |
| GD-113 (anti-foaming agent) | 0.1 mL |

Stock solutions were prepared for glucose and $MgSO_4 \cdot 7H_2O$ as solution A, CSL (corn steep liquor) as solution B, and the other ingredients as solution C. Then, the stock solutions of A and C, as is, were separately sterilized in an autoclave at 120° C. for 20 minutes. The pH of the stock solution B was lowered to 2 by using sulfuric acid, and the solution was subjected to a heat treatment at 80° C. for 60 minutes, and then sterilized in an autoclave at 120° C. for 20 minutes. Then, the stock solutions A, B, and C were mixed to obtain the production medium.

Glucose contained in the production medium was completely consumed at about 4.0 hours after the start of the culture. Immediately thereafter, 0.3 ml of the 1 M IPTG aqueous solution shown in Table 3 was added. Then, culture temperature was set at 30° C., addition of the feed medium shown in Table 5 was started at a flow rate of 3.6 ml per 1 hour, and the culture was continued. During the culture, the culture was aerated with 300 mL per 1 minute of air disinfected with a filter, and stirred at a rate of 700 rpm. During the culture, the dissolved oxygen concentration in the culture medium was measured by using a dissolved oxygen concentration sensor, OxyProbe (registered trademark) Dissolved Oxygen Sensors (Broadley-James), and was maintained to be 20% of the saturated dissolved oxygen concentration. To maintain the dissolved oxygen concentration to be 20% of the saturated concentration, the stirring rate was increased up to 2000 rpm as required. The culture was continued with controlling pH of the culture medium at a constant pH of 6.9 by appropriately blowing ammonia gas into the culture medium.

(2) Production of Fibroin-Like Protein Under Condition of Enhanced Cell Proliferation Before Inducing Expression According to the following procedures, culture was performed under a condition that a sufficient amount of glucose was fed before inducing the expression of the fibroin-like protein to allow the cells to sufficiently grow before the induction of the expression in order to reduce cell proliferation after inducing the expression. In Example 3, this condition is also referred to as "condition that cell proliferation before inducing the expression is enhanced".

By using the medium for seed culture shown in Table 9, culture was performed under the condition described in Reference Example 2 until glucose was completely consumed to obtain a seed culture broth. Then, to 255 ml of the production medium shown in Table 10, which was contained in a jar fermenter, 45 ml of the above seed culture broth was inoculated. Culture was performed while maintaining the temperature of the culture medium at 37° C., aerating with 300 mL per 1 minute of air disinfected with a filter, stirring at 700 rpm, and maintaining the pH of the culture medium at a constant pH of 6.9 by appropriately blowing ammonia gas into the medium. During the culture, the culture medium was periodically sampled, and the glucose concentration in the culture medium was measured by using BF-5 (Oji Scientific Instruments). During the culture, the dissolved oxygen concentration in the culture medium was also measured by using a dissolved oxygen concentration sensor, OxyProbe (registered trademark) Dissolved Oxygen Sensors (Broadley-James), and was maintained to be 20% of the saturated dissolved oxygen concentration. To maintain the dissolved oxygen concentration to be 20% of the saturated concentration, the stirring rate was increased up to 2000 rpm as required, and when the dissolved oxygen concentration was still too low even with of the increased stirring rate, the culture was aerated with 30 mL per 1 minute of oxygen disinfected with a filter.

Glucose contained in the production medium was completely consumed at about 4.0 hours after the start of the culture. Immediately thereafter, addition of the feed medium shown in Table 5 was started, and the culture was continued. The flow rate of the feed medium was gradually increased within the range of 10 to 40 ml per 1 hour so as to obtain an average flow rate of 22.5 ml per 1 hour. During the culture, aeration was performed with 300 mL per 1 minute of air disinfected with a filter, and stirring rate was 700 rpm. During the culture, dissolved oxygen concentration in the culture medium was measured by using a dissolved oxygen concentration sensor, OxyProbe (registered trademark) Dissolved Oxygen Sensors (Broadley-James), and was maintained to be 20% of the saturated dissolved oxygen concentration. To maintain the dissolved oxygen concentration to be 20% of the saturated concentration, the stirring rate was increased up to 2000 rpm as required, and when the dissolved oxygen concentration was still too low even with such increase of stirring rate, aeration was also performed with 30 to 90 mL per 1 minute of oxygen disinfected with a filter. When it became difficult to maintain the intended dissolved oxygen concentration, the flow rate of the feed medium was decreased. The culture was continued with controlling pH of the culture medium at a constant pH of 6.9 by appropriately blowing ammonia gas into the culture medium.

After about 8 hours from the start of the culture, that is, at the time point when the feeding volume of the feed medium shown in Table 5 reached 90 mL, 1.2 ml of the 1 M (238.3 g/L) IPTG aqueous solution shown in Table 3 was added. Then, culture temperature was set at 30° C., addition of the feed medium shown in Table 5 was started at a flow rate of 3.6 ml per 1 hour, and the culture was continued. During the culture, aeration was performed with 300 mL per 1 minute of air disinfected with a filter, and stirring rate was 700 rpm. During the culture, the dissolved oxygen concentration in the culture medium was measured by using a dissolved oxygen concentration sensor, OxyProbe (registered trademark) Dissolved Oxygen Sensors (Broadley-James), and was maintained to be 20% of the saturated dissolved oxygen concentration. To maintain the dissolved oxygen concentration to be 20% of the saturated concentration, the stirring rate was increased up to 2000 rpm as required. The culture was continued with controlling pH of the culture medium at a constant pH of 6.9 by appropriately blowing ammonia gas into the culture medium.

(3) Analysis

In the culture described in the sections (1) and (2) above, the culture medium was sampled in appropriate volumes during the culture and after the end of the culture, and subjected to the analysis described below.

Figure 7:
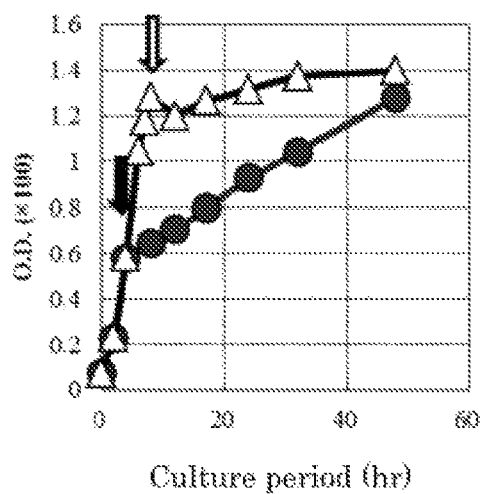
FIG. 7: Graph showing change of OD620 over time. The symbols ● indicate the results obtained with the control condition, and the symbols Δ indicate the results obtained under conditions of enhanced cell proliferation before the induction of the expression. The arrows indicate the time points at which an IPTG solution was added.
Figure 8A:
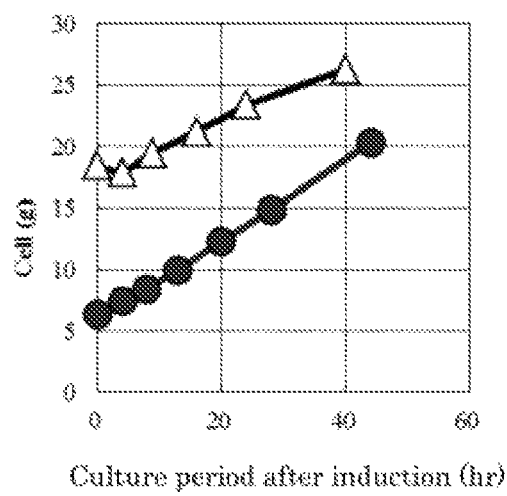
FIG. 8(A) to FIG. 8(D): Graphs showing the results concerning the cell proliferation after addition of an IPTG solution: (A) cell amount, (B) cell growth rate, (C) cell growth rate slope, and (D) cumulative specific proliferation rate. The symbols ● indicate the results obtained with the control condition, and the symbols Δ indicate the results obtained under conditions of enhanced cell proliferation before the induction of the expression.
Figure 8B:
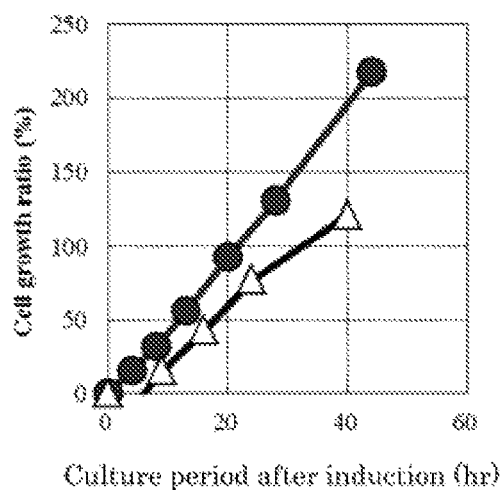
Figure 8C:
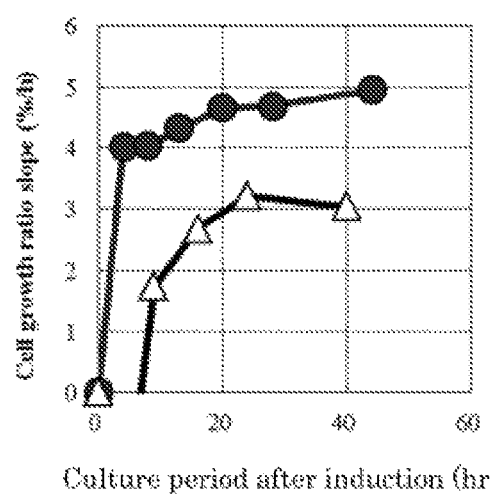
Figure 8D:
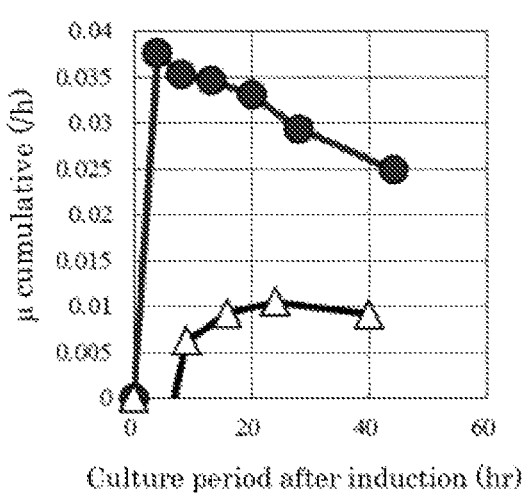

OD620 of the culture medium was measured by the method described in Reference Example 2. The measurement results are shown in FIG. 7. The data concerning cell proliferation after addition of the IPTG solution, that is, cell amount, cell growth rate, cell growth rate slope, and cumulative specific proliferation rate, are shown in FIGS. 8A to 8D, respectively.

Figure 9A:
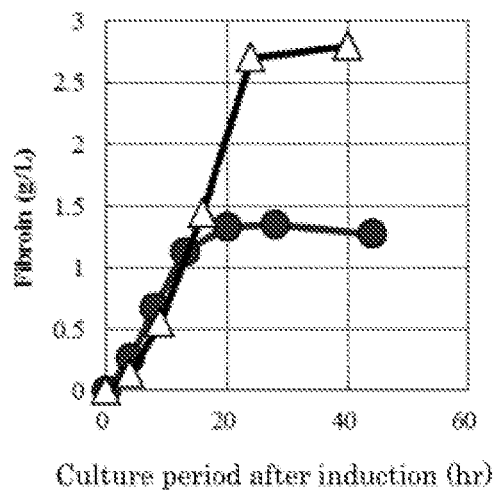
FIG. 9(A) to FIG. 9(C): Graphs showing the results concerning production of fibroin-like protein after addition of an IPTG solution: (A) accumulation amount of fibroin-like protein relative to volume of culture medium; (B) accumulation amount of fibroin-like protein relative to cell weight; and (C) cumulative productivity of fibroin-like protein. The symbols ● indicate the results obtained with the control condition, and the symbols Δ indicate the results obtained under conditions of enhanced cell proliferation before inducing the expression.
Figure 9B:
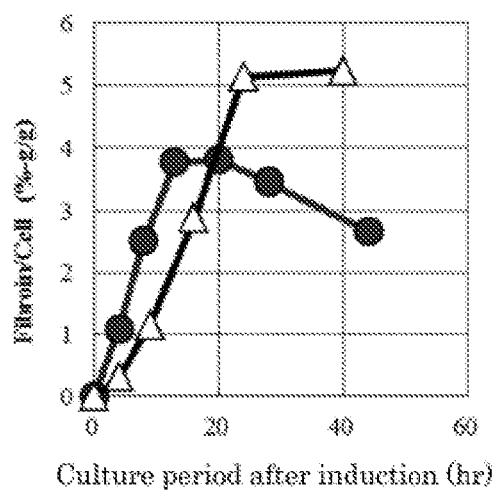
Figure 9C:
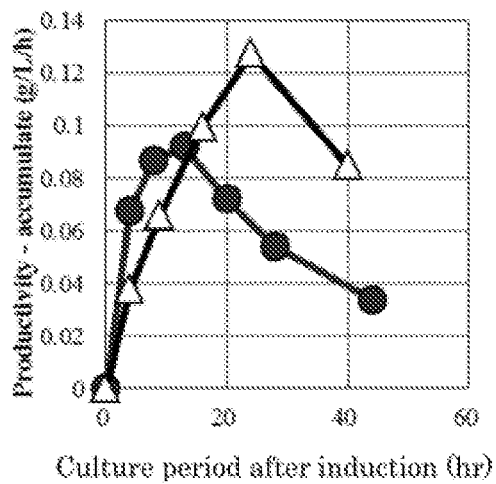

The produced fibroin-like protein was appropriately quantified. The data concerning the production amount of fibroin-like protein, that is, accumulation amount of fibroin-like protein relative to volume of the culture medium, accumulation amount of fibroin-like protein relative to cell weight, and cumulative productivity of fibroin-like protein are shown in FIGS. 9A to 9C, respectively.

The cumulative specific proliferation rate was 0.033 (0.029)/h at 20 (28) hours after the addition of IPTG under the control condition, but it decreased to 0.011/h at 24 hours after the addition of IPTG under the condition that cell proliferation before inducing the expression was enhanced. The cell growth rate was 93.1 (131.3)% at 20 (28) hours after the addition of IPTG under the control condition, but it decreased to 77.1% at 24 hours after the addition of IPTG under the condition that cell proliferation before inducing the expression was enhanced. The cell growth rate slope was 4.66 (4.69)%/h at 20 (28) hours after the addition of IPTG under the control condition, but it decreased to 3.21%/h at 24 hours after the addition of IPTG under the condition that cell proliferation before inducing the expression was enhanced. In the indications of the aforementioned data, the data indicated outside the parentheses and the data indicated in the parentheses correspond to those obtained at 20 hours after the addition of IPTG and those obtained at 28 hours after the addition of IPTG, respectively (the same shall apply hereinafter).

The accumulation amount of the fibroin-like protein relative to volume of the culture medium was 1.34 (1.36) g/L at 20 (28) hours after the addition of IPTG under the control condition, but it was improved to 2.70 g/L at 24 hours after the addition of IPTG under the condition that cell proliferation before inducing the expression was enhanced. The accumulation amount of the fibroin-like protein relative to cell weight was 3.80 (3.45)% at 20 (28) hours after the addition of IPTG under the control condition, but it was improved to 5.12% at 24 hours after the addition of IPTG under the condition that cell proliferation before inducing the expression was enhanced. The cumulative productivity of the fibroin-like protein was 0.072 (0.054) g/L/hr at 20 (28) hours after the addition of IPTG under the control condition, but it was improved to 0.128 g/L/hr at 24 hours after the addition of IPTG under the condition that cell proliferation before inducing the expression was enhanced.

On the basis of the results described above, it was revealed that by allowing the cells to sufficiently grow before inducing the expression, the cell proliferation during the period after inducing the expression was decreased, and production of the fibroin-like protein was improved.

Example 4: Production of Fibroin-Like Protein Under Carbon Source Amount-Reduced Condition (1) Production of Fibroin-Like Protein Under Control Condition According to the following procedures, culture was performed under a condition that the feeding rate of the carbon source (glucose) was 8 mL/hr, so that the cell proliferation should continue after inducing the expression of the fibroin-like protein. In Example 4, this condition is also referred to as "control condition".

By using the medium for seed culture shown in Table 1, culture was performed under the condition described in Reference Example 2 until glucose was completely consumed to obtain a seed culture broth. Then, to 255 ml of the production medium shown in Table 10, which was contained in a jar fermenter, 45 ml of the above seed culture broth was inoculated. Culture was performed while maintaining temperature of the culture medium at 37° C., aerating with 300 mL per 1 minute of air disinfected with a filter, stirring at 700 rpm, and maintaining the pH of the culture medium at a constant pH of 6.9 by appropriately blowing ammonia gas into the medium. During the culture, the culture medium was periodically sampled, and the glucose concentration in the culture medium was measured by using BF-5 (Oji Scientific Instruments). During the culture, dissolved oxygen concentration in the culture medium was also measured by using a dissolved oxygen concentration sensor, OxyProbe (registered trademark) Dissolved Oxygen Sensors (Broadley-James), and was maintained to be 20% of the saturated dissolved oxygen concentration. To maintain the dissolved oxygen concentration to be 20% of the saturated concentration, the stirring rate was increased up to 2000 rpm as required, and when the dissolved oxygen concentration was still too low even with the increased stirring rate, the culture was aerated with 30 mL per 1 minute of oxygen disinfected with a filter.

Glucose contained in the production medium was completely consumed at about 4.0 hours after the start of the culture. Immediately thereafter, 0.3 ml of the 1 M (238.3 g/L) IPTG aqueous solution shown in Table 3 was added. Then, culture temperature was set at 30° C., addition of the feed medium shown in Table 4 was started at a flow rate of 8.0 ml per 1 hour, and the culture was continued. During the culture, the culture was aerated with 300 mL per 1 minute of air disinfected with a filter, and stirred at a rate of 700 rpm. During the culture, the dissolved oxygen concentration in the culture medium was measured by using a dissolved oxygen concentration sensor, OxyProbe (registered trademark) Dissolved Oxygen Sensors (Broadley-James), and was maintained to be 20% of the saturated dissolved oxygen concentration. To maintain the dissolved oxygen concentration to be 20% of the saturated concentration, the stirring rate was increased up to 2000 rpm as required. The culture was continued with controlling pH of the culture medium at a constant pH of 6.9 by appropriately blowing ammonia gas into the culture medium.

Production of Fibroin-Like Protein Under Carbon Source-Limited Condition

According to the following procedures, culture was performed under the condition that the feeding rate of the carbon source (glucose) was 4 mL/hr, in order to reduce cell proliferation after inducing the expression of the fibroin-like protein. In Example 4, this condition is also referred to as "carbon source-limited condition".

By using the medium for seed culture shown in Table 1, culture was performed under the condition described in Reference Example 2 until glucose was completely consumed to obtain a seed culture broth. Then, to 255 ml of the production medium shown in Table 2, which was contained in a jar fermenter, 45 ml of the above seed culture broth was inoculated. Culture was performed while maintaining temperature of the culture medium at 37° C., aerating with 300 mL per 1 minute of air disinfected with a filter, stirring at 700 rpm, and maintaining pH of the culture medium at a constant pH of 6.9 by appropriately blowing ammonia gas into the medium. During the culture, the culture medium was periodically sampled, and the glucose concentration in the culture medium was measured by using BF-5 (Oji Scientific Instruments). During the culture, the dissolved oxygen concentration in the culture medium was also measured by using a dissolved oxygen concentration sensor, OxyProbe (registered trademark) Dissolved Oxygen Sensors (Broadley-James), and was maintained to be 20% of the saturated dissolved oxygen concentration. To maintain the dissolved oxygen concentration to be 20% of the saturated concentration, the stirring rate was increased up to 2000 rpm as required, and when the dissolved oxygen concentration was still too low even with the increased stirring rate, the culture was aerated with 30 mL per 1 minute of oxygen disinfected with a filter.

Glucose contained in the production medium was completely consumed at about 4.0 hours after the start of the culture. Immediately thereafter, 0.3 ml of the 1 M (238.3 g/L) IPTG aqueous solution shown in Table 3 was added. Then, culture temperature was set at 30° C., addition of the feed medium shown in Table 4 was started at a flow rate of 4.0 ml per 1 hour, and the culture was continued. During the culture, the culture was aerated with 300 mL per 1 minute of air disinfected with a filter, and stirred at a rate of 700 rpm. During the culture, the dissolved oxygen concentration in the culture medium was measured by using a dissolved oxygen concentration sensor, OxyProbe (registered trademark) Dissolved Oxygen Sensors (Broadley-James), and was maintained to be 20% of the saturated dissolved oxygen concentration. To maintain the dissolved oxygen concentration to be 20% of the saturated concentration, the stirring rate was increased up to 2000 rpm as required. The culture was continued with controlling pH of the culture medium at a constant pH of 6.9 by appropriately blowing ammonia gas into the culture medium.

Analysis

In the culture described in the sections (1) and (2) above, the culture medium was sampled in appropriate volumes during the culture and after the end of the culture, and subjected to the analysis described below.

Figure 10A:
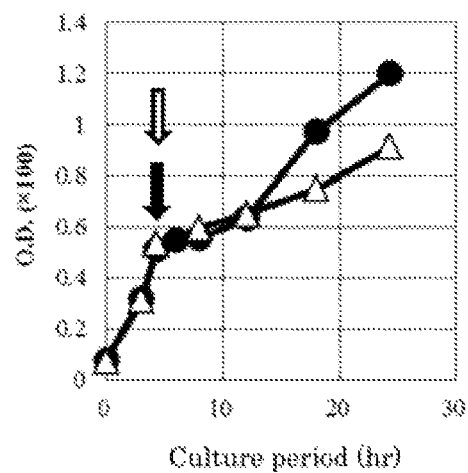
FIG. 10(A) to FIG. 10(C): Graphs showing the results of culture: (A) change of OD620 over time, (B) consumption amount of glucose observed after addition of an IPTG solution, and (C) cumulative specific glucose consumption rate observed after addition of an IPTG solution. The symbols ● indicate the results obtained with the control condition, and the symbols Δ indicate the results obtained with the carbon source-limited condition. The arrows indicate the time points at which an IPTG solution was added.
Figure 10B:
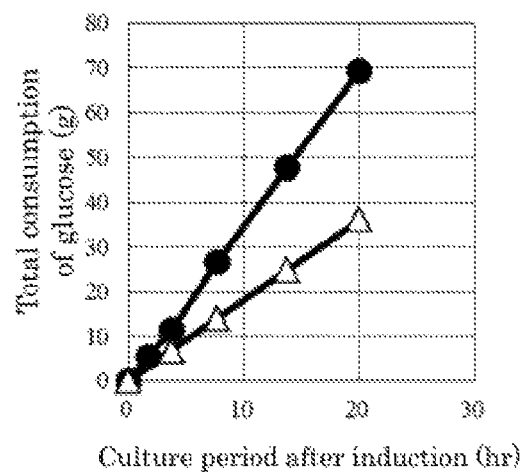
Figure 10C:
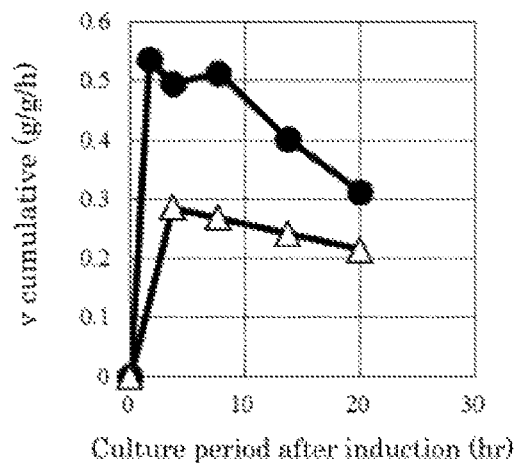
Figure 11A:
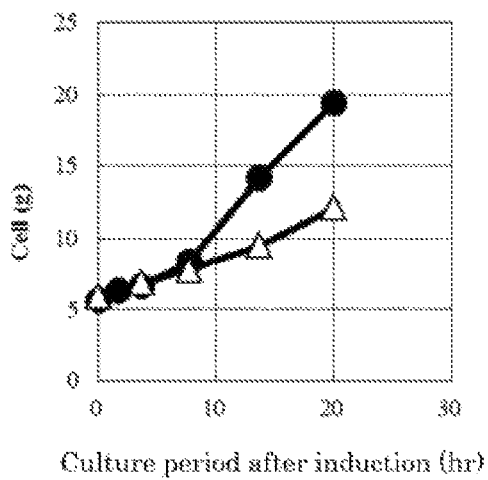
FIG. 11(A) and FIG. 11(B): Graphs showing the results concerning the cell proliferation after addition of an IPTG solution: (A) cell amount, and (B) cumulative specific proliferation rate. The symbols ● indicate the results obtained with the control condition, and the symbols Δ indicate the results obtained with the carbon source-limited condition.
Figure 11B:
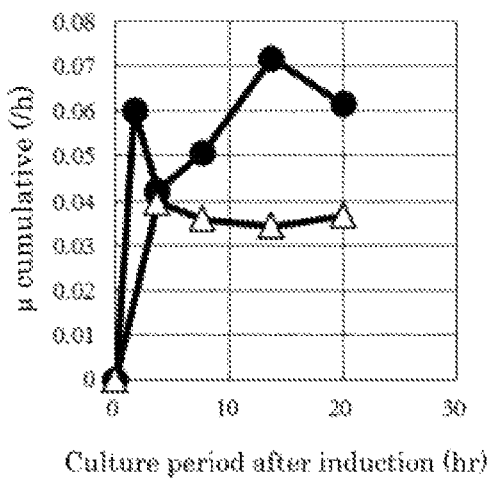

OD620 of the culture medium was measured by the method described in Reference Example 2. The measurement results of OD620 are shown in FIG. 10A. The glucose consumption amount and cumulative specific glucose consumption rate (v-cumulative) are shown in FIGS. 10B and 10C, respectively. The data concerning cell proliferation after addition of the IPTG solution (cell amount, and cumulative specific proliferation rate) are shown in FIGS. 11A and 11B, respectively.

Figure 12A:
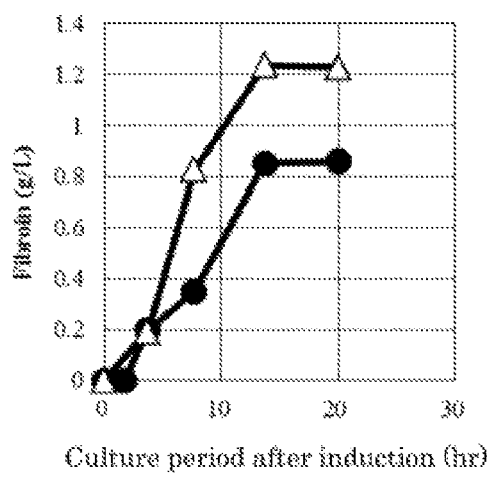
FIG. 12(A) to FIG. 12(C): Graphs showing the results concerning production of fibroin-like protein after addition of an IPTG solution: (A) accumulation amount of fibroin-like protein relative to volume of culture medium; (B) accumulation amount of fibroin-like protein relative to cell weight; and (C) cumulative productivity of fibroin-like protein. The symbols ● indicate the results obtained with the control condition, and the symbols Δ indicate the results obtained with the carbon source-limited condition.
Figure 12B:
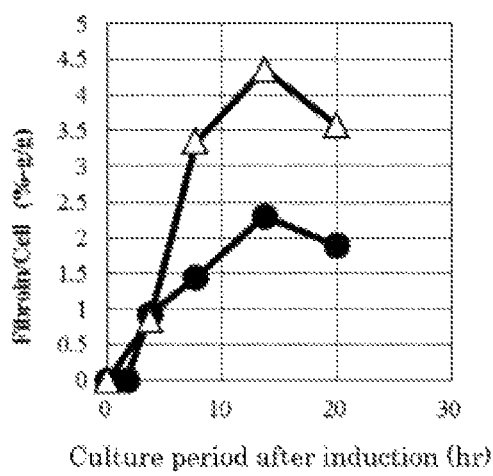
Figure 12C:
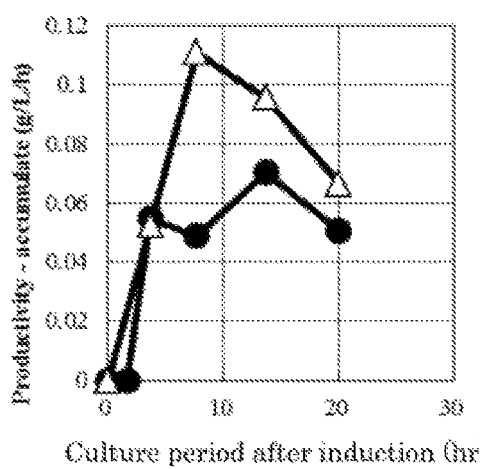

The produced fibroin-like protein was appropriately quantified. The data concerning the production amount of fibroin-like protein, that is, accumulation amount of fibroin-like protein relative to volume of the culture medium, accumulation amount of fibroin-like protein relative to cell weight, and cumulative productivity of fibroin-like protein, are shown in FIGS. 12A to 12C, respectively.

The total glucose consumption amount observed at 13.7 hours after the addition of IPTG was 47.6 g under the control condition, but it decreased to 24.8 g under the carbon source-limited condition. The cumulative specific glucose consumption rate observed at 13.7 hours after the addition of IPTG was 0.40 g/g/h under the control condition, but it decreased to 0.24 g/g/h under the carbon source-limited condition.

The cumulative specific proliferation rate observed at 13.7 hours after the addition of IPTG was 0.071/h under the control condition, but it decreased to 0.034/h under the carbon source-limited condition.

The accumulation amount of the fibroin-like protein relative to volume of the culture medium was 0.85 g/L at 13.7 hours after the addition of IPTG under the control condition, but it was improved to 1.24 g/L at 13.7 hours after the addition of IPTG under the carbon source-limited condition. The accumulation amount of the fibroin-like protein relative to cell weight was 2.31% at 13.7 hours after the addition of IPTG under the control condition, but it was improved to 4.35% at 24 hours after the addition of IPTG under the carbon source-limited condition. The cumulative productivity of the fibroin-like protein was 0.070 g/L/hr at 13.7 hours after the addition of IPTG under the control condition, but it was improved to 0.096 g/L/hr at 13.7 hours after the addition of IPTG under the carbon source-limited condition.

On the basis of the results described above, it was revealed that by performing the culture under the carbon source-limited condition during the period after inducing the expression, the cell proliferation during that period is decreased, and production of the fibroin-like protein was improved.

Example 5: Production of Fibroin-Like Protein Under Condition of Reducing Amount of Required Amino Acid (Ile)

(1) Production of Fibroin-Like Protein Under Control Condition

Culture was performed under the following condition. In Example 5, this condition is also referred to as "control condition".

By using the medium for seed culture shown in Table 9, culture was performed under the condition described in Reference Example 2 until glucose was completely consumed to obtain a seed culture broth. Then, to 255 ml of the production medium shown in Table 10, which was contained in a jar fermenter, 45 ml of the above seed culture broth was inoculated. Culture was performed while maintaining temperature of the culture medium at 37° C., aerating with 300 mL per 1 minute of air disinfected with a filter, stirring at 700 rpm, and maintaining the pH of the culture medium at a constant pH of 6.9 by appropriately blowing ammonia gas into the medium. During the culture, the culture medium was periodically sampled, and the glucose concentration in the culture medium was measured by using BF-5 (Oji Scientific Instruments). During the culture, the dissolved oxygen concentration in the culture medium was also measured by using a dissolved oxygen concentration sensor, OxyProbe (registered trademark) Dissolved Oxygen Sensors (Broadley-James), and was maintained to be 20% of the saturated dissolved oxygen concentration. To maintain the dissolved oxygen concentration at 20% of the saturated concentration, the stirring rate was increased up to 2000 rpm as required, and when the dissolved oxygen concentration was still too low even with the increased stirring rate, the culture was aerated with 30 mL per 1 minute of oxygen disinfected with a filter.

Glucose contained in the production medium was completely consumed at about 4.0 hours after the start of the culture. Immediately thereafter, 0.3 ml of the 1 M IPTG aqueous solution shown in Table 3 was added. Then, culture temperature was set at 30° C., addition of the feed medium shown in Table 5 was started at a flow rate of 3.6 ml per 1 hour, and the culture was continued. During the culture, aeration was performed with 300 mL per 1 minute of air disinfected with a filter, and stirring rate was 700 rpm. During the culture, dissolved oxygen concentration in the culture medium was measured by using a dissolved oxygen concentration sensor, OxyProbe (registered trademark) Dissolved Oxygen Sensors (Broadley-James), and was maintained to be 20% of the saturated dissolved oxygen concentration. To maintain the dissolved oxygen concentration to be 20% of the saturated concentration, the stirring rate was increased up to 2000 rpm as required. The culture was continued with controlling pH of the culture medium at a constant pH of 6.9 by appropriately blowing ammonia gas into the culture medium.

(2) Production of Fibroin-Like Protein Under Ile-Limited Condition

According to the following procedures, culture was performed under a condition that the Ile concentration in the production medium (starting medium) was reduced, in order to reduce cell proliferation after inducing the expression of the fibroin-like protein. In Example 5, this condition is also referred to as "Ile-limited condition".

By using the medium for seed culture shown in Table 9, culture was performed under the condition described in Reference Example 2 until glucose was completely consumed to obtain a seed culture broth. Then, to 255 ml of the production medium shown in Table 11, which was contained in a jar fermenter, 45 ml of the above seed culture broth was inoculated. Culture was performed while maintaining the temperature of the culture medium at 37° C., aerating with 300 mL per 1 minute of air disinfected with a filter, stirring at 700 rpm, and maintaining pH of the culture medium at a constant pH of 6.9 by appropriately blowing ammonia gas into the medium. During the culture, the culture medium was periodically sampled, and the glucose concentration in the culture medium was measured by using BF-5 (Oji Scientific Instruments). During the culture, dissolved oxygen concentration in the culture medium was also measured by using a dissolved oxygen concentration sensor, OxyProbe (registered trademark) Dissolved Oxygen Sensors (Broadley-James), and was maintained to be 20% of the saturated dissolved oxygen concentration. To maintain the dissolved oxygen concentration to be 20% of the saturated concentration, the stirring rate was increased up to 2000 rpm as required, and when the dissolved oxygen concentration was still too low even with the increased stirring rate the culture wag aerated with 10 mL per 1 minute of oxygen disinfected with a filter

TABLE 11

| Production medium (per 1 L at the time of start of culture) | |
| --- | --- |
| Glucose | 45 g |
| $KH_2PO_4$ | 9 g |
| $MgSO_4 \cdot 7H_2O$ | 2.4 g |
| CSL | 1 g (as nitrogen amount) |
| $FeSO_4 \cdot 7H_2O$ | 40 mg |
| $MnSO_4 \cdot 5H_2O$ | 40 mg |
| $CaCl_2 \cdot 2H_2O$ | 40 mg |
| Isoleucine (Ile) | 0.75 g |
| GD-113 (anti-foaming agent) | 0.1 mL |

Stock solutions were prepared for glucose and $MgSO_4 \cdot 7H_2O$ as solution A, CSL (corn steep liquor) as solution B, and the other ingredients as solution C. Then, the stock solutions A and C, as is, were separately sterilized in an autoclave at 120° C. for 20 minutes. The pH of the stock solution B was lowered to 2 by using sulfuric acid, and the solution was subjected to a heat treatment at 80° C. for 60 minutes, and then sterilized in an autoclave at 120° C. for 20 minutes. Then, the stock solutions A, B, and C were mixed to obtain the production medium.

Glucose contained in the production medium was completely consumed at about 4.0 hours after the start of the culture. Immediately thereafter, 0.3 ml of the 1 M IPTG aqueous solution shown in Table 3 was added. Then, culture temperature was set at 30° C., addition of the feed medium shown in Table 5 was started at a flow rate of 3.6 ml per 1 hour, and the culture was continued. During the culture, the culture was aerated with 300 mL per 1 minute of air disinfected with a filter, and stirred at a rate of 700 rpm. During the culture, the dissolved oxygen concentration in the culture medium was measured by using a dissolved oxygen concentration sensor, OxyProbe (registered trademark) Dissolved Oxygen Sensors (Broadley-James), and was maintained to be 20% of the saturated dissolved oxygen concentration. To maintain the dissolved oxygen concentration to be 20% of the saturated concentration, the stirring rate was increased up to 2000 rpm as required. The culture was continued with controlling pH of the culture medium at a constant pH of 6.9 by appropriately blowing ammonia gas into the culture medium.

(3) Analysis

In the culture described in the sections (1) and (2) above, the culture medium was sampled in appropriate volumes during the culture and after the end of the culture, and subjected to the analysis described below.

Figure 13:
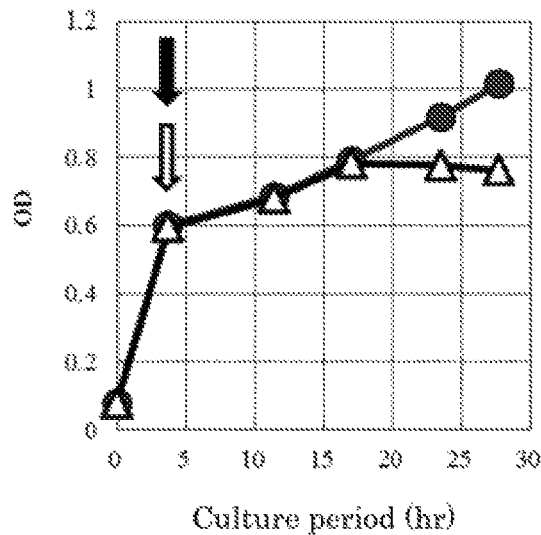
FIG. 13: Graph showing change of OD620 over time. The symbols ● indicate the results obtained with the control condition, and the symbols Δ indicate the results obtained with the Ile-limited condition. The arrows indicate the time points at which an IPTG solution was added.

OD620 of the culture medium was measured by the method described in Reference Example 2. The data concerning OD620 are shown in FIG. 13. The data concerning cell proliferation after addition of the IPTG solution (cumulative specific proliferation rate) are shown in Table 12.

Figure 14:
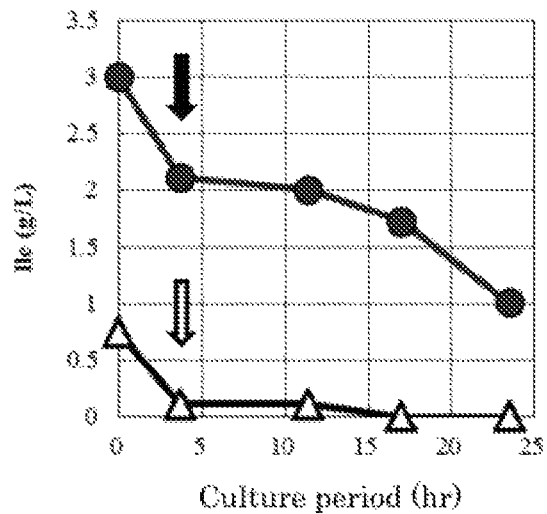
FIG. 14: Graph showing change of the Ile concentration over time. The symbols ● indicate the results obtained with the control condition, and the symbols Δ indicate the results obtained with the Ile-limited condition. The arrows indicate the time points at which an IPTG solution was added.

The Ile concentration in the culture medium was measured by the following method. A culture supernatant separated from the culture medium was diluted 100 times with 0.2 N HCl, and analyzed by using an amino acid analyzer LC-8800C (Shimadzu). The measurement results are shown in FIG. 14. The total consumption amounts of Ile after the addition of IPTG solution are shown in Table 12.

The produced fibroin-like protein was appropriately quantified. The data concerning the production amount of fibroin-like protein, that is, accumulation amount of fibroin-like protein relative to volume of the culture medium, and accumulation amount of fibroin-like protein relative to cell weight, are shown in Table 12.

The total consumption amount of Ile observed at 24 hours after the addition of IPTG, that is, 28 hours after the start of the culture, was 0.244 g under the control condition, but it decreased to 0.033 g under the Ile-limited condition.

The cumulative specific proliferation rate observed at 24 hours after the addition of IPTG was 0.033/h under the control condition, but it decreased to 0.020/h under the Ile-limited condition.

The accumulation amount of the fibroin-like protein relative to cell weight observed at 24 hours after the addition of IPTG was 3.04% under the control condition, but it was improved to 4.79% under the Ile-limited condition.

On the basis of the results described above, it was revealed that by performing the culture under the Ile-limited condition during the period after inducing the expression, the cell proliferation during that period is decreased, and production of the fibroin-like protein was improved.

TABLE 12

| | Control (●) at 24 hours after addition of IPTG | Ile limitation (Δ) at 24 hours after addition of IPTG |
| --- | --- | --- |
| Fibroin (g/L) | 1.24 | 1.26 |
| Fibroin/cell (%-w/w) | 3.04 | 4.79 |
| Cumulative specific proliferation rate after induction (/h) | 0.033 | 0.020 |
| Ile consumption amount after induction (g) | 0.244 | 0.033 |

Example 6: Production of Wild-Type ADF3 Under Condition of Enhancing Cell Proliferation Before Inducing Expression (A) Construction of wild-type ADF3-producing bacterium In this example, ADF3 of *Araneus diadematus* having a His tag and the HRV3C protease recognition sequence added to the N-terminus was produced as a fibroin-like protein. In this example, this fusion protein is also referred to simply as "wild-type ADF3".

A DNA encoding the wild-type ADF3 was introduced into pET22b(+) at the NdeI-EcoRI site by using the In-Fusion kit to obtain an expression plasmid for the wild-type ADF3, pET22b-ADF3WT. *Escherichia coli* BLR(DE3) was transformed with pET22b-ADF3WT to obtain a wild-type ADF3-producing bacterium, BLR(DE3)/pET22b-ADF3WT. The nucleotide sequence of the coding region of wild-type ADF3 and surrounding sequences thereof in pET22b-ADF3WT are shown as SEQ ID NO: 4. The sequence of the positions 12 to 1994 in the sequence of SEQ ID NO: 4 corresponds to the coding region of the wild-type ADF3. The amino acid sequence of the wild-type ADF3 encoded by pET22b-ADF3WT is shown as SEQ ID NO: 5.

(B) Production of wild-type ADF3

(1) Production of Wild-Type ADF3 Under Control Condition

Culture was performed under the following condition. In Example 6, this condition is also referred to as "control condition".

By using the medium for seed culture shown in Table 9, culture was performed under the condition described in Reference Example 2 until glucose was completely consumed to obtain a seed culture broth. Then, to 255 ml of the production medium shown in Table 10, which was contained in a jar fermenter, 45 ml of the above seed culture broth was inoculated. Culture was performed while maintaining the temperature of the culture medium at 37° C., aerating with 300 mL per 1 minute of air disinfected with a filter, stirring at 700 rpm, and maintaining pH of the culture medium at a constant pH of 6.9 by appropriately blowing ammonia gas into the medium. During the culture, the culture medium was periodically sampled, and the glucose concentration in the culture medium was measured by using BF-5 (Oji Scientific Instruments). During the culture, the dissolved oxygen concentration in the culture medium was also measured by using a dissolved oxygen concentration sensor, OxyProbe (registered trademark) Dissolved Oxygen Sensors (Broadley-James), and was maintained to be 20% of the saturated dissolved oxygen concentration. To maintain the dissolved oxygen concentration to be 20% of the saturated concentration, the stirring rate was increased up to 2000 rpm as required, and when the dissolved oxygen concentration was still too low even with the increased stirring rate, the culture was aerated with 30 mL per 1 minute of oxygen disinfected with a filter.

Glucose contained in the production medium was completely consumed at about 4.0 hours after the start of the culture. Immediately thereafter, 0.3 ml of the 1 M IPTG aqueous solution shown in Table 3 was added. Then, culture temperature was set at 30° C., addition of the feed medium shown in Table 13 was started at a flow rate of 2.6 ml per 1 hour, and the culture was continued. During the culture, with the culture was aerated at 300 mL per 1 minute of air disinfected with a filter, and stirring rate was 700 rpm. During the culture, the dissolved oxygen concentration in the culture medium was measured by using a dissolved oxygen concentration sensor, OxyProbe (registered trademark) Dissolved Oxygen Sensors (Broadley-James), and was maintained to be 20% of the saturated dissolved oxygen concentration. To maintain the dissolved oxygen concentration to be 20% of the saturated concentration, the stirring rate was increased up to 2000 rpm as required. The culture was continued with controlling the pH of the culture medium at a constant pH of 6.9 by appropriately blowing ammonia gas into the culture medium.

TABLE 13

| Feed medium (per 1 L) | |
|---|---|
| Glucose | 700 g |

The medium was sterilized in an autoclave at 120° C. for 20 minutes.

(2) Production of Wild-Type ADF3 Under Condition of Enhancing Cell Proliferation Before Inducing Expression According to the following procedures, culture was performed under a condition that a sufficient amount of glucose was fed before inducing the expression of the wild-type ADF3 to allow the cells to sufficiently grow before the induction of the expression in order to reduce cell proliferation after inducing the expression. In Example 6, this condition is also referred to as "condition that cell proliferation before inducing the expression is enhanced".

By using the medium for seed culture shown in Table 9, culture was performed under the condition described in Reference Example 2 until glucose was completely consumed to obtain a seed culture broth. Then, to 255 ml of the production medium shown in Table 10, which was contained in a jar fermenter, 45 ml of the above seed culture broth was inoculated. Culture was performed while maintaining the temperature of the culture medium at 37° C., aerating with 300 mL per 1 minute of air disinfected with a filter, stirring at 700 rpm, and maintaining pH of the culture medium at a constant pH of 6.9 by appropriately blowing ammonia gas into the medium. During the culture, the culture medium was periodically sampled, and the glucose concentration in the culture medium was measured by using BF-5 (Oji Scientific Instruments). During the culture, the dissolved oxygen concentration in the culture medium was also measured by using a dissolved oxygen concentration sensor, OxyProbe (registered trademark) Dissolved Oxygen Sensors (Broadley-James), and was maintained to be 20% of the saturated dissolved oxygen concentration. For maintaining the dissolved oxygen concentration to be 20% of the saturated concentration, the stirring rate was increased up to 2000 rpm as required, and when the dissolved oxygen concentration was still too low even with the increased stirring rate, aeration was also performed with 30 mL per 1 minute of oxygen disinfected with a filter.

Glucose contained in the production medium was completely consumed at about 4.0 hours after the start of the culture. Immediately thereafter, addition of the feed medium shown in Table 13 was started at a flow rate of 14.6 ml per 1 hour, and the culture was continued. During the culture, the culture was aerated with 300 mL per 1 minute of air disinfected with a filter, and stirring rate was 700 rpm. During the culture, dissolved oxygen concentration in the culture medium was measured by using a dissolved oxygen concentration sensor, OxyProbe (registered trademark) Dissolved Oxygen Sensors (Broadley-James), and was maintained to be 20% of the saturated dissolved oxygen concentration. To maintain the dissolved oxygen concentration to be 20% of the saturated concentration, the stirring rate was increased up to 2000 rpm as required, and when the dissolved oxygen concentration was still too low even with such increase of stirring rate, aeration was also performed with 30 to 90 mL per 1 minute of oxygen disinfected with a filter. When it became difficult to maintain the intended dissolved oxygen concentration, the flow rate of the feed medium was decreased. The culture was continued with controlling pH of the culture medium at a constant pH of 6.9 by appropriately blowing ammonia gas into the culture medium.

After about 8 hours from the start of the culture, that is, at the time point when the feeding volume of the feed medium shown in Table 13 reached 58 mL, 1.1 ml of the 1 M IPTG aqueous solution shown in Table 3 was added. Then, the culture temperature was set at 30° C., addition of the feed medium shown in Table 13 was started at a flow rate of 2.6 ml per 1 hour, and the culture was continued. During the culture, aeration was performed with 300 mL per 1 minute of air disinfected with a filter, and stirring rate was 700 rpm. During the culture, dissolved oxygen concentration in the culture medium was measured by using a dissolved oxygen concentration sensor, OxyProbe (registered trademark) Dissolved Oxygen Sensors (Broadley-James), and was maintained to be 20% of the saturated dissolved oxygen concentration. For maintaining the dissolved oxygen concentration to be 20% of the saturated concentration, the stirring rate was increased up to 2000 rpm as required. The culture was continued with controlling pH of the culture medium at a constant pH of 6.9 by appropriately blowing ammonia gas into the culture medium.

(3) Analysis

In the culture described in the sections (1) and (2) above, the culture medium was sampled in appropriate volumes during the culture and after the end of the culture, and subjected to the analysis described below.

Figures 15A, 15B:
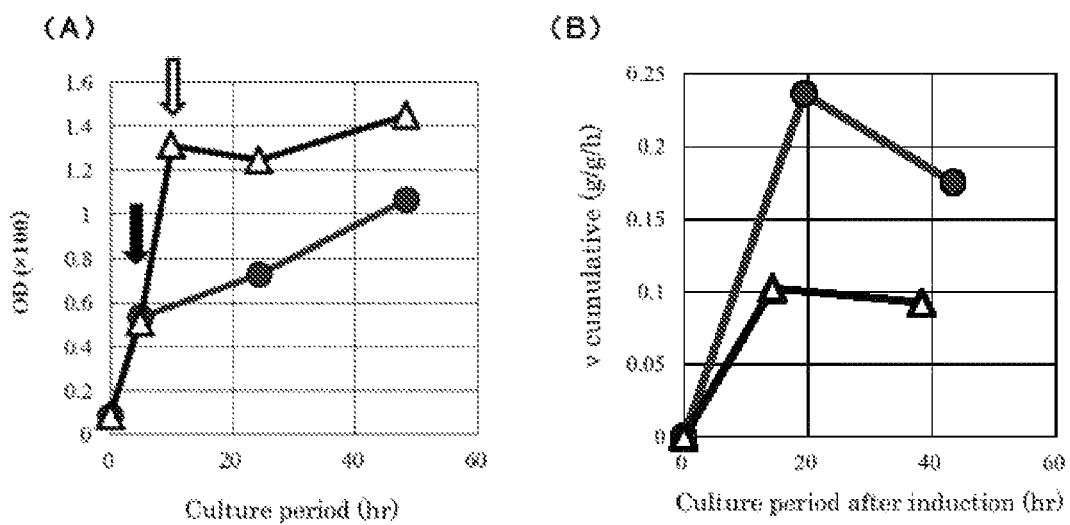
FIG. 15(A) and FIG. 15(B): Graphs showing the results of culture: (A) change of OD620 over time, and (B) cumulative specific glucose consumption rate observed after addition of an IPTG solution. The symbols ● indicate the results obtained with the control condition, and the symbols Δ indicate the results obtained under conditions of enhanced cell proliferation before inducing the expression. The arrows indicate the time points at which an IPTG solution was added.
Figures 16A, 16B, 16C, 16D:
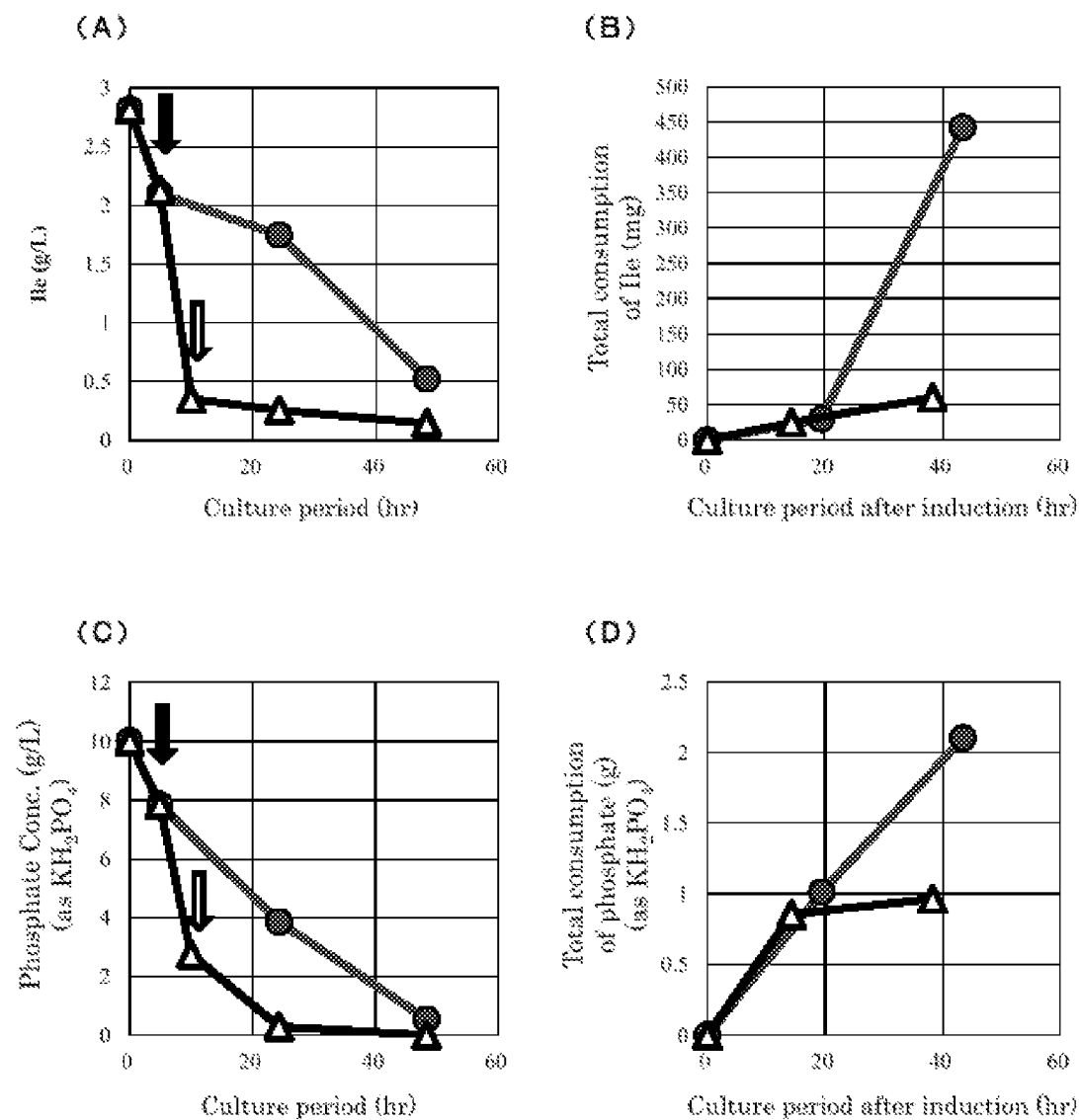
FIG. 16(A) to FIG. 16(D): Graphs showing the results of culture: (A) Ile concentration in the culture medium, (B) total consumption amount of Ile; (C) phosphate concentration in the culture medium (in terms of $KH_2PO_4$ concentration), and (D) total phosphate consumption amount (in terms of $KH_2PO_4$ amount). The symbols ● indicate the results obtained with the control condition, and the symbols Δ indicate the results obtained under conditions of enhanced cell proliferation before inducing the expression. The arrows indicate the time points at which an IPTG solution was added.
Figures 17A, 17B, 17C, 17D:
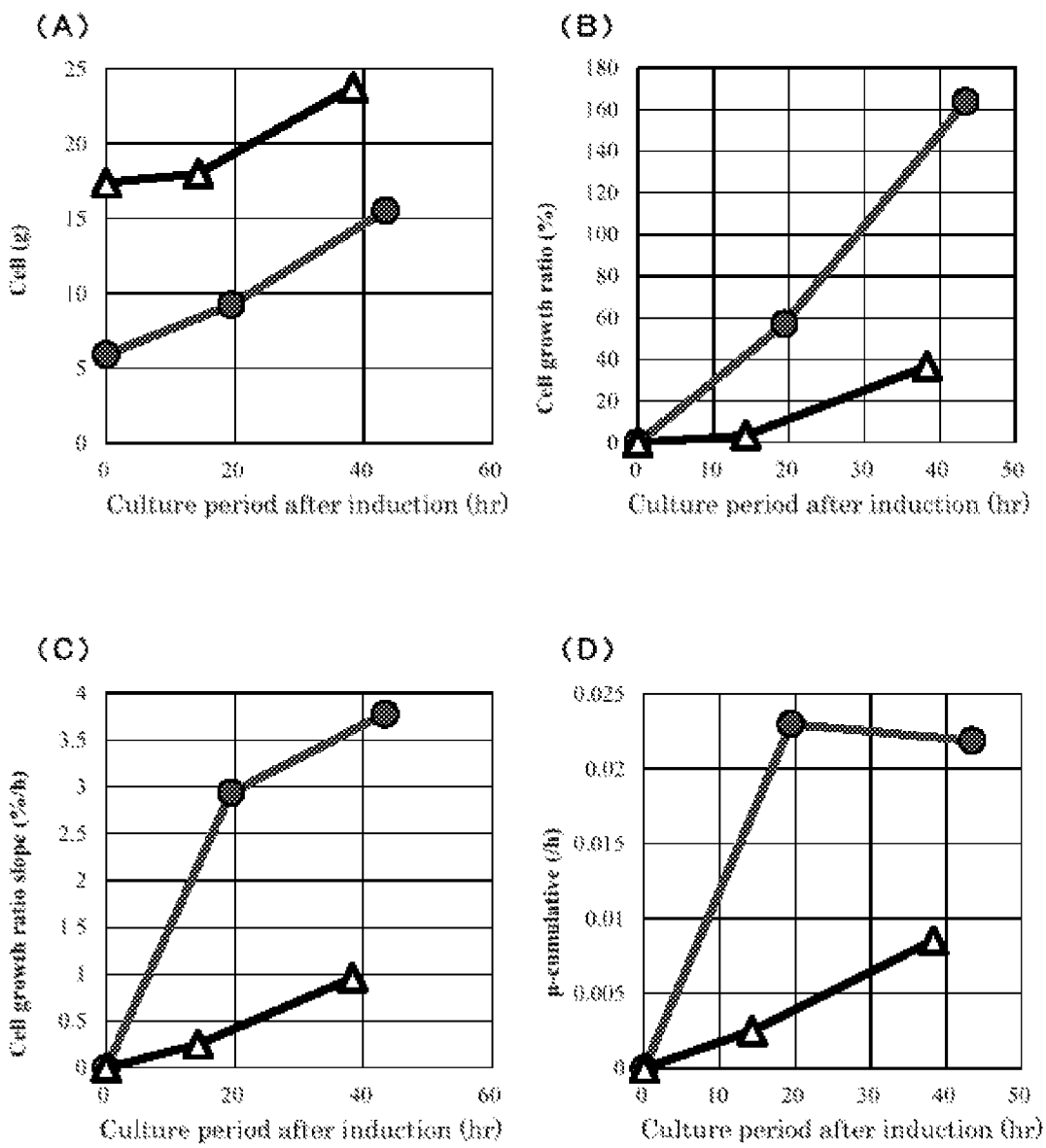
FIG. 17(A) to FIG. 17(D): Graphs showing the results concerning the cell proliferation after addition of an IPTG solution: (A) cell amount, (B) cell growth rate, (C) cell growth rate slope, and (D) cumulative specific proliferation rate. The symbols ● indicate the results obtained with the control condition, and the symbols Δ indicate the results obtained under conditions of enhanced cell proliferation before inducing the expression. The arrows indicate the time points at which an IPTG solution was added.

OD620 of the culture medium was measured by the method described in Reference Example 2. The measurement results are shown in FIG. 15A. The cumulative specific glucose consumption rate (v-cumulative) after the addition of IPTG solution is shown in FIG. 15B. The Ile concentration in the medium was measured by the method described in Example 5. The Ile concentration and total Ile consumption amount after the addition of IPTG solution are shown in FIGS. 16A and 16B, respectively. The phosphate concentration in the medium was measured by the method described in Example 2. The phosphate concentration in terms of $KH_2PO_4$ concentration and the total phosphate consumption amount after the addition of IPTG solution in terms of $KH_2PO_4$ amount are shown in FIGS. 16C and 16D, respectively. The data concerning cell proliferation after addition of the IPTG solution, that is, the cell amount, cell growth rate, cell growth rate slope, and cumulative specific proliferation rate, are shown in FIGS. 17A to 17D, respectively, and Table 14.

Figure 18A:
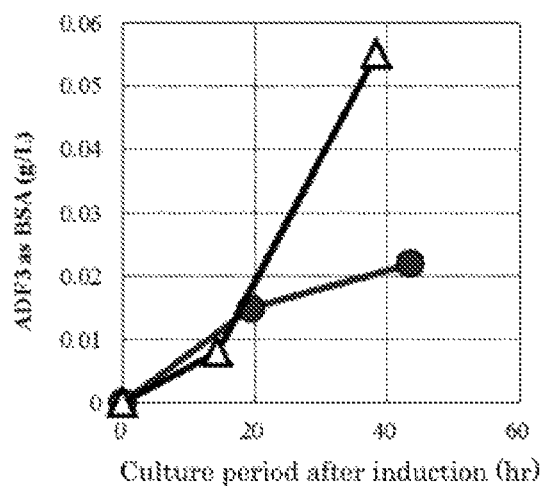
FIG. 18(A) to FIG. 18(C): Graphs showing the results concerning production of wild-type ADF3 after addition of an IPTG solution: (A) accumulation amount of ADF3 relative to volume of culture medium; (B) accumulation amount of ADF3 relative to cell weight; and (C) cumulative productivity of ADF3. The symbols ● indicate the results obtained with the control condition, and the symbols Δ indicate the results obtained under conditions of enhanced cell proliferation before inducing the expression.
Figure 18B:
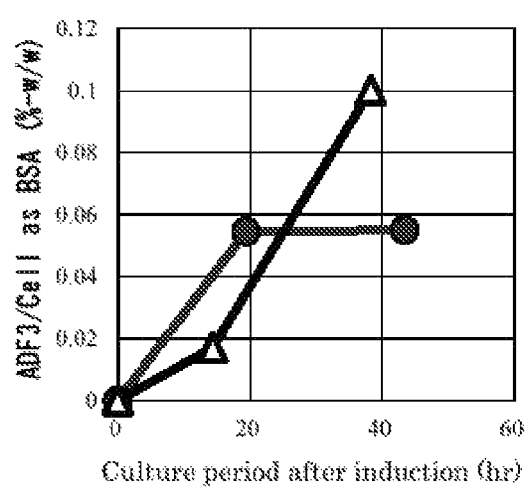
Figure 18C:
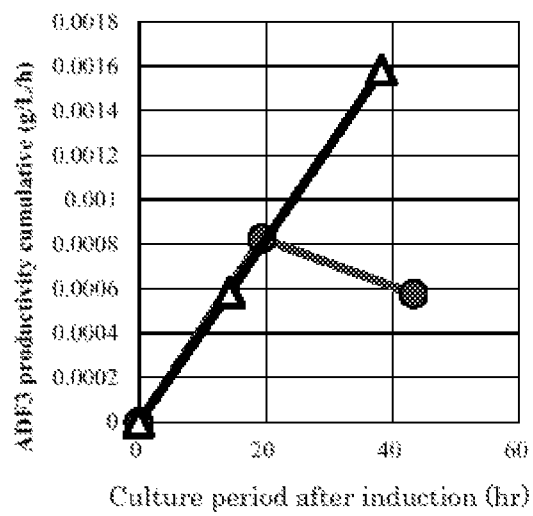

The produced wild-type ADF3 was appropriately quantified. The data concerning the production amount of the wild-type ADF3, that is, the accumulation amount of wild-type ADF3 relative to volume of the culture medium, the accumulation amount of wild-type ADF3 relative to cell weight, and the cumulative productivity of wild-type ADF3) are shown in FIG. 18A to 18C, respectively, and Table 14.

The cumulative specific proliferation rate was 0.022/h at 42 hours after the addition of IPTG under the control condition, but it decreased to 0.009/h at 38 hours after the addition of IPTG under the condition that cell proliferation before inducing the expression was enhanced. The cell growth rate was 163.8% at 42 hours after the addition of IPTG under the control condition, but it decreased to 36.3% at 38 hours after the addition of IPTG under the condition that cell proliferation before inducing the expression was enhanced. The cell growth rate slope was 3.78%/h at 42 hours after the addition of IPTG under the control condition, but it decreased to 0.96%/h at 38 hours after the addition of IPTG under the condition that cell proliferation before inducing the expression was enhanced.

The accumulation amount of the wild-type ADF3 relative to volume of the culture medium was 0.022 g/L at 42 hours after the addition of IPTG under the control condition, but it was improved to 0.055 g/L at 38 hours after the addition of IPTG under the condition that cell proliferation before inducing the expression was enhanced. The accumulation amount of the wild-type ADF3 relative to cell weight was 0.055% at 42 hours after the addition of IPTG under the control condition, but it was improved to 0.100% at 38 hours after the addition of IPTG under the condition that cell proliferation before inducing the expression was enhanced. The cumulative productivity of the wild-type ADF3 was 0.00058 g/L/h at 42 hours after the addition of IPTG under the control condition, but it was improved to 0.0016 g/L/h at 38 hours after the addition of IPTG under the condition that cell proliferation before inducing the expression was enhanced.

On the basis of the results described above, it was revealed that by allowing the cells to sufficiently grow before inducing the expression, the cell proliferation during the period after inducing the expression was reduced, and production of the wild-type ADF3 was improved.

TABLE 9

|  | Control (●); at 42 hours after addition of IPTG | Enhanced cell proliferation before inducing expression (Δ); at 38 hours after addition of IPTG |
|---|---|---|
| ADF3 as BSA (g/L) | 0.022 | 0.055 |
| ADF3/Cell as BSA (%-w/w) | 0.055 | 0.100 |
| Cumulative productivity of ADF3 (g/L/h) | 0.00058 | 0.0016 |
| Cumulative specific proliferation rate after induction (/h) | 0.022 | 0.009 |
| cell growth rate after induction (%) | 163.8 | 36.8 |
| cell growth rate slope after induction (%/h) | 3.78 | 0.96 |

INDUSTRIAL APPLICABILITY

According to the present invention, a fibroin-like protein can be efficiently produced.

EXPLANATION OF SEQUENCE LISTING

SEQ ID NO: 1: Nucleotide sequence of fibroin-like protein gene used in Examples 1 to 5

SEQ ID NO: 2: Amino acid sequence of protein encoded by the fibroin-like protein gene used in Examples 1 to 5

SEQ ID NO: 3: Amino acid sequence of ADF3 protein (partial) of Araneus diadematus SEQ ID NO: 4: Nucleotide sequence of coding region of wild-type ADF3 and surrounding sequences thereof in pET22b-ADF3WT SEQ ID NO: 5: Amino acid sequence of wild-type ADF3 encoded by pET22b-ADF3WT

The invention claimed is:

1. A method for producing a fibroin-like protein, the method comprising:
- (A) culturing an *Escherichia coli* bacterium having a gene encoding the fibroin-like protein in a culture medium;
- (B) inducing expression of the gene encoding the fibroin-like protein;
- (C) after said inducing, a feed medium is added to said culture medium, wherein said feed medium comprises a reduced amount of or no growth factor, resulting in reduced cell proliferation; and
- (D) collecting the fibroin-like protein;

wherein said reduced amount of the growth factor with respect to all ingredients in said feed medium is less than 30% (w/w), wherein in step (C), said reduced cell proliferation results in cumulative specific proliferation rate of 0.070 (/h) or lower, wherein the fibroin-like protein comprises:
- (a) a fibroin; or
- (b) a fibrous protein having a sequence similar to a repetitive sequence of a fibroin, wherein the sequence similar to a repetitive sequence of a fibroin is a sequence represented by the following formula (I), $$REP1-REP2 \quad (I)$$

wherein the protein (b) has the sequence represented by the formula (I) at the repetition number of 2 or more, wherein, independently for each repetition, the REP1 is an amino acid sequence consisting of a continuous sequence of one or more of the amino acids alanine and glycine, and the length of the REP1 is 2 to 20 residues, and wherein, independently for each repetition, the REP2 is an amino acid sequence comprising one or more of the amino acids glycine, serine, glutamine, and alanine, the total number of glycine, serine, glutamine, and alanine residues is 40% or more of the total number of amino acid residues of the REP2, and the length of the REP2 is 2 to 200 residues.

2. The method according to claim 1, wherein a parameter selected from the group consisting of a) the cell growth rate, b) cell growth rate slope, c) cumulative specific proliferation rate, and d) combinations thereof, is/are reduced after inducing the expression.

3. The method according to claim 1, wherein the growth factor is selected from the group consisting of a) a carbon source, b) nitrogen source, c) phosphate source, d) sulfur source, e) mineral, f) nutrient required because of auxotrophy, and g) combinations thereof.

4. The method according to claim 1, wherein the growth factor is selected from the group consisting of a) a carbon source, b) organic nitrogen source, c) phosphate source, and d) combinations thereof.

5. The method according to claim 1, wherein a ratio of a carbon source with respect to all ingredients in the feed medium fed during a period after inducing the expression is 70% (w/w) or higher.

6. The method according to claim 1, wherein said culturing is performed so that the cumulative specific carbon source consumption rate is 0.35 g/g/hr or lower after inducing the expression.

7. The method according to claim 1, wherein the cell proliferation after inducing the expression is reduced by allowing the cells to sufficiently proliferate before inducing the expression.

* * * * *